US009250234B2

(12) United States Patent
Bertin et al.

(10) Patent No.: US 9,250,234 B2
(45) Date of Patent: Feb. 2, 2016

(54) ENZYME TRIGGERED REDOX ALTERING CHEMICAL ELIMINATION (E-TRACE) IMMUNOASSAY

(75) Inventors: Paul A. Bertin, Chicago, IL (US); Michael J. Ahrens, Evanston, IL (US)

(73) Assignee: OHMX Corporation, Evanston, IL (US)

( * ) Notice: Subject to any disclaimer, the term of this patent is extended or adjusted under 35 U.S.C. 154(b) by 449 days.

(21) Appl. No.: 13/354,200

(22) Filed: Jan. 19, 2012

(65) Prior Publication Data

US 2012/0181186 A1  Jul. 19, 2012

Related U.S. Application Data

(60) Provisional application No. 61/434,122, filed on Jan. 19, 2011, provisional application No. 61/523,679, filed on Aug. 15, 2011.

(51) Int. Cl.
*G01N 33/50* (2006.01)
*G01N 33/543* (2006.01)
(Continued)

(52) U.S. Cl.
CPC .......... *G01N 33/54306* (2013.01); *C12Q 1/005* (2013.01); *G01N 31/22* (2013.01)

(58) Field of Classification Search
CPC .................... G01N 33/2882; G01N 33/54306; G01N 31/22; C12Q 1/54; C12Q 1/6816
USPC .......... 205/777.5, 792; 436/24–34, 74, 83, 84
See application file for complete search history.

(56) References Cited

U.S. PATENT DOCUMENTS

| 4,247,533 | A | 1/1981 | Cerami et al. |
| 4,304,853 | A | 12/1981 | Jozefonvicz et al. |
| 4,469,863 | A | 9/1984 | Ts'o et al. |

(Continued)

FOREIGN PATENT DOCUMENTS

| EP | 02075339 | 7/2009 |
| WO | 90/01559 | 2/1990 |

(Continued)

OTHER PUBLICATIONS

Shabat et al. "Dendritic chain reaction: Responsive release of hydrogen peroxide upon generation and enzymatic oxidation of methanol", Bioorganic & Medicinal Chemistry, vol. 18 (2010) p. 3643-3657.*

(Continued)

*Primary Examiner* — J. Christopher Ball
(74) *Attorney, Agent, or Firm* — Wolf, Greenfield & Sacks, P.C.

(57) ABSTRACT

Described are methods for detecting a target analyte in a test sample by providing a solid support comprising an electrode comprising: (i) a self-assembled monolayer (SAM), (ii) a covalently attached electroactive active moiety (EAM) comprising a transition metal complex comprising a self-immolative moiety and a peroxide sensitive moiety (PSM), wherein said EAM has a first $E^0$; then contacting the target analyte and said solid support under conditions wherein said target analyte reacts with a peroxide generating enzyme to generate peroxide and said self-immolative moiety is removed such that said EAM has a second $E^0$ test sample; and then detecting said second $E^0$ as an indication of the presence of said target analyte. Also provided are compositions for use in the preceding methods.

14 Claims, 16 Drawing Sheets

(51) Int. Cl.
*C12Q 1/00* (2006.01)
*G01N 31/22* (2006.01)

(56) References Cited

U.S. PATENT DOCUMENTS

| | | | |
|---|---|---|---|
| 4,727,036 A | 2/1988 | Knowles et al. |
| 4,806,468 A | 2/1989 | Wagner et al. |
| 5,034,506 A | 7/1991 | Summerton et al. |
| 5,206,144 A | 4/1993 | Zeuthen et al. |
| 5,216,141 A | 6/1993 | Benner |
| 5,235,033 A | 8/1993 | Summerton et al. |
| 5,270,163 A | 12/1993 | Gold et al. |
| 5,386,023 A | 1/1995 | Sanghvi et al. |
| 5,407,759 A | 4/1995 | Ohsuga |
| 5,475,096 A | 12/1995 | Gold et al. |
| 5,567,588 A | 10/1996 | Gold et al. |
| 5,595,877 A | 1/1997 | Gold et al. |
| 5,602,240 A | 2/1997 | De Mesmaeker et al. |
| 5,620,850 A | 4/1997 | Bamdad et al. |
| 5,637,459 A | 6/1997 | Burke et al. |
| 5,637,684 A | 6/1997 | Cook et al. |
| 5,644,048 A | 7/1997 | Yau |
| 5,654,159 A | 8/1997 | Allard et al. |
| 5,683,867 A | 11/1997 | Biesecker et al. |
| 5,705,337 A | 1/1998 | Gold et al. |
| 5,834,224 A | 11/1998 | Ruger et al. |
| 6,013,170 A | 1/2000 | Meade |
| 6,013,459 A | 1/2000 | Meade |
| 6,162,645 A | 12/2000 | Lee et al. |
| 6,248,229 B1 | 6/2001 | Meade |
| 6,348,319 B1 | 2/2002 | Braach-Maksvytis et al. |
| 6,432,723 B1 | 8/2002 | Plaxco et al. |
| 6,495,336 B1 | 12/2002 | Ludin et al. |
| 6,600,026 B1 | 7/2003 | Yu |
| 6,740,518 B1 | 5/2004 | Duong et al. |
| 6,770,190 B1 | 8/2004 | Milanovski et al. |
| 6,927,039 B2 | 8/2005 | Gilardi et al. |
| 6,942,771 B1 | 9/2005 | Kayyem |
| 6,991,926 B2 | 1/2006 | Schmid et al. |
| 7,018,523 B2 | 3/2006 | Meade |
| 7,160,678 B1 | 1/2007 | Kayyem et al. |
| 7,223,837 B2 | 5/2007 | De Groot et al. |
| 7,267,939 B2 | 9/2007 | Meade |
| 7,312,087 B2 | 12/2007 | Duong et al. |
| 7,384,749 B2 | 6/2008 | Kayyem et al. |
| 7,393,645 B2 | 7/2008 | Kayyem et al. |
| 7,514,228 B2 | 4/2009 | Meade |
| 7,560,237 B2 | 7/2009 | O'Connor et al. |
| 7,566,534 B2 | 7/2009 | Meade |
| 7,579,145 B2 | 8/2009 | Meade |
| 7,582,419 B2 | 9/2009 | Meade |
| 7,595,153 B2 | 9/2009 | Meade |
| 7,601,507 B2 | 10/2009 | O'Connor et al. |
| 7,705,045 B2 | 4/2010 | De Groot et al. |
| 7,713,711 B2 | 5/2010 | O'Connor et al. |
| 7,732,140 B2 | 6/2010 | Vandenbark et al. |
| 7,759,073 B2 | 7/2010 | O'Connor et al. |
| 7,759,114 B2 | 7/2010 | Martin et al. |
| 7,803,572 B2 | 9/2010 | Braven et al. |
| 7,807,835 B2 | 10/2010 | Xie et al. |
| 8,114,661 B2 | 2/2012 | O'Connor et al. |
| 8,530,170 B2 | 9/2013 | Bertin |
| 8,734,631 B2 | 5/2014 | Ahrens et al. |
| 8,951,400 B2 | 2/2015 | Ahrens et al. |
| 2002/0009810 A1 | 1/2002 | O'Connor et al. |
| 2002/0121314 A1 | 9/2002 | Tao et al. |
| 2003/0073243 A1 | 4/2003 | Law et al. |
| 2003/0119208 A1 | 6/2003 | Yoon et al. |
| 2005/0123948 A1 | 6/2005 | Claycomb et al. |
| 2005/0189240 A1 | 9/2005 | Lin et al. |
| 2008/0164154 A1 | 7/2008 | Purvis |
| 2008/0248592 A1 | 10/2008 | Bamdad et al. |
| 2009/0041791 A1 | 2/2009 | Feng |
| 2009/0253149 A1 | 10/2009 | Ahrens et al. |
| 2010/0003710 A1 | 1/2010 | Bertin et al. |
| 2010/0025264 A1 | 2/2010 | Yuan et al. |
| 2010/0145036 A1 | 6/2010 | Sufi et al. |
| 2010/0204554 A1 | 8/2010 | Say et al. |
| 2011/0033869 A1 | 2/2011 | Bertin |
| 2012/0012472 A1 | 1/2012 | Ahrens et al. |
| 2012/0034638 A1 | 2/2012 | Ahrens et al. |
| 2012/0156709 A1 | 6/2012 | Bertin et al. |
| 2012/0199499 A1 | 8/2012 | O'Connor et al. |
| 2013/0098777 A1 | 4/2013 | Gaustad |
| 2013/0112572 A1 | 5/2013 | Bertin et al. |
| 2013/0236909 A1 | 9/2013 | Bertin |
| 2013/0264220 A1 | 10/2013 | Bertin et al. |
| 2014/0027309 A1 | 1/2014 | Bao et al. |
| 2014/0027310 A1 | 1/2014 | Gaustad et al. |
| 2014/0134658 A1 | 5/2014 | Ahrens et al. |
| 2014/0311922 A1 | 10/2014 | Ahrens et al. |
| 2014/0322740 A1 | 10/2014 | Ahrens et al. |
| 2014/0342383 A1 | 11/2014 | Bertin et al. |

FOREIGN PATENT DOCUMENTS

| | | |
|---|---|---|
| WO | 93/03379 | 2/1993 |
| WO | 98/20162 A3 | 5/1998 |
| WO | 98/57159 A1 | 12/1998 |
| WO | 99/57317 A1 | 11/1999 |
| WO | 00/11474 | 3/2000 |
| WO | 03/019171 | 3/2003 |
| WO | 2008/045799 | 4/2008 |
| WO | 2009/052422 | 4/2009 |
| WO | 2010/142037 | 12/2010 |
| WO | 2011/034668 A1 | 3/2011 |
| WO | 2011/041586 | 4/2011 |
| WO | 2011/150186 A1 | 12/2011 |
| WO | 2012/100078 A1 | 7/2012 |

OTHER PUBLICATIONS

Murphy et al. "Measurement in vitro of human plasma glycerol with hydrogen peroxide detecting microdialysis enzyme electrode", Analytical Chemistry, vol. 66 (1994) p. 4345-4353.*

Niimura et al. "A hydrogen peroxide-forming NADH oxidase that functions as an alkyl hydroperoxide reductase in *Amphibacillus xylanus*", Journal of Bacteriology, vol. 182, No. 18 (Sep. 2000) p. 5046-5051.*

Chidsey et al. "Coadsorption of ferrocene-terminated and unsubstituted alkanethiols on gold: electroactive self-assembled monolayers", Journal of the American Chemical Society, vol. 112, (1990) p. 4301-4306.*

Definition for term "simultaneously"; Merriam-Webster.com. Merriam-Webster, n.d. Web. Mar. 14, 2014. http://www.merriam-webster.com/dictionary/simultaneous.*

Adjemian, Jocelyne, et al., "Cleavage-Sensing Redox Peptide Monolayers for the Rapid Measurement of the Proteolytic Activity of Trypsin and a-Thrombin Enzymes," Langumuir Article, Jan. 27, 2010, pp. 1-10.

Chin, Curtis D., et al, "Microfluidics-Based Diagnostics of Infectious Diseases in the Developing World," Nature Medicine, Technical Reports, available online Jul. 31, 2011, pp. 1-6.

Gaster, Richard S., et al., "nanoLAB: An Ultraportable, Handheld Diagnostic Laboratory for Global Health," Lab on a Chip, Dynamic Article Links, Jan. 24, 2011, pp. 1-7.

Houseman, Benjamin T., et al., "Peptide Chips for the Quantitative Evaluation of Protein Kinase Activity," Nature Biotechnology, Research Article, Mar. 2002, vol. 20, pp. 270-274.

Kerman, Kagan, et al., "Electrochemical Detection of Kinase-Catalyzed Thiophosphorylation Using Gold Nanoparticles," Chem. Commun. 2007, pp. 5019-5021.

Kerman, Kagan, et al., "Peptide Biosensors for the Electrochemical Measurement of Protein Kinase Activity," Anal. Chem., 2008, vol. 80, pp. 9395-9401.

Kerman, Kagan, et al., "Electrochemical Detection of Protein Tyrosine Kinase-Catalysed Phosphorylation Using Gold Nanoparticles," Biosensors and Bioelectronics, 2009, vol. 24, pp. 1484-1489.

(56) References Cited

OTHER PUBLICATIONS

Kim, S.D., et al., "Gold-Film Array-Electrode for Electrochemical ELISA," Sensors and Actuators B, 2005, pp. 463-469.
Labib, Mahmoud, et al., "A Bioorganometallic Approach for Rapid Electrochemical Analysis of Human Immunodeficiency Virus Type-1 Reverse Transcriptase in Serum," Elsevier, Article in Press, Elecrochimica Acta, available online Mar. 22, 2011, pp. 1-7.
Leinonen, J., et al., "Development of Novel Peptide Ligands Modulating the Enzyme Activity of Prostate-Specific Antigen," Scand. J. Clin. Lab. Invest., 2000, pp. 59-64.
Li, Peng, et al., "Development of an Ultrafast Quantitative Heterogeneous Immunoassay on Prefunctionalized Poly (Dimethylsiloxane), Microfluidic Chips for the Next-Generation Immunosensors," Microfluidics and Nanofluidics, vol. 7, No. 4, Mar. 11, 2009.
Martic, Sanela, et al., "Probing the Role of the Linker in Ferrocene-ATP Conjugates: Monitoring Protein Kinase Catalyzed Phosphorylations Electrochemically," Chemistry A European Journal, 2011, vol. 17, pp. 6744-6752.
Martic, Sanela, et al., "Use of 5-y-Ferrocenyl Adenosine Triphosphate (Fc-ATP) Bioconjugates Having Poly (ethylene glycol) Spacers in Kinase-Catalyzed Phosphorylations," Bioconjugate Chemistry, 2011, pp. 1-10.
Martic, Sanela, et al., "Enzymatically Modified Peptide Surfaces: Towards General Electrochemical Sensor Platform for Protein Kinase Catalyzed Phosphorylations," Analyst, 2011, 136, pp. 107-112.
Nagy, Geza, et al., "Screen-Printed Amperometric Microcell for Proline Iminopeptidase Enzyme Activity Assay," Biosensors & Bioelectronics, 2000, vol. 15, pp. 265-272.
Song, Haifeng, et al., "Electrochemical Detection of Kinase-Catalyzed Phosphorylation Using Ferrocene-Conjugated ATP," Chem. Commun., 2008, pp. 502-504.
Vukmirovic-Popovic, Snezana, et al., "Presence and Enzymatic Activity of Prostate-Specific Antigen in Archival Prostate Cancer Samples," Oncology Reports, 2008, vol. 20, pp. 897-903.
Zhou, Ya-Min, et al., "An Amperometric Immunosensor Based on an Electrochemically Pretreated Carbon-Paraffin Electrode for Complement III (C3) Assay," Biosensors and Bioelectronics, 2008, vol. 18, pp. 473-481.
Batchelor, Robert H., et al., "A Resorufin-Based Fluorescent Assay for Quantifying NADH," Analytical Biochemistry, 2002, vol. 305, pp. 118-119.
Beckett, Dorothy, et al., "A Minimal Peptide Substrate in Biotin Holoenzyme Synthetase-Catalyzed Biotinylation," Protein Science, 1999, vol. 8, pp. 921-929.
Collman, James P., et al., "Role of a Distal Pocket in the Catalytic O2 Reduction by Cytochrome C Oxidase Models Immobilized on Interdigitated Array Electrodes," PNAS, 2009, vol. 106, No. 18, pp. 7320-7323.
Cronan, John E., Jr., "The *E. coli* bio Operon: Transcriptional Repression by an Essential Protein Modification Enzyme," Cell, 1989, vol. 58, pp. 427-429.
Hudson, Richard D.A., "Ferrocene Polymers: Current Architectures, Syntheses and Utility," Journal of Organometallic Chemistry, 2001, pp. 47-69, Abstract only.
Kamidate, Tamio, et al., "Firefly Bioluminescent Assay of ATP in the Presence of ATP Extractant by Using Liposomes," Anal. Chem., 2006, vol. 78, pp. 337-342.
Llaudet, Enrique, et al., "Microelectrode Biosensor for Real-Time Measurement of ATP in Biological Tissue," Anal. Chem., 2005, vol. 77, pp. 3267-3273.
Murphy, Lindy J., et al., "Measurement in Vitro of Human Plasma Glycerol with a Hydrogen Peroxide Detecting Microdialysis Enzyme Electrode," Anal. Chem. 1994, vol. 66, pp. 4345-4353.
Tabata, Masayoshi, et al., "Use of a Biosensor Consisting of an Immobilized NADH Oxidase Column and a Hydrogen Peroxide Electrode for the Determination of Serum Lactate Dehydrogenase Activity," Analytica Chimica Acta, 1994, vol. 298, pp. 113-119.

Wang, Yonghong, et al., "A Sensitive Ligase-Based ATP Electrochemical Assay Using Molecular Beacon-Like DNA," Biosensors and Bioelectronics, 2010, vol. 25, pp. 2101-2106.
U.S. Appl. No. 13/353,001, filed Jan. 18, 2012.
Anne, Christine, et al., "High-Throughput Fluorogenic Assay for Determination of Botulinum Type B Neurotoxin Protease Activity", Analytical Biochemistry, Apr. 2001, vol. 291, No. 2, pp. 253-261. (Abstract only).
Beaucage, Serge L., et al., "The Functionalization of Oligonucleotides Via Phosphoramidite Derivatives," Tetrahedron, Mar. 1993, vol. 49, No. 10, pp. 1925-2138.
Bickert, Peter, et al., "Pentafulvenes: Versatile Synthons in Metallocene Chemistry," Organometallics, 1984, vol. 3, No. 5, pp. 653-657. (Abstract only).
Brill, Wolfgang K.D., et al., "Synthesis of Oligodeoxynucleoside Phosphorodithioates Via Thioamidites" J. Am. Chem. Soc., 1989, vol. 111, No. 6, pp. 2321-2322. (Abstract only).
Defilippis, et al., "Synthesis of Some Para-Functionalized Phenylboronic AcidDerivatives," Synthetic Communications, 2002, vol. 32, No. 17, pp. 2669-2676. (Abstract only).
Egholm M. et al, "PNA Hybridizes to Complementary Oligonucleotides Obeying the Watson-Crick Hydrogen-bonding Rules," Nature, 1993, vol. 365, No. 6446, pp. 566-568. (Abstract only).
Farrington, Edward J., et al., "Synthesis and Reactivity of a Ferrocene-Derived PCP-Pincer Ligand," Chem. Commun., 2002, pp. 308-309. (Abstract only).
Giordano, Ricardo J., et al., "Biopanning and Rapid Analysis of Selective Interactive Ligands," Nature Medicine, 2001, vol. 7. pp. 1249-1253. (Abstract only).
Hallis, B., et al., "Development of novel assays for botulinum type A and B neurotoxins based on their endopeptidase activities," J. Clin. Microbiol., Aug. 1996, vol. 34, No. 8, pp. 1934-1938. (Abstract only).
Heinze, Katja, et al., "Anion-Induced Motion in a Ferrocene Diamide," Euro. J. Inorg. Chem., Jan. 2005, vol. 2005, No. 1, pp. 66-71. (Abstract only).
Heinze, Katja, et al., "Main Chain Ferrocenyl Amides from 1-Aminoferrocene-1'-carboxylic Acid," European Journal of Inorganic Chemistry, Jul. 2004, vol. 2004, No. 14, pp. 2974-2988. (Abstract only).
Horn, Thomas, et al., "Oligonucleotides with Alternating Anionic and Cationic Phosphoramidate Linkages: Synthesis and Hybridization of Stereo-uniform Isomers," Tetrahedron Letters, Feb. 1996, vol. 37, No. 6, pp. 743-746. (Abstract only).
Jeffs, et al., "Unusual conformation of a 3'-thioformacetal linkage in a DNA duplex," J. Biomol. NMR., Jan. 1994, vol. 4, No. 1, pp. 17-34. (Abstract only).
Jung, Paul M., et al., "Hybridization of Alternating Cationic/Anionic Oligonucleotides to RNA Segments" Nucleosides and Nucleotides, 1994, vol. 13, Nos. 6-7, pp. 1597-1605. (Abstract only).
Jwo, Jing-Jer, et al., "Intramolecular Electron Transfer from Pentacyanoferrate(II) to Pentaamminecobalt(III) Mediated by Various 4,4'-bipyridines," J. Am. Chem. Soc., 1979, vol. 101, No. 21, pp. 6189-6197. (Abstract only).
Lavallee, et al., "Charge Delocalization in Pentaammineruthenium(II) Complexes. I. Specteal Properties, Basicities, and Charge Densities by Nuclear Magnetic Resonance Spectroscopy," J. Am. Chem. Soc., 1972, vol. 94, No. 8, pp. 2583-2599. (Abstract only).
Letsinger, Robert L., et al., "Cationic oligonucleotides," J. Am. Chem. Soc., 1988, vol. 110, No. 13, pp. 4470-4471. (Abstract only).
Letsinger, Robert L., et al., "Effects of Pendant Groups at Phosphorus on Binding Properties of d-ApA Analogues," Nucl. Acids Res., 1986, vol. 14, No. 8, pp. 3487-3499. (Abstract only).
Letsinger, Robert L., et al., "Phosporamidate analogs of oligonucleotides," J. Org. Chem., 1970, vol. 35, No. 11, pp. 3800-3803. (Abstract only).
Liu, et al., "Using azobenzene-Embedded Self-Assembled Monolayers to Photochemically Control Cell Adhesion Reversibly," Angew. Chem. Int. Ed. Engl., 2009, vol. 48 ,No. 24, pp. 4406-4408.
Pauwels et al., Chemica Scripta, 1986, vol. 26, pp. 141-149. (Abstract not available).

(56) References Cited

OTHER PUBLICATIONS

Perry-Feigenbaum, Rotem, et al., "The Pyridinone-Methide Elimination," Org. Biomol. Chem., 2009,vol. 7, pp. 4825-4828. (Abstract only).
Sawai, et al., "Synthesis and Properties of Oligoadenylic Acids Containing 2'-5' Phosphoramide Linkage," Chemistry Letters, 1984, pp. 805-808. (Abstract only).
Schiavo, Giampietro, et al., "*Botulinum* Neurotoxins Serotypes A and E Cleave SNAP-25 at Distinct COOH-terminal Peptide Bonds," FEBS Letters, Nov. 1993, vol. 335, No. 1, pp. 99-103.
Schiavo, Giampietro, et al., "Identification of the Nerve Terminal Targets of *Botulinum* Neurotoxin Serotypes A, D, and E," Journal of Biological Chemistry, 1993, vol. 268, No. 32, pp. 23784-23787. (Abstract only).
Sidhu, Sachdev S., et al., "Phage Display for Selection of Novel Binding Peptides," Methods in Enzymology, 2000, vol. 328, pp. 333-363. (Abstract only).
Silverman, Joshua, et al., "Multivalent Avimer Proteins Evolved by Exon Shuffling of a Family of Human Receptor Domains," Nature Biotechnology, 2005, vol. 23, pp. 1556-1561. (Abstract only).
Sprinzl, M., et al., "Enzymatic incorporation of ATP and CTP Analogues into the 3' end of tRNA," European Journal of Biochemistry, Dec. 1977, vol. 81, No. 3, pp. 579-589. (Abstract only).
Tlais, Sami F., et al., "New Strategies for Protecting Group Chemistry: Synthesis, Reactivity, and Indirect Oxidative Cleavage of Para-Siletanylbenzyl Ethers," J. Org. Chem., 2009, vol. 74 No. 5, pp. 1876-1885. (Abstract only).
Wictome, Matthew, et al., "Development of an In Vitro Bioassay for *Clostridium botulinum* Type B Neurotoxin in Foods That is More Sensitive than the Mouse Bioassay," Appl. Environ. Microbiol., Sep. 1999, vol. 65. No. 9, pp. 3787-3792.
Spinke, J., et al., "Molecular Recognition at selfassembled monolayers: Optimization of surface functionalization," The Journal of Chemical Physics, vol. 99, No. 9, Nov. 1993, pp. 7012-7018.
Spinke, J., et al., "Molecular Recognition at self-assembled monolayers: The construction of multicomponent multilayers," Langmuir, 1993, pp. 1821-1825.
Barker, K.D., et al., "Protein Binding and the Electronic Properties of Iron (II) Complexes: An Electrochemical and Optical Investigation of Outer Sphere Effects", Bioconjugate Chemistry, Sep. 29, 2009, vol. 20(10), pp. 1930-1939 (Abstract only).
Bickert, et al., "Pentafulvenes: Versatile Synthons in Metallocene Chemistry," Organometallics, May 1984, vol. 3(5), pp. 654-657.
Callahan, R.W., et al., "Effects of weak metal-metal interactions in ligand-bridged complexes of ruthenium. Dimeric complexes containing ruthenium ions in different coordination environments," Inorg. Chem., Jul. 1975, vol. 14(7), pp. 1443-1453 (Abstract only).
Carlsson, C., et al., "Screening for genetic mutations," Nature, 1996, vol. 380(6571), p. 207 (Abstract unavailable).
Curtis, J.C., et al., "Directed, intramolecular electron transfer in mixed-valence dimers," Inorg. Chem., Jan. 1985, vol. 24(3), pp. 385-397 (Abstract only).
Dempcy, R.O., et al., "Synthesis of a thymidyl pentamer of deoxyribonucleic guanidine and binding studies with DNA homopolynucleotides," Proc. Natl. Acad. Sci. USA, Jul. 20, 1995, vol. 92(13), pp. 6097-6101 (Abstract only).
Egholm, M., et al., "Peptide nucleic acids (PNA). Oligonucleotide analogs with an achiral peptide backbone," J. Am. Chem. Soc., Feb. 1992, vol. 114(5), pp. 1895-1897 (p. 1895 only).
Farrington, E.J., et al., "Synthesis and reactivity of a ferrocene-derived PCP-pincer ligand," Chem. Commun., Jan. 21, 2002, pp. 308-309.
Gardner, J.W., et al., "Application of conducting polymer technology in microsystems," Sensors and Actuators A: Physical, Oct. 1995, vol. 51(1), pp. 57-66 (Abstract only).
Jenkins G.N., et al., "The biosynthesis of carbocyclic nucleosides," Chem. Soc. Rev., 1995, vol. 24, pp. 169-176 (p. 169 only).
Kiedrowski, G., et al., "Parabolic Growth of a Self-Replicating Hexadeoxynucleotide Bearing a 3'-5'-Phosphoamidate Linkage," Angew. Chem. Intl. Ed. English, Apr. 1991, vol. 30(4), pp. 423-426 (Abstract only).
Mag, M., et al., "Synthesis and selective cleavage of an oligodeoxynucleotide containing a bridged intemucleotide 5'-phosphorothioate linkage," Nucleic Acids Res., 1991, vol. 19, pp. 1437-1441 (Abstract only).
Meier, C., et al., "Peptide Nucleic Acids(PNAs)—Unusual Properties of Nonionic Oligonucleotide Analogues," Chem. Int. Ed. Engl., Aug. 1992, vol. 31(8), pp. 1008-1010 (Abstract only).
Mesmaeker, A., et al., "Comparison of rigid and flexible backbones in antisense oligonucleotides," Bioorganic & Medicinal Chem. Lett., Feb. 10, 1994, vol. 4(3) pp. 395-398 (Abstract only).
Neyhart, G.A., et al., "Solvent-Induced Electron Transfer and Delocalization in Mixed-Valence Complexes. Electrochemistry," J. Am. Chem. Soc., Apr. 17, 1996, vol. 118(15), pp. 3724-3729 (Abstract only).
Pichon, et al., "A direct meta-lithiation route to 1,3-disubstituted ferrocenes," Chem. Commun, Feb. 10, 2004, pp. 598-599.
Steurer, et. al., "Bromide-Mediated ortho-Deprotonation in the Synthesis of Chiral, Nonracemic Ferrocene Derivatives," Organometallics, Jun. 19, 2007, vol. 26, pp. 3850-3859.
Bertin, P.A., et al., "Novel redox active bifunctional crosslinkers from unsymmetrical 1,1'-disubstituted ferrocenes," Tetrahedron Lett., Sep. 23, 2009, vol. 50(38), pp. 5409-5412 (abstract only).
Chen, C., et al., "Chemically Modified Electrodes by Nucleophilic Substitution of Chlorosilylated Platinum Oxide Surfaces," Langmuir, Sep. 1994, vol. 10(9), pp. 3332-3337 (abstract only).
Connelly, et al., "Chemical Redox Agents for Organometallic Chemistry," Chem. Rev., Jan. 9, 1996, vol. 96, pp. 877-910.
Deinhammer et al., "Electrochemical oxidation of amine-containing compounds: a route to the surface modification of glassy carbon electrodes," Langmuir, 1994, vol. 10(4), pp. 1306-1313 (abstract only).
Gassman, et al., "(Trifluoromethyl)cyclopentadienide: a powerful electron-withdrawing ligand for transition-metal complexes," J. Am. Chem. Soc., Jul. 1986, vol. 108(14), pp. 4228-4229 (abstract only).
Gray, et al., "Electron Transfer in Proteins," Annual Rev. Biochem, 1996, vol. 65, p. 537-561.
Li, et al., "Nanoscale 1,3,5,7-Tetrasubstituted Adamantanes and p-Substituted Tetraphenyl-methanes for AFM Applications," Org. Lett., Sep. 18, 2002, vol. 4(21), pp. 3631-3634 (abstract only).
Lo, L., et al., "Development of highly selective and sensitive probes for hydrogen peroxide," Chem. Commun., 2003, pp. 2728-2729.
Robbins, et al., "Syntheses and electronic structures of decamethylmetallocenes," J. Am. Chem. Soc., Apr. 1982, vol. 104(7), pp. 1882-1893 (abstract only).
Sagi, et al.,"Amperometric Assay for Aldolase Activity; Antibody-Catalyzed Ferrocenylamine Formation," Anal. Chem., 2006, vol. 78(5), pp. 1459-1461 (abstract only).
Sella, E., et al., "Self-immolative dendritic probe for the direct detection of triacetone triperoxide," Chem. Commun., Oct. 15, 2008, Issue 44, pp. 5701-5703 (abstract only).
Wei, et al., "Diverse Redox-Active Molecules Bearing Identical Thiol-Terminated Tripodal Tethers for Studies of Molecular Information Storage," J. Org. Chem., 2004, vol. 69(5), pp. 1461-1469 (abstract only).
Xiang, Yu, et al., "Using personal glucose meters and functional DNA sensors to quantify a variety of analytical targets," Nature Chemistry, Sep. 2011, vol. 3, pp. 697-703.
International Search Report and Written Opinion for PCT/US2012/021904, mailed May 9, 2012.
International Preliminary Report on Patentability for PCT/US2012/021904, issued Jul. 23, 2013.
Bennett, Complexes of Ruthenium and Osmium Containing n2-n6 Hydrocarbon Ligands: (i) Complexes not Containing Cyclobutadiene, Cyclopentadienyl or n-Arene Coligands. *Comprehensive Organometallic Chemistry II, A Review of the Literature 1982-1994*. vol. 7, Abel et al., (Eds) Pergamon Press. 1995. Chapter 7, pp. 441-472.
Bennett et al., Complexes of Ruthenium and Osmium Containing n2-n6 Hydrocarbon Ligands: (ii) Complexes Containing Four- and

(56) References Cited

OTHER PUBLICATIONS

Five-membered Rings (Including MCp(arene) Complexes). *Comprehensive Organometallic Chemistry II, A Review of the Literature 1982-1994.* vol. 7, Abel et al., (Eds) Pergamon Press. 1995. Chapter 8, pp. 473-548.

Bruce, Ruthenocenes and Osmocenes. *Comprehensive Organometallic Chemistry II, A Review of the Literature 1982-1994.* vol. 7, Abel et al., (Eds) Pergamon Press. 1995. Chapter 10, pp. 603-624.

Connelly et al., The Electron-Transfer Reactions of Mononuclear Organotransition Metal Complexes. Advances in Organometallic Chemistry. 1984; 23:1-93.

Cotton et al., Advanced Organic Chemistry, 5th Edition, John Wiley & Sons, Inc., 1988, p. 38 and Chapt. 26:1152-1185.

Gao et al., Unusual conformation of a 3'-thioformacetal linkage in a DNA duplex. J Biomol NMR. Jan. 1994;4(1):17-34. (Abstract Only).

Geiger et al., The Electron-Transfer Reactions of Polynuclear Organotransition Metal Complexes. Advances in Organometallic Chemistry. 1985; 24:87-130.

Haines, Binuclear Complexes of Ruthenium and Osmium Containing Metal-Metal Bonds. *Comprehensive Organometallic Chemistry II, A Review of the Literature 1982-1994.* vol. 7, Abel et al., (Eds) Pergamon Press. 1995. Chapter 11, pp. 625-681.

Lenhard et al., Chemically modified electrodes: Part VII. Covalent bonding of a reversible electrode reactant to Pt electrodes using an organosilane reagent. J. Electroanal. Chem. May 10, 1977; 78(1):195-201.

Mashiko et al., Porphyrins, Hydroporphyrins, Azaporphyrins, Phthalocyanines, Corroles, Corrins and Related Macrocycles. *Comprehensive Coordination Chemistry, The Synthesis, Reactions, Properties & Applications of Coordination Compounds*, vol. 2. Wilkinson et al. (Eds.), Pergamon Press, Fairview Pond, NY. 1987. Chpt. 21.1, pp. 813-898.

Mertes et al., Multidentate Macrocyclic and Macropolycyclic Ligands. *Comprehensive Coordination Chemistry, The Synthesis, Reactions, Properties & Applications of Coordination Compounds*, vol. 2. Wilkinson et al. (Eds.), Pergamon Press, Fairview Pond, NY. 1987. Chpt. 21.3, pp. 915-957.

Reedijk, Heterocyclic Nitrogen-donor Ligands. *Comprehensive Coordination Chemistry, The Synthesis, Reactions, Properties & Applications of Coordination Compounds*, vol. 2. Wilkinson et al. (Eds.), Pergamon Press, Fairview Pond, NY. 1987. Chpt. 13.2, pp. 73-98.

Stöllner et al., Membrane-immobilized haptoglobin as affinity matrix for a hemoglobin-A1c immunosensor. Analytica Chimica Acta. Oct. 16, 2002; 470(2):111-9.

\* cited by examiner

Figure 3
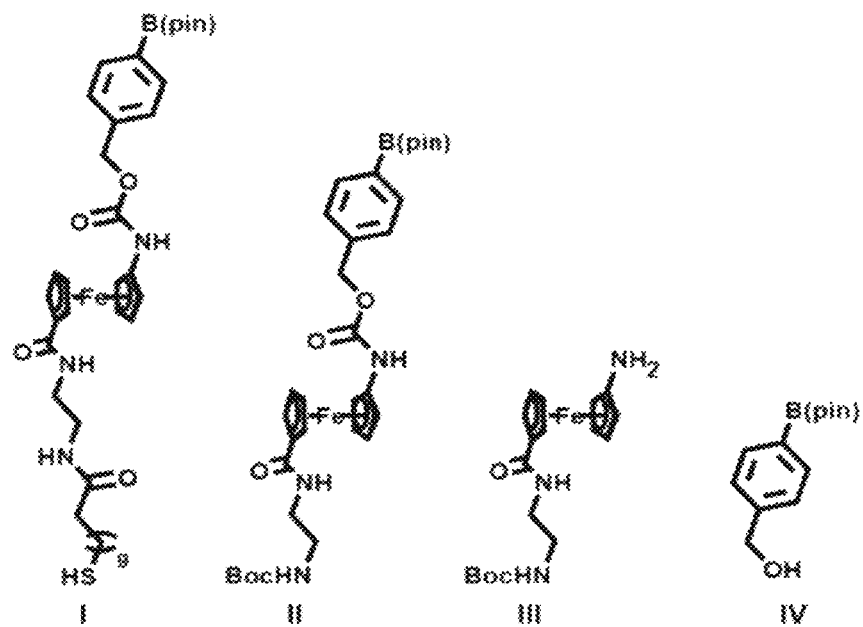
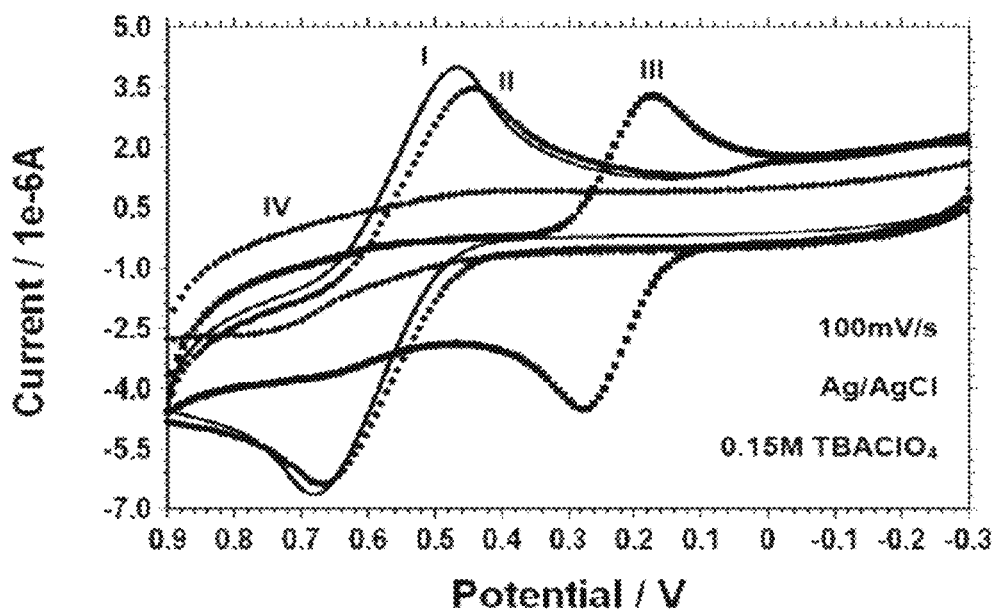

ENZYME TRIGGERED REDOX ALTERING CHEMICAL ELIMINATION (E-TRACE) IMMUNOASSAY

CROSS REFERENCE TO RELATED APPLICATIONS

This application claims the benefit of, and priority to, U.S. Provisional Patent Application No. 61/434,122, filed Jan. 19, 2011, and U.S. Provisional Patent Application No. 61/523,679, filed Aug. 15, 2011, the entire disclosures of which are hereby incorporated by reference in their entirety.

FIELD OF THE INVENTION

The invention relates to novel compositions and methods for the detection of target analytes using change in $E^0$ of a transitional metal complex.

BACKGROUND OF THE INVENTION

Electron transfer reactions are crucial steps in a wide variety of biological transformations ranging from photosynthesis or aerobic respiration. Studies of electron transfer reactions in both chemical and biological systems have led to the development of a large body of knowledge and a strong theoretical base, which describes the rate of electron transfer in terms of a small number of parameters.

Electronic tunneling in proteins and other biological molecules occurs in reactions where the electronic interaction of the redox centers is relatively weak. Semiclassical theory reaction predicts that the reaction rate for electron transfer depends on the driving force ($-\Delta G^\circ$), a nuclear reorganization parameter ($\lambda$), and the electronic-coupling strength between the reactants and products at the transition state ($H_{AB}$), according to the following equation:

$$k_{ET} = (4\pi^3/h^2 \lambda k_B T)^{1/2} (H_{AB})^2 \exp[(-\Delta G^\circ + \lambda)2/\lambda k_B T]$$

The nuclear reorganization energy, $\lambda$, in the equation above is defined as the energy of the reactants at the equilibrium nuclear configuration of the products. For electron transfer reactions in polar solvents, the dominant contribution to $\lambda$ arises from the reorientation of solvent molecules in response to the change in charge distribution of the reactants. The second component of $\lambda$ comes from the changes in bond lengths and angles due to changes in the oxidation state of the donors and acceptors.

Previous work describes using change in reorganization energy, $\lambda$, as the basis of novel sensor. See for example, U.S. Pat. Nos. 6,013,459, 6,013,170, 6,248,229, and 7,267,939, all herein incorporated by reference in their entirety. The methods generally comprise binding an analyte to or near a redox active complex. The redox active complex comprises at least one redox active molecule and a capture ligand which will bind the target analyte, and the complex is bound to an electrode. Upon analyte binding, the reorganization energy of the redox active molecule changes, e.g. the $E^0$ is altered, such that measuring the change in $E^0$ allows the detection of the target analyte.

It is an object of the present invention to provide composition and methods for the detection of target analytes using alteration in the solvent reorganization energy, corresponding to changes in the $E^0$ of redox active molecules.

SUMMARY OF THE INVENTION

The present invention to provide composition and methods for the detection of target analytes using changes in standard potentials of the $E^0$ of redox active molecules upon peroxide-triggered change in the apparent formal potential.

In one aspect, the invention provides compositions and methods for the detection of target analytes in a test sample. Thus, the invention provides a solid support comprising an electrode comprising: a self-assembled monolayer (SAM). (ii) a covalently attached electroactive active moiety (EAM) comprising a transition metal complex comprising a self-immolative moiety (SIM) and a peroxide sensitive moiety (PSM), wherein said EAM has a first $E^0$ and a capture binding ligand that binds the analyte, and a self-assembled monolayer (SAM).

The methods proceed by contacting the target analyte and the solid support, under conditions wherein the target analyte binds the capture binding ligand to form a first complex, and contacting the first complex with a soluble capture ligand that binds the target analyte, wherein the soluble capture ligand comprises a peroxide generating moiety to form a second complex. A peroxide substrate is added to the second complex under conditions that peroxide is generated and the self-immolative moiety is removed such that the EAM has a second $E^0$. The second $E^0$ is then detected as an indication of the presence of said target.

In another aspect, the invention provides methods for detecting a target analyte in a test sample, said method comprising: (a) providing a solid support comprising an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^0$; (iii) a peroxide-generating enzyme that generates peroxide in the presence of a substrate for said peroxide-generating enzyme; (b) contacting said target analyte and said solid support in the presence of an enzyme and an additional substrate for said enzyme, under conditions wherein if said analyte is present, the substrate for said peroxide-generating enzyme is formed, said peroxide is generated and said self-immolative moiety is removed such that said EAM has a second $E^0$; and (c) detecting said second $E^0$ as an indication of the presence of said target analyte.

In another aspect, the invention provides methods for detecting a target analyte in a test sample, said method comprising: (a) providing a solid support comprising an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^0$, (iii) a peroxide generating enzyme that generates peroxide in the presence of said target analyte; (b) contacting said target analyte and said solid support, under conditions wherein said target analyte reacts with said enzyme to generate peroxide and said self-immolative moiety is removed such that said EAM has a second $E^0$; and (c) detecting said second $E^0$ as an indication of the presence of said target analyte.

In another aspect, the invention provides methods for detecting a target analyte in a test sample, said method comprising: (a) providing a solid support comprising an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^0$, (b) contacting said target analyte and said solid support in the presence of an enzyme and optionally an additional substrate for said enzyme, under conditions wherein if said analyte is present a first complex is formed; (c) contacting said first complex with a peroxide generating enzyme under conditions wherein if said first complex is formed, said enzyme is attached to said electrode; (d) providing a substrate for said enzyme such that peroxide is generated and said self-immolative moiety is removed such that said EAM has a second $E^o$; and (e) detecting said second $E^o$ as an indication of the presence of said target analyte.

In another aspect, the invention provides methods for detecting a target analyte in a test sample, said method comprising: (a) providing a solid support comprising an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^o$; (b) contacting said target analyte and said solid support in the presence of an enzyme and an additional substrate for said enzyme, under conditions wherein if said analyte is present, a substrate for a peroxide-generating enzyme is formed; (c) contacting said substrate for a peroxide-generating enzyme with a peroxide generating enzyme under conditions wherein if said substrate for a peroxide-generating enzyme is formed, peroxide is generated and said self-immolative moiety is removed such that said EAM has a second $E^o$; and (d) detecting said second $E^o$ as an indication of the presence of said target analyte.

In another aspect, the invention provides composition comprising a solid support comprising: (a) an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^o$ when said self-immolative moiety is covalently attached to said EAM and a second $E^o$ when said self-immolative moiety is absent; (iii) a peroxide-generating enzyme that generates peroxide in the presence of a substrate for said peroxide-generating enzyme; and (b) a soluble enzyme that generates said substrate for said peroxide-generating enzyme in the presence of a target analyte and an additional substrate or said soluble enzyme.

In another aspect, the invention provides composition comprising a solid support comprising: (a) an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^o$ when said self-immolative moiety is covalently attached to said EAM and a second $E^o$ when said self-immolative moiety is absent; (b) a soluble peroxide-generating enzyme that generates peroxide in the presence of a substrate for said peroxide-generating enzyme; (c) a soluble enzyme that generates said substrate for said peroxide-generating enzyme in the presence of a target analyte and an additional substrate of said soluble enzyme.

In another aspect, the invention provides methods for detecting ATP in a test sample, said method comprising: (a) providing a solid support comprising an electrode comprising: (i) a self-assembled monolayer (SAM), (ii) a covalently attached electroactive active moiety (EAM) comprising a transition metal complex comprising a self-immolative moiety and a peroxide sensitive moiety (PSM), wherein said EAM has a first $E^o$, and (iii) a capture binding ligand that is a substrate of an intermediary enzyme; (b) contacting said test sample and said solid support in the presence of said intermediary enzyme and a first member of a specific binding pair, under conditions wherein if said target analyte is present in said test sample, said intermediary enzyme phosphorylates and conjugates said first member of the specific binding pair to said capture binding ligand to form a first complex; (c) contacting said first complex with a soluble capture ligand that binds said first complex to form a second complex, wherein said soluble capture ligand comprises a peroxide generating moiety; (d) adding a peroxide substrate to said second complex under conditions that peroxide is generated and said self-immolative moiety is removed such that said EAM has a second $E^o$; and (e) detecting said second $E^o$ as an indication of the presence of said ATP.

In one embodiment of the preceding aspect, prior to said step (c), a washing step is performed.

In an embodiment of the preceding aspect and any embodiment thereof, prior to step (d), a washing step is performed.

In an embodiment of the preceding aspect and any embodiment thereof, said intermediary enzyme and said first member of said specific binding is physisorbed onto the onto said SAM. "Physisorbed" as used herein means the enzyme is adsorbed onto the referenced surface (e.g., electrode surface or SAM surface) via non-covalent interactions, such as hydrophobic or ionic interactions.

In an embodiment of the preceding aspect and any embodiment thereof, said solid support comprises an array of electrodes.

In an embodiment of the preceding aspect and any embodiment thereof, said transition metal is selected from the group consisting of iron, ruthenium and osmium.

In an embodiment of the preceding aspect and any embodiment thereof, said EAM is a ferrocene.

In another aspect, the invention provides methods for detecting ATP in a test sample, said method comprising: (a) providing a solid support comprising an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^o$, (b) contacting said test sample and said solid support in the presence of an intermediary enzyme and a substrate of said intermediary enzyme, under conditions wherein if said ATP is present in said test sample, said intermediary enzyme phosphorylates said substrate of said intermediary enzyme to form a peroxide substrate; (c) contacting said peroxide substrate with said peroxide-generating enzyme under conditions that peroxide is generated and said self-immolative moiety is removed such that said EAM has a second $E^o$; and (d) detecting said second $E^o$ as an indication of the presence of said ATP.

In an embodiment of the preceding aspect and any embodiment thereof, prior steps (b) and (c) are carried out simultaneously.

In an embodiment of the preceding aspect and any embodiment thereof, prior wherein said intermediary enzyme is glycerol kinase and said substrate of said intermediary enzyme is glycerol.

In an embodiment of the preceding aspect and any embodiment thereof, prior wherein said peroxide generating moiety is a glycerol-3-phosphate oxidase.

In an embodiment of the preceding aspect and any embodiment thereof, said solid support comprises an array of electrodes.

In an embodiment of the preceding aspect and any embodiment thereof, said transition metal is selected from the group consisting of iron, ruthenium and osmium.

In an embodiment of the preceding aspect and any embodiment thereof, said EAM is a ferrocene.

In another aspect, the invention provides methods for detecting ATP in a test sample, said method comprising: (a) providing a solid support comprising an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^0$; and (iii) a peroxide-generating enzyme; (b) contacting said test sample and said solid support in the presence of an intermediary enzyme and a substrate of said intermediary enzyme, wherein said ATP is a co-factor of said intermediary enzyme, under conditions wherein if said ATP is present in said test sample, said intermediary enzyme phosphorylates said substrate of said intermediary enzyme to form a substrate of said peroxide-generating enzyme; (c) contacting said substrate of said peroxide-generating enzyme with said peroxide-generating enzyme under conditions that peroxide is generated and said self-immolative moiety is removed such that said EAM has a second $E^0$; and (d) detecting said second $E^0$ as an indication of the presence of said ATP.

In an embodiment of the preceding aspects, prior steps (b) and (c) are carried out separately.

In an embodiment of the preceding aspect and any embodiment thereof, prior steps (b) and (c) are carried out simultaneously.

In an embodiment of the preceding aspect and any embodiment thereof, prior wherein said intermediary enzyme is glycerol kinase and said substrate of said intermediary enzyme is glycerol.

In an embodiment of the preceding aspect and any embodiment thereof, prior wherein said peroxide generating moiety is a glycerol-3-phosphate oxidase.

In an embodiment of the preceding aspect and any embodiment thereof, said solid support comprises an array of electrodes.

In an embodiment of the preceding aspect and any embodiment thereof, said transition metal is selected from the group consisting of iron, ruthenium and osmium.

In an embodiment of the preceding aspect and any embodiment thereof, said EAM is a ferrocene.

In another aspect, the invention provides compositions comprising a solid support comprising: (a) an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^0$ when said self-immolative moiety is covalently attached to said EAM and a second $E^0$ when said self-immolative moiety is absent; (iii) a capture binding ligand comprising a substrate of an ATP-dependent intermediary enzyme; and (d) a soluble capture ligand comprising a peroxide generating moiety.

In another aspect, the invention provides compositions comprising a solid support comprising: (a) an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^0$ when said self-immolative moiety is covalently attached to said EAM and a second $E^0$ when said self-immolative moiety is absent; and (iii) a peroxide generating enzyme.

In another aspect, the invention provides methods for detecting a target analyte in a test sample, said method comprising: (a) providing a solid support comprising an electrode comprising: (i) a self-assembled monolayer (SAM), (ii) a covalently attached electroactive active moiety (EAM) comprising a transition metal complex comprising a self-immolative moiety and a peroxide sensitive moiety (PSM), wherein said EAM has a first $E^0$, and (b) contacting said target analyte and said solid support under conditions wherein said target analyte reacts with a peroxide generating enzyme to generate peroxide and said self-immolative moiety is removed such that said EAM has a second $E^0$ test sample; and (c) detecting said second $E^0$ as an indication of the presence of said target analyte.

In another aspect, the invention provides methods for detecting a target analyte in a test sample, said method comprising: (a) providing a solid support comprising an electrode comprising: (i) a self-assembled monolayer (SAM), (ii) a covalently attached electroactive active moiety (EAM) comprising a transition metal complex comprising a self-immolative moiety and a peroxide sensitive moiety (PSM), wherein said EAM has a first $E^0$, and (b) contacting said target analyte and said solid support in the presence of an intermediary enzyme and optionally an additional substrate for said enzyme, under conditions wherein if said analyte is present, the target analyte and said optional additional substrate reacts with the intermediary enzyme to form a first complex; (c) contacting said first complex with said peroxide generating enzyme under conditions wherein if said first complex is formed, said first complex reacts with said peroxide generating enzyme to generate peroxide and said self-immolative moiety is removed such that said EAM has a second $E^0$ test sample; and (d) detecting said second $E^0$ as an indication of the presence of said target analyte.

In an embodiment of either of the two previous aspects, said peroxide generating enzyme is immobilized or physisorbed onto the solid support, the electrode, or SAM.

In an embodiment of either of the two previous aspects, and any embodiment thereof, said intermediary enzyme is immobilized or physisorbed onto the solid support, the electrode, or SAM.

In an embodiment of either of the two previous aspects, and any embodiment thereof, wherein steps (b) and (c) are carried out separately.

In an embodiment of either of the two previous aspects, and any embodiment thereof, steps (b) and (c) are carried out simultaneously.

In an embodiment of either of the two previous aspects, and any embodiment thereof, said target analyte is ATP, said intermediary enzyme is glycerol kinase and said substrate of said intermediary enzyme is glycerol, and said peroxide generating moiety is glycerol-3-oxidase.

In an embodiment of either of the two previous aspects, and any embodiment thereof, said target analyte is NADH and said peroxide generating moiety is NADH oxidase (NAOX).

In an embodiment of either of the two previous aspects, and any embodiment thereof, said solid support comprises an array of electrodes.

In an embodiment of either of the two previous aspects, and any embodiment thereof, said transition metal is selected from the group consisting of iron, ruthenium and osmium.

In an embodiment of either of the two previous aspects, and any embodiment thereof, said EAM is a ferrocene.

In an embodiment of either of the two previous aspects, and any embodiment thereof, said detecting is done amperometrically at each first and second $E^0$.

In another aspect, the invention provides compositions comprising a solid support comprising: (a) an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^0$ when said self-immolative moiety is covalently attached to said EAM and a second $E^0$ when said self-immolative moiety is absent; (iii) a capture binding ligand comprising a substrate of an ATP-dependent intermediary enzyme; and (d) a soluble capture ligand comprising a peroxide generating moiety.

In another aspect, the invention provides compositions comprising a solid support comprising: (a) an electrode comprising: (i) a self-assembled monolayer (SAM); (ii) a covalently attached electroactive active moiety (EAM) comprising a transition metal complex comprising a self-immolative moiety and a peroxide sensitive moiety (PSM), wherein said EAM has a first $E^0$ when said self-immolative moiety is covalently attached to said EAM and a second $E^0$ when said self-immolative moiety is absent; and (iii) a peroxide generating enzyme.

BRIEF DESCRIPTION OF THE DRAWINGS

FIG. 3. Solution CV data for EAM 1 and a control compound following $H_2O_2$ induced cleavage of the POM ligand. The change in $E^0$ following the self-immolative process is 331 mV. Experiments were run in THF with TBAClO$_4$ (150 mM) supporting electrolyte using a carbon working electrode, Ag/AgCl reference electrode, and a Pt wire counter electrode.

FIG. 8A depicts a first type of self-immolative moiety, which relies on the PSM contributing an —OH group upon contact with peroxide, resulting a phenol-based linker that releases from the EAM. n can be an integer of 1 or higher, with from 1 to 5 finding particular use in the invention. m is an integer of at least one; as will be appreciated by those in the art, m will depend on the transitional metal complex used and the number of positions in the EAM; for example, when a metallocene such as ferrocene is used, there can be up to 5 PSM-SIMs per cyclopentadienyl ring, with at least one of the positions on one of the rings being used for attachment to the electrode. FIGS. 8B, 8C and 8D show multimers of SIMs. X can be —NH— or —O—.

FIG. 13B depicts that BirA catalyzes the biotinlyation of the A. After washing, a glucose oxidase-streptavidin conjugate is further conjugated to the biotin attached to the AP. FIG. 13C depicts the reaction when glucose is added and the peroxide generated reacts with the EAMs with the self-immolative moiety, resulting in a change in the $E^0$.

DETAILED DESCRIPTION OF THE INVENTION

Figure 1:
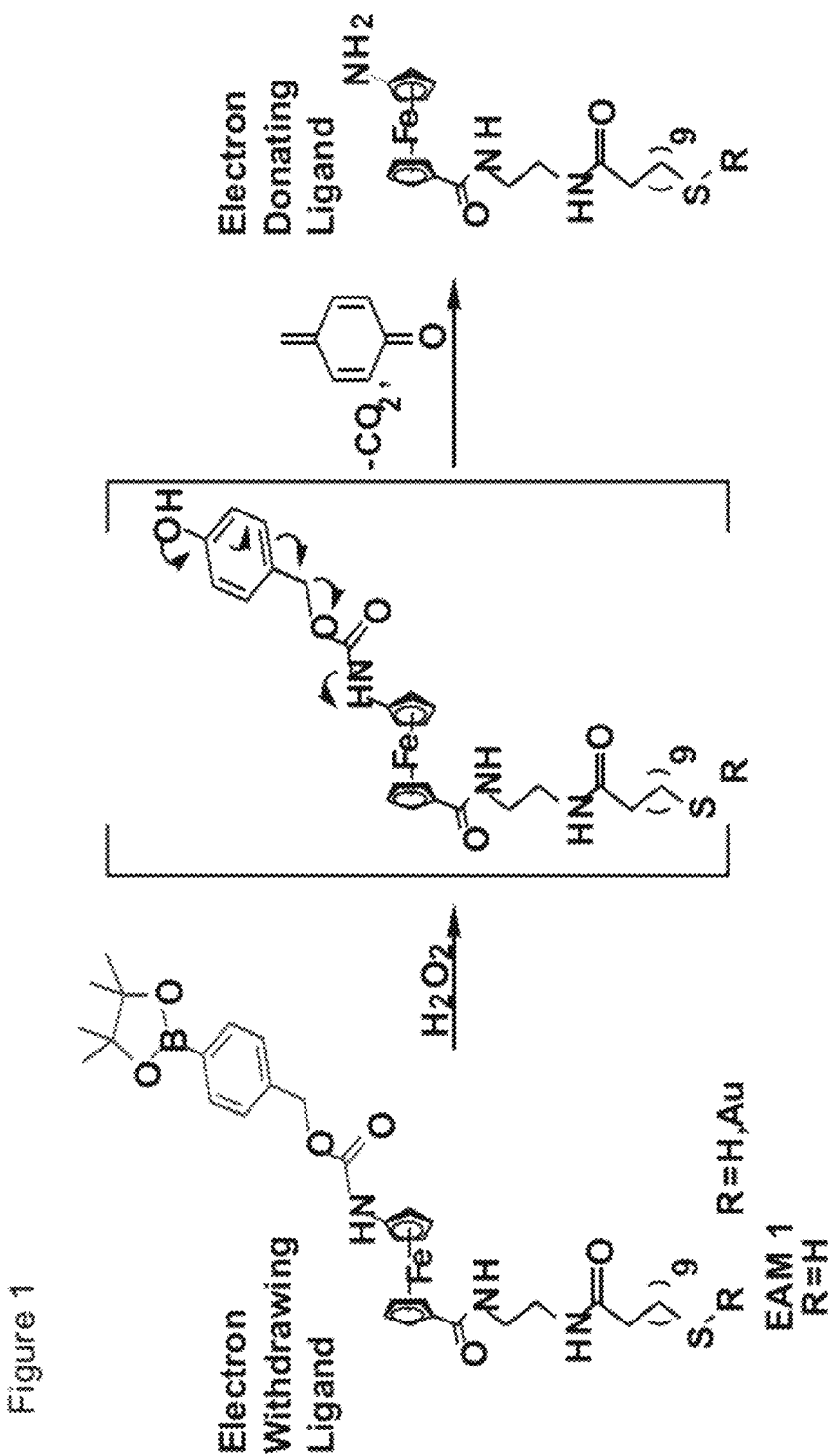
FIG. 1. Structure of electroactive molecule (EAM) 1 and mechanism of peroxide-induced ligand dissociation. The change in ligand electronics is responsible for the shift in redox potential.
Figure 2:
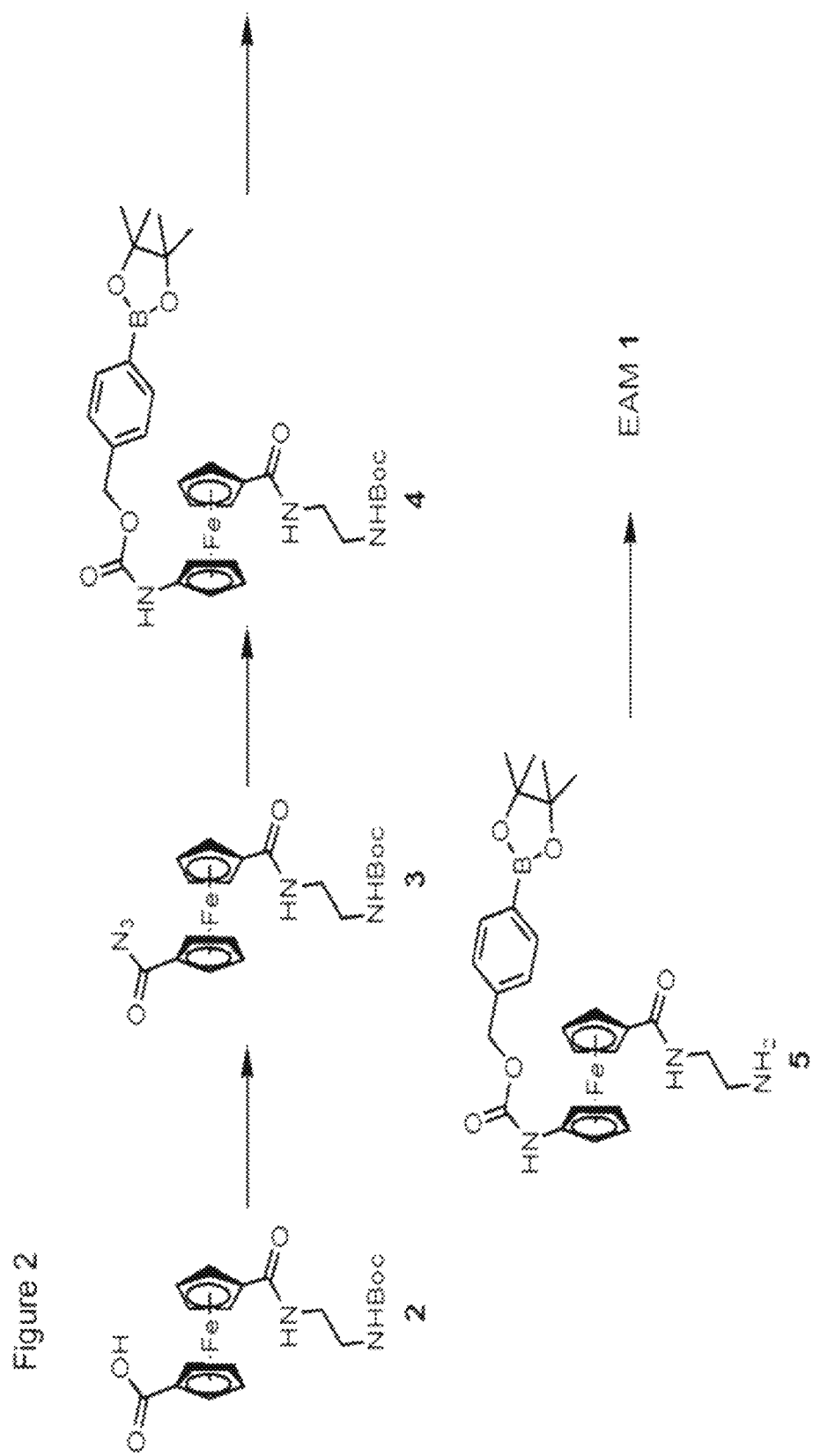
FIG. 2. The synthetic scheme of one of the embodiments of the invention as depicted in FIG. 1.

U.S. patent application Ser. Nos. 12/253,828, 12/253,875, 12/853,204, 61/332,565, 61/347,121, 61/394,458, 61/366,013 and 61/407,828 are all incorporated by reference in their entirety.

Overview

The present invention is directed to electronic methods of detecting target analytes such that upon binding of the target analyte a shift in electrochemical potential is seen. This mechanism has been generally described in U.S. Pat. Nos. 7,595,153, 7,759,073 and 7,713,711, and U.S. patent application Ser. No. 12/253,828, filed Oct. 17, 2008; U.S. patent application Ser. No. 12/253,875, filed Oct. 17, 2008; U.S. Provisional Patent Application No. 61/332,565, filed May 7, 2010; U.S. Provisional Patent Application No. 61/347,121, filed May 21, 2010; and U.S. Provisional Patent Application No. 61/366,013, filed Jul. 20, 2010, all of which are expressly incorporated by reference in their entirety.

The assay relies on the use of an electroactive moiety ("EAM"), which is attached to the electrode and comprises a self-immolative moiety, whose presence gives the EAM a first $E^0$, whose absence, upon irreversible cleavage, gives the EAM a second $E^0$. The electrode also contains capture binding ligands that will bind the target analyte upon its introduction. A soluble capture ligand is introduced, which also binds the target analyte and comprises a peroxide generating moiety, such as a glucose oxidase enzyme. Upon the addition of oxygen and a substrate for the peroxidase generating moiety (e.g. an oxygen saturated buffer and glucose, in the case of a glucose oxidase enzyme as the peroxidase generating moiety) peroxide is generated, attacking the self-immolative moiety and causing the removal of the self-immolative moiety from the EAM, which results in a change in the $E^0$ of the EAM. This difference is detected, and if such a change occurs, it is an indication of the presence of the target analyte.

Thus, to determine whether a target analyte is present in the sample, the sample is applied to the detection electrode surface, optionally washed, and an oxidase enzyme-conjugated secondary binding ligand (for example, an antibody) that binds an alternative epitope of the target analyte is added, creating a "sandwich assay" format with the target. The surface is optionally washed, and treated with an oxygen-saturated buffer containing a high concentration of glucose. The presence of the substrate oxidase enzyme (sometimes referred to herein as "SOX") on the surface results in the enzymatic creation of hydrogen peroxide in solution which diffuses to the monolayer surface and triggers a chemical elimination reaction ("self-immolative" reaction) in the immobilized EAMs. This irreversible elimination reaction changes the electronic environment of the EAM, for example by altering the "R" groups (e.g. substituent groups) of the transition metal complex, thus shifting the apparent formal potential of the EAM to a second $E^0$ to signal the presence of the target.

In other aspects, the target analyte may be a substrate for an intermediary enzyme and an optional additional substrate which ultimately generates a substrate for a peroxide generating moiety. Examples of such substrates include, but are not limited to, ATP and NADH. For example, ATP is a substrates for an intermediary enzyme such as, but not limited to, biotin ligase (BirA) and glycerol kinase (GK) which utilize ATP as a substrate to phosphorylate their respective acceptor protein and glycerol substrates. An "intermediary enzyme" as used herein, refers to an enzyme that utilizes a target analytes as a substrate.

Accordingly, the present invention provides methods and compositions for detecting target analytes in samples.

Target Analytes

By "target analyte" or "analyte" or grammatical equivalents herein is meant any molecule, compound or particle to be detected. Target analytes bind to binding ligands (both capture and soluble binding ligands), as is more fully described below. As will be appreciated by those in the art, a large number of analytes may be detected using the present methods; basically, any target analyte for which a binding ligand, described below, may be made may be detected using the methods of the invention.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc.

In some embodiments, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L configuration. As discussed below, when the protein is used as a binding ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella zoster virus, cytomegalovirus, Epstein Barr virus), rotaviruses, Norwalk viruses, hantavirus, arenavirus, rhabdovirus (e.g. rabies virus), retroviruses (including HIV, HTLV I and II), papovaviruses (e.g. papillomavirus), polyomaviruses, and picornaviruses, and the like), and bacteria (including a wide variety of pathogenic and non pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cotrisol, estradiol, follicle stimulating hormone (FSH), thyroid-stimulating hormone (TSH), leutinzing hormone (LH), progeterone, testosterone,; and (4) other proteins (including α-fetoprotein, carcinoembryonic antigen CEA.

In addition, any of the biomolecules for which antibodies may be detected may be detected directly as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

Target analytes including troponin and HbA1c find use in particular embodiments and applications. For HbA1c, one of the binding ligands, either the capture binding ligand or the soluble binding ligand has specificity for the glycated form of hemoglobin. That is, in one embodiment, the capture binding ligand can bind either form of hemoglobin; after washing the surface, a soluble binding ligand that has specificity only for the glycosylated form (e.g. HbA1c) with the peroxide-generating moiety is added. Alternatively, the capture binding ligand has specificity for Hb1Ac over other forms of hemoglobin, and a soluble capture ligand without such specificity can be used after appropriate washing of the surface. This approach can be used for other target analytes where detection of either the glycosylated or nonglycosylated form is desired. As will be appreciated by those in the art, there are also target analytes for which detection of both forms is desired, and in those embodiments, using binding ligands that do not have specificity for one or the other is used.

Of particular interest in the present invention are assays for *Staphylococcus* enterotoxin B, P-Selectin, D-dimer, B-Type Natriuretic Peptide (BNP), C Reactive Protein, Myoglobin and CK-MB.

In some embodiments, as outlined herein, any number of different enzyme substrates, including metabolites, can serve as target analytes. For example, ATP and/or NADH, can be detected and/or quantified using the systems herein. In addition, other enzyme substrates for which peroxide-generating enzymes exist can be detected using the general mechanisms as outlined herein, including, but not limited to, NADH, glucose, sucrose, lactose, lactate, galactose, glutamate, choline, ethanol, creatinine, etc.

Samples

The target analytes are generally present in samples. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples, purified samples, raw samples, etc.; as will be appreciated by those in the art, virtually any experimental manipulation may have been done on the sample. Some embodiments utilize target samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to storable or archival tissue samples. Most patient-derived pathological samples are routinely fixed and paraffin-embedded to allow for histological analysis and subsequent archival storage.

Solid Supports

The target analytes are detected using solid supports comprising electrodes. By "substrate" or "solid support" or other grammatical equivalents herein is meant any material that can be modified to contain discrete individual sites appropriate of the attachment or association of capture ligands. Suitable substrates include metal surfaces such as gold, electrodes as defined below, glass and modified or functionalized glass, fiberglass, teflon, ceramics, mica, plastic (including acrylics, polystyrene and copolymers of styrene and other materials, polypropylene, polyethylene, polybutylene, polyimide, polycarbonate, polyurethanes, Teflon™ and derivatives thereof, etc.), GETEK (a blend of polypropylene oxide and fiberglass), etc, polysaccharides, nylon or nitrocellulose, resins, silica or silica-based materials including silicon and modified silicon, carbon, metals, inorganic glasses and a variety of other polymers, with printed circuit board (PCB) materials being particularly preferred.

The present system finds particular utility in array formats, i.e. wherein there is a matrix of addressable detection electrodes (herein generally referred to "pads", "addresses" or "micro-locations"). By "array" herein is meant a plurality of capture ligands in an array format; the size of the array will depend on the composition and end use of the array. Arrays containing from about 2 different capture substrates to many thousands can be made.

In a preferred embodiment, the detection electrodes are formed on a substrate. In addition, the discussion herein is generally directed to the use of gold electrodes, but as will be appreciated by those in the art, other electrodes can be used as well. The substrate can comprise a wide variety of materials, as outlined herein and in the cited references.

In general, preferred materials include printed circuit board materials. Circuit board materials are those that comprise an insulating substrate that is coated with a conducting layer and processed using lithography techniques, particularly photolithography techniques, to form the patterns of electrodes and interconnects (sometimes referred to in the art as interconnections or leads). The insulating substrate is generally, but not always, a polymer. As is known in the art, one or a plurality of layers may be used, to make either "two dimensional" (e.g. all electrodes and interconnections in a plane) or "three dimensional" (wherein the electrodes are on one surface and the interconnects may go through the board to the other side or wherein electrodes are on a plurality of surfaces) boards. Three dimensional systems frequently rely on the use of drilling or etching, followed by electroplating with a metal such as copper, such that the "through board" interconnections are made. Circuit board materials are often provided with a foil already attached to the substrate, such as a copper foil, with additional copper added as needed (for example for interconnections), for example by electroplating. The copper surface may then need to be roughened, for example through etching, to allow attachment of the adhesion layer.

Accordingly, in a preferred embodiment, the present invention provides biochips (sometimes referred to herein "chips") that comprise substrates comprising a plurality of electrodes, preferably gold electrodes. The number of electrodes is as outlined for arrays. Each electrode preferably comprises a self-assembled monolayer as outlined herein. In a preferred embodiment, one of the monolayer-forming species comprises a capture ligand as outlined herein. In addition, each electrode has an interconnection that is attached to the electrode at one end and is ultimately attached to a device that can control the electrode. That is, each electrode is independently addressable.

Finally, the compositions of the invention can include a wide variety of additional components, including microfluidic components and robotic components (see for example U.S. Pat. Nos. 6,942,771 and 7,312,087 and related cases, both of which are hereby incorporated by reference in its entirety), and detection systems including computers utilizing signal processing techniques (see for example U.S. Pat. No. 6,740,518, hereby incorporated by reference in its entirety).

Electrodes

The solid supports of the invention comprise electrodes. By "electrodes" herein is meant a composition, which, when connected to an electronic device, is able to sense a current or charge and convert it to a signal. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes, with gold being particularly preferred.

The electrodes described herein are depicted as a flat surface, which is only one of the possible conformations of the electrode and is for schematic purposes only. The conformation of the electrode will vary with the detection method used.

The electrodes of the invention are generally incorporated into biochip cartridges and can take a wide variety of configurations, and can include working and reference electrodes, interconnects (including "through board" interconnects), and microfluidic components. See for example U.S. Pat. No. 7,312,087, incorporated herein by reference in its entirety. In addition, the biochips generally include a working electrode with the components described herein, a reference electrode, and a counter/auxiliary electrode.

The biochip cartridges include substrates comprising the arrays of biomolecules, and can be configured in a variety of ways. For example, the chips can include reaction chambers with inlet and outlet ports for the introduction and removal of reagents. In addition, the cartridges can include caps or lids that have microfluidic components, such that the sample can be introduced, reagents added, reactions done, and then the sample is added to the reaction chamber comprising the array for detection.

Self Assembled Monolayers

The electrodes comprise a self assembled monolayer ("SAM"). By "monolayer" or "self-assembled monolayer" or "SAM" herein is meant a relatively ordered assembly of molecules spontaneously chemisorbed on a surface, in which the molecules are oriented approximately parallel to each other and roughly perpendicular to the surface. Each of the molecules includes a functional group that adheres to the surface, and a portion that interacts with neighboring molecules in the monolayer to form the relatively ordered array. A "mixed" monolayer comprises a heterogeneous monolayer, that is, where at least two different molecules make up the monolayer. As outlined herein, the use of a monolayer reduces the amount of non-specific binding of biomolecules to the surface, and, in the case of nucleic acids, increases the efficiency of oligonucleotide hybridization as a result of the distance of the oligonucleotide from the electrode. Thus, a monolayer facilitates the maintenance of the target enzyme away from the electrode surface. In addition, a monolayer serves to keep charge carriers away from the surface of the electrode. Thus, this layer helps to prevent electrical contact between the electrodes and the ReAMs, or between the electrode and charged species within the solvent. Such contact can result in a direct "short circuit" or an indirect short circuit via charged species which may be present in the sample. Accordingly, the monolayer is preferably tightly packed in a uniform layer on the electrode surface, such that a minimum of "holes" exist. The monolayer thus serves as a physical barrier to block solvent accessibility to the electrode.

In some embodiments, the monolayer comprises conductive oligomers, and in particular, conductive oligomers are generally used to attach the EAM to the electrode surface, as described below. By "conductive oligomer" herein is meant a substantially conducting oligomer, preferably linear, some embodiments of which are referred to in the literature as "molecular wires". By "substantially conducting" herein is meant that the oligomer is capable of transferring electrons at 100 Hz. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to inject or receive electrons into or from an associated EAM. Furthermore, the conductive oligomer is more conductive than the insulators as defined herein. Additionally, the conductive oligomers of the invention are to be distinguished from electroactive polymers, that themselves may donate or accept electrons.

A more detailed description of conductive oligomers is found in WO/1999/57317, herein incorporated by reference in its entirety. In particular, the conductive oligomers as shown in Structures 1 to 9 on page 14 to 21 of WO/1999/57317 find use in the present invention. In some embodiments, the conductive oligomer has the following structure:

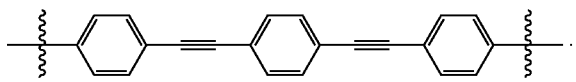

In addition, the terminus of at least some of the conductive oligomers in the monolayer is electronically exposed. By "electronically exposed" herein is meant that upon the placement of an EAM in close proximity to the terminus, and after initiation with the appropriate signal, a signal dependent on the presence of the EAM may be detected. The conductive oligomers may or may not have terminal groups. Thus, in a preferred embodiment, there is no additional terminal group, and the conductive oligomer terminates with a terminal group; for example, such as an acetylene bond. Alternatively, in some embodiments, a terminal group is added, sometimes depicted herein as "Q". A terminal group may be used for several reasons; for example, to contribute to the electronic availability of the conductive oligomer for detection of EAMs, or to alter the surface of the SAM for other reasons, for example to prevent non-specific binding. For example, there may be negatively charged groups on the terminus to form a negatively charged surface such that when the target analyte is nucleic acid such as DNA or RNA, the nucleic acid is repelled or prevented from lying down on the surface, to facilitate hybridization. Preferred terminal groups include —NH, —OH, —COOH, and alkyl groups such as —CH$_3$, and (poly)alkyloxides such as (poly)ethylene glycol, with —OCH$_2$CH$_2$OH, —(OCH$_2$CH$_2$O)$_2$H, —(OCH$_2$CH$_2$O)$_3$H, and —(OCH$_2$CH$_2$O)$_4$H being preferred.

In one embodiment, it is possible to use mixtures of conductive oligomers with different types of terminal groups. Thus, for example, some of the terminal groups may facilitate detection, and some may prevent non-specific binding.

In some embodiments, the electrode further comprises a passivation agent, preferably in the form of a monolayer on the electrode surface. For some analytes the efficiency of analyte binding (i.e. hybridization) may increase when the binding ligand is at a distance from the electrode. In addition, the presence of a monolayer can decrease non-specific binding to the surface (which can be further facilitated by the use of a terminal group, outlined herein. A passivation agent layer facilitates the maintenance of the binding ligand and/or analyte away from the electrode surface. In addition, a passivation agent serves to keep charge carriers away from the surface of the electrode. Thus, this layer helps to prevent electrical contact between the electrodes and the electron transfer moieties, or between the electrode and charged species within the solvent. Such contact can result in a direct "short circuit" or an indirect short circuit via charged species which may be present in the sample. Accordingly, the monolayer of passivation agents is preferably tightly packed in a uniform layer on the electrode surface, such that a minimum of "holes" exist. Alternatively, the passivation agent may not be in the form of a monolayer, but may be present to help the packing of the conductive oligomers or other characteristics.

The passivation agents thus serve as a physical barrier to block solvent accessibility to the electrode. As such, the passivation agents themselves may in fact be either (1) conducting or (2) nonconducting, i.e. insulating, molecules. Thus, in one embodiment, the passivation agents are conductive oligomers, as described herein, with or without a terminal group to block or decrease the transfer of charge to the electrode. Other passivation agents which may be conductive include oligomers of —(CF$_2$)$_n$—, —(CHF)$_n$— and —(CFR)$_n$—. In a preferred embodiment, the passivation agents are insulator moieties.

In some embodiments, the monolayers comprise insulators. An "insulator" is a substantially nonconducting oligomer, preferably linear. By "substantially nonconducting" herein is meant that the rate of electron transfer through the insulator is slower than the rate of electron transfer through the conductive oligomer. Stated differently, the electrical resistance of the insulator is higher than the electrical resistance of the conductive oligomer. It should be noted however that even oligomers generally considered to be insulators, such as —(CH$_2$)$_{16}$ molecules, still may transfer electrons, albeit at a slow rate.

In some embodiments, the insulators have a conductivity, S, of about $10^{-7}\Omega^{-1}$ cm$^{-1}$ or lower, with less than about $10^{-8}\Omega^{-1}$ cm$^{-1}$ being preferred. Gardner et al., Sensors and Actuators A 51 (1995) 57-66, incorporated herein by reference.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer. In some embodiments the insulator comprises C$_6$-C$_{16}$ alkyl.

The passivation agents, including insulators, may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. In addition, the terminus of the passivation agent, including insulators, may contain an additional group to influence the exposed surface of the monolayer, sometimes referred to herein as a terminal group ("TG"). For example, the addition of charged, neutral or hydrophobic groups may be done to inhibit non-specific binding from the sample, or to influence the kinetics of binding of the analyte, etc. For example, there may be charged groups on the terminus to form a charged surface to encourage or discourage binding of certain target analytes or to repel or prevent from lying down on the surface.

The length of the passivation agent will vary as needed. Generally, the length of the passivation agents is similar to the length of the conductive oligomers, as outlined above. In addition, the conductive oligomers may be basically the same length as the passivation agents or longer than them, resulting in the binding ligands being more accessible to the solvent.

The monolayer may comprise a single type of passivation agent, including insulators, or different types.

Suitable insulators are known in the art, and include, but are not limited to, —(CH$_2$)$_n$—, —(CRH)$_n$—, and —(CR$_2$)$_n$—, ethylene glycol or derivatives using other heteroatoms in place of oxygen, i.e. nitrogen or sulfur (sulfur derivatives are not preferred when the electrode is gold). In some embodiments, the insulator comprises C$_6$ to C$_{16}$ alkyl.

In some embodiments, the electrode is a metal surface and need not necessarily have interconnects or the ability to do electrochemistry.

Electroactive Moieties

In addition to the SAMs, the electrodes comprise an EAM. By "electroactive moiety (EAM)" or "transition metal complex" or "redox active molecule" or "electron transfer moiety (ETM)" herein is meant a metal-containing compound which is capable of reversibly or semi-reversibly transferring one or more electrons. It is to be understood that electron donor and acceptor capabilities are relative; that is, a molecule which can lose an electron under certain experimental conditions will be able to accept an electron under different experimental conditions.

It is to be understood that the number of possible transition metal complexes is very large, and that one skilled in the art of electron transfer compounds will be able to utilize a number of compounds in the present invention. By "transitional metal" herein is meant metals whose atoms have a partial or completed shell of electrons. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinum (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, find particular use in the present invention. Metals that find use in the invention also are those that do not change the number of coordination sites upon a change in oxidation state, including ruthenium, osmium, iron, platinum and palladium, with osmium, ruthenium and iron being especially useful. Generally, transition metals are depicted herein (or in incorporated references) as "TM" or "M".

The transitional metal and the coordinating ligands form a metal complex. By "ligand" or "coordinating ligand" (depicted herein or in incorporated references in the figures as "L") herein is meant an atom, ion, molecule, or functional group that generally donates one or more of its electrons through a coordinate covalent bond to, or shares its electrons through a covalent bond with, one or more central atoms or ions.

In some embodiments, small polar ligands are used; suitable small polar ligands, generally depicted herein as "L", fall into two general categories, as is more fully described herein. In one embodiment, the small polar ligands will be effectively irreversibly bound to the metal ion, due to their characteristics as generally poor leaving groups or as good sigma donors, and the identity of the metal. These ligands may be referred to as "substitutionally inert". Alternatively, as is more fully described below, the small polar ligands may be reversibly bound to the metal ion, such that upon binding of a target analyte, the analyte may provide one or more coordination atoms for the metal, effectively replacing the small polar ligands, due to their good leaving group properties or poor sigma donor properties. These ligands may be referred to as "substitutionally labile". The ligands preferably form dipoles, since this will contribute to a high solvent reorganization energy.

Some of the structures of transitional metal complexes are shown below:

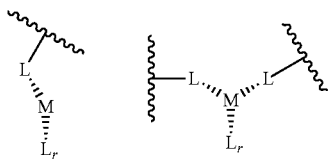

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the nucleic acid, and r, add up to six. Thus, when the metal has a coordination number of six, r may range from zero (when all coordination atoms are provided by the other two ligands) to four, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand attached to the nucleic acid are at least bidentate; that is, r is preferably zero, one (i.e. the remaining co-ligand is bidentate) or two (two monodentate co-ligands are used).

As will be appreciated in the art, the co-ligands can be the same or different. Suitable ligands fall into two categories: ligands which use nitrogen, oxygen, sulfur, carbon or phosphorus atoms (depending on the metal ion) as the coordination atoms (generally referred to in the literature as sigma ($\sigma$) donors) and organometallic ligands such as metallocene ligands (generally referred to in the literature as pi ($\pi$) donors, and depicted herein as $L_m$). Suitable nitrogen donating ligands are well known in the art and include, but are not limited to, cyano (C=N), $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

As will be appreciated in the art, any ligand donor(1)-bridge-donor(2) where donor (1) binds to the metal and donor (2) is available for interaction with the surrounding medium (solvent, protein, etc.) can be used in the present invention, especially if donor(1) and donor(2) are coupled through a pi system, as in cyanos (C is donor(1), N is donor(2), pi system is the CN triple bond). One example is bipyrimidine, which looks much like bipyridine but has N donors on the "back side" for interactions with the medium. Additional co-ligands include, but are not limited to cyanates, isocyanates (—N=C=O), thiocyanates, isonitrile, $N_2$, $O_2$, carbonyl, halides, alkoxyide, thiolates, amides, phosphides, and sulfur containing compound such as sulfino, sulfonyl, sulfoamino, and sulfamoyl.

In some embodiments, multiple cyanos are used as co-ligand to complex with different metals. For example, seven cyanos bind Re(III); eight bind Mo(IV) and W(IV). Thus at Re(III) with 6 or less cyanos and one or more L, or Mo(IV) or W(IV) with 7 or less cyanos and one or more L can be used in the present invention. The EAM with W(IV) system has particular advantages over the others because it is more inert, easier to prepare, more favorable reduction potential. Generally that a larger CN/L ratio will give larger shifts.

Suitable sigma donating ligands using carbon, oxygen, sulfur and phosphorus are known in the art. For example, suitable sigma carbon donors are found in Cotton and Wilkinson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkinson.

The oxygen, sulfur, phosphorus and nitrogen-donating ligands are attached in such a manner as to allow the heteroatoms to serve as coordination atoms.

In some embodiments, organometallic ligands are used. In addition to purely organic compounds for use as redox moieties, and various transition metal coordination complexes with δ-bonded organic ligand with donor atoms as heterocyclic or exocyclic substituents, there is available a wide variety of transition metal organometallic compounds with π-bonded organic ligands (see Cotton & Wilkinson, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5]^{(-1)}$ and various ring substituted and ring fused derivatives, such as the indenylide (−1) ion, that yield a class of bis(cyclopentadieyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene $[(C_5H_5)_2Fe]$ and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties that are covalently attached to either the ribose ring or the nucleoside base of nucleic acid. Other potentially suitable organometallic ligands include cyclic arenes such as benzene, to yield bis(arene)metal compounds and their ring substituted and ring fused derivatives, of which bis(benzene) chromium is a prototypical example. Other acyclic π-bonded ligands such as the allyl(−1) ion, or butadiene yield potentially suitable organometallic compounds, and all such ligands, in conduction with other .pi.-bonded and .delta.- bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties in nucleic acid analysis.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkinson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the nucleic acid is a nitrogen donating ligand, with the other ligands, if needed, are either nitrogen donating ligands or metallocene ligands, or a mixture.

As a general rule, EAM comprising non-macrocyclic chelators are bound to metal ions to form non-macrocyclic chelate compounds, since the presence of the metal allows for multiple proligands to bind together to give multiple oxidation states.

In some embodiments, nitrogen donating proligands are used. Suitable nitrogen donating proligands are well known in the art and include, but are not limited to, $NH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. It should be noted that macrocylic ligands that do not coordinatively saturate the metal ion, and which require the addition of another proligand, are considered non-macrocyclic for this purpose. As will be appreciated by those in the art, it is possible to covalent attach a number of "non-macrocyclic" ligands to form a coordinatively saturated compound, but that is lacking a cyclic skeleton.

In some embodiments, a mixture of monodentate (e.g. at least one cyano ligand), bi-dentate, tri-dentate, and polydentate ligands can be used in the construction of EAMs.

Of particular use in the present invention are EAMs that are metallocenes, and in particular ferrocenes, which have at least a first self-immolative moiety attached, although in some embodiments, more than one self-immolative moiety is attached as is described below (it should also be noted that other EAMs, as are broadly described herein, with self-immolative moieties can also be used). In some embodiments, when more than one self-immolative moiety is attached to a ferrocene, they are all attached to one of the cyclopentydienyl rings. In some embodiments, the self-immolative moieties are attached to different rings. In some embodiments, it is possible to saturate one or both of the cyclopentydienyl rings with self-immolative moieties, as long as one site is used for attachment to the electrode.

In addition, EAMs generally have an attachment moiety for attachment of the EAM to the conductive oligomer which is used to attach the EAM to the electrode. In general, although not required, in the case of metallocenes such as ferrocenes, the self-immolative moiety(ies) are attached to one of the cyclopentydienyl rings, and the attachment moiety is attached to the other ring, as is generally depicted in FIG. 1, although attachment to the same ring can also be done. As will be appreciated by those in the art, any combination of self-immolative moieties and at least one attachment linker can be used, and on either ring.

In addition to the self-immolative moiety(ies) and the attachment moiety(ies), the ferrocene can comprise additional substituent groups, which can be added for a variety of reasons, including altering the $E^0$ in the presence or absence of at least the self-immolative group. Suitable substituent groups, frequently depicted in associated and incorporated references as "R" groups, are recited in U.S. patent application Ser. No. 12/253,828, filed Oct. 17, 2008; U.S. patent application Ser. No. 12/253,875, filed Oct. 17, 2008; U.S. Provisional Patent Application No. 61/332,565, filed May 7, 2010; U.S. Provisional Patent Application No. 61/347,121, filed May 21, 2010; and U.S. Provisional Patent Application No. 61/366,013, filed Jul. 20, 2010, hereby incorporated by reference.

In some embodiments, such as depicted below, the EAM does not comprise a self-immolative moiety, in the case where the peroxide-sensitive moiety is attached directly to the EAM and provides a change in $E^0$ when the peroxide-sensitive moiety is exposed to peroxide. As shown below, one embodiment allows the peroxide-sensitive moiety to be attached directly to the EAM (in this case, a ferrocene), such that the ferrocene has a first $E^0$ when the pinacol boronate ester moiety is attached, and a second $E^0$ when removed, e.g. in the presence of the peroxide.

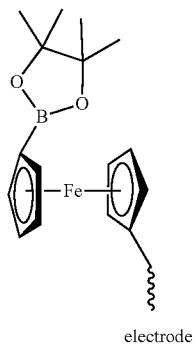

electrode

Self-immolative Moieties

The EAMs of the invention include at least one self-immolative moiety that is covalently attached to the EAM such that the EAM has a first $E^0$ when it is present and a second $E^0$ when it has been removed as described below.

The term "self-immolative spacer" refers to a bifunctional chemical moiety that is capable of covalently linking two chemical moieties into a normally stable tripartate molecule. The self-immolative spacer is capable of spontaneously separating from the second moiety if the bond to the first moiety is cleaved. In the present invention, the self-immolative spacer links a peroxide sensitive moiety, e.g. a boron moiety, to the EAM. Upon exposure to peroxide, the boron moiety is removed and the spacer falls apart, as generally depicted in FIG. 1. Generally speaking, any spacer where irreversible repetitive bond rearrangement reactions are initiated by an electron-donating alcohol functional group (i.e. quinone methide motifs) can be designed with boron groups serving as triggering moieties that generate alcohols under oxidative conditions. Alternatively, the boron moiety can mask a latent phenolic oxygen in a ligand that is a pro-chelator for a transition metal. Upon oxidation, the ligand is transformed and initiates EAM formation in the SAM. For example, a sample chelating ligand is salicaldehyde isonicotinoyl hydrazone that binds iron.

As will be appreciated by those in the art, a wide variety of self-immolative moieties may be used with a wide variety of EAMs and peroxide sensitive moieties. Self-immolative linkers have been described in a number of references, including US Publication Nos. 20090041791; 20100145036 and U.S. Pat. Nos. 7,705,045 and 7,223,837, all of which are expressly incorporated by reference in their entirety, particularly for the disclosure of self-immolative spacers.

Figure 6:
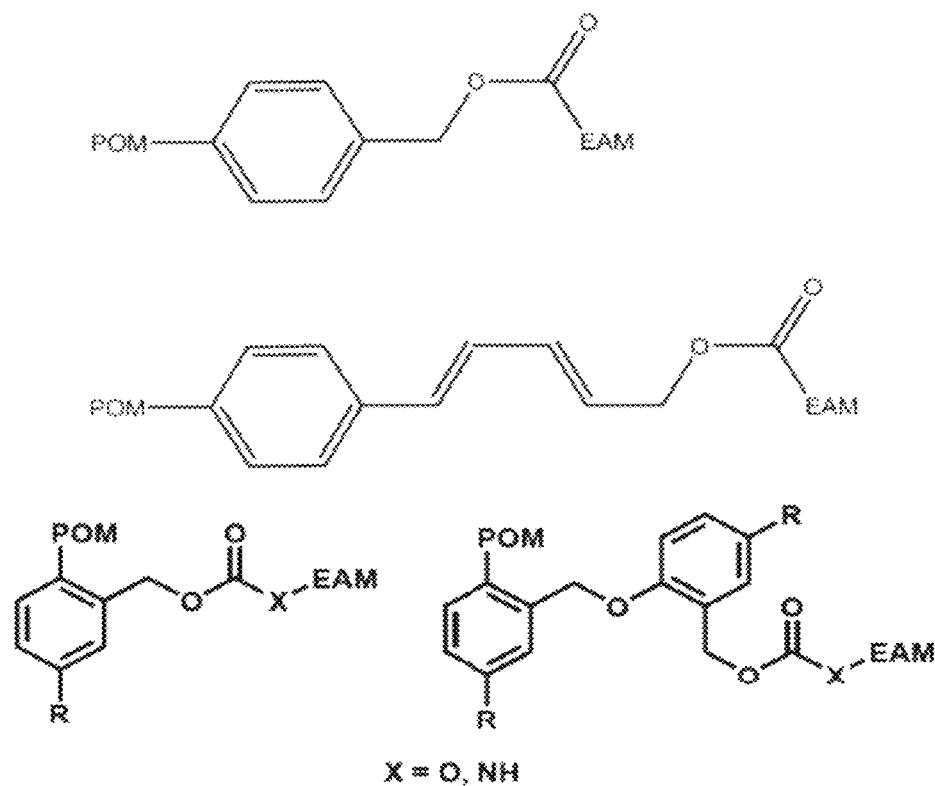
FIG. 6. Sample self-immolative spacer groups based on substituted quinone methides.
Figure 7:
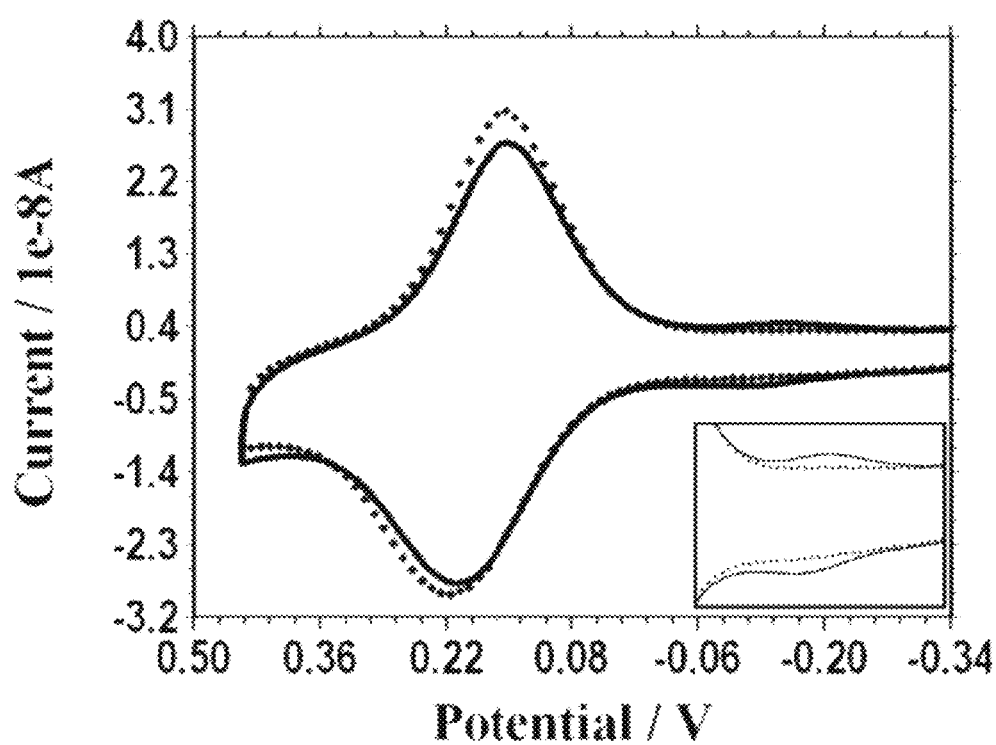
FIG. 7. Cyclic voltamogram for SAM of EAM 1 following antibody sandwich formation with human cardiac troponin I (10 ng/mL) before (dotted) and after (solid) incubation with glucose for 10 min. Inset shows the peak at −0.10V magnified.
Figure 8:
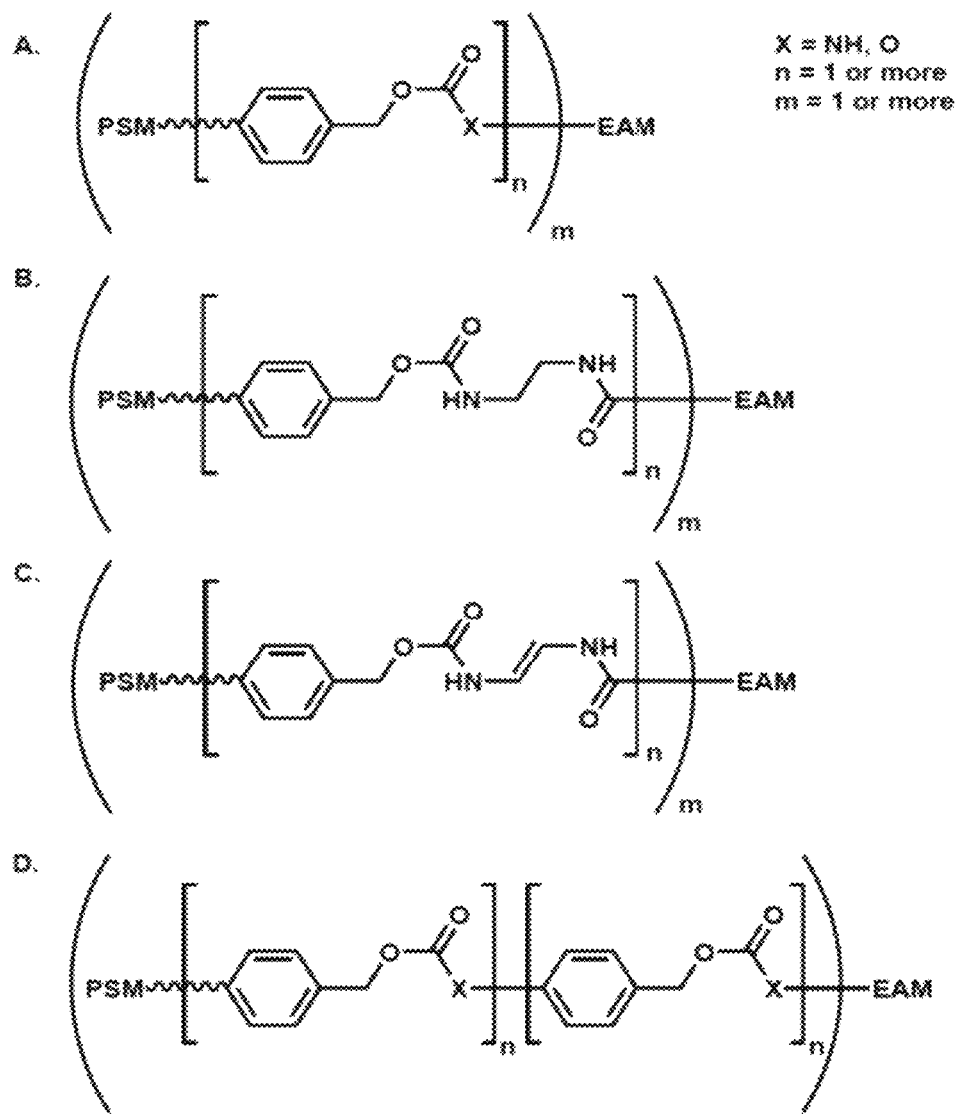
FIG. 8. Depicts a variety of self-immolative moieties which find use in the present invention. "PSM" stands for "peroxide sensitive moiety" and "EAM" stands for "electroactive moiety". As is shown in the figures, a variety of monomeric self-immolative moieties (sometimes referred to herein as "SIM") can be used.
Figure 9:
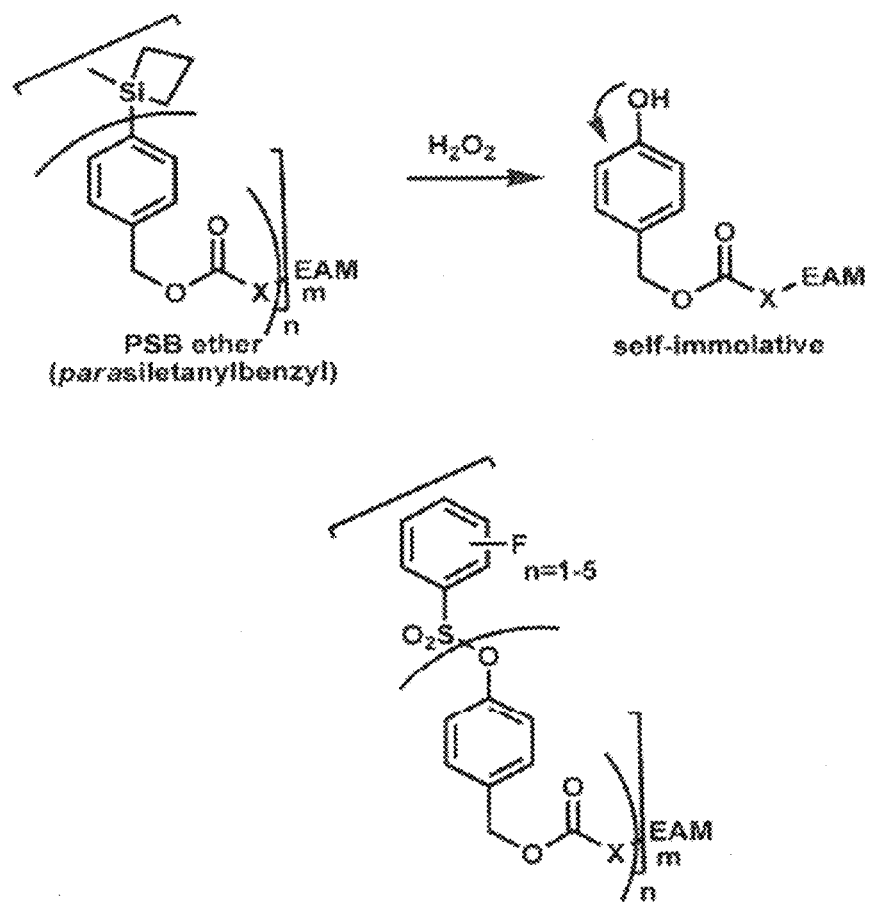
FIG. 9. Depicts additional peroxide sensitive moieties. Figure A depicts the PSB ether (parasiletanylbenzyl) moiety and Figure B depicts the pentafluorophenylsulfonate (PFPS) moiety. As shown in Figure (next), there can be more than one self-immolative moiety per EAM and/or more than one PSM-SIM per EAM. As for the boron containing PSMs, there can be multiple PSB ethers or PFPS moieties per EAM as well.

A few self-immolative linkers of particular use in the present invention are shown in FIG. 6. The self-immolative spacer can comprise a single monomeric unit or polymers, either of the same monomers (homopolymers) or of different monomers (heteropolymers). Alternatively, the self-immolative spacer can be a neighboring group to an EAM in a SAM that changes the environment of the EAM following cleavage analogous to the chemistry as recited in previous application "Electrochemical Assay for the Detection of Enzymes", U.S. Ser. No. 12/253,828, PCT/US2008/080363, hereby incorporated by reference.

Peroxide Sensitive Moieties

The self-immolative spacers join the peroxide sensitive moieties (PSMs, sometimes referred to herein as POMs) and the EAMs of the invention. In general, a peroxide sensitive moiety is a moiety containing boron as depicted in FIG. 1.

For example, the figures herein depict the use of ferrocene derivatives, where the peroxide triggers a change from a benzyl carbamate with a p-substituted pinacol borate ester to an amine. This self-eliminating group has been described previously for generating amine-functionalized florophores in the presence of hydrogen peroxide (Sella, E.; Shabat, D. Self-immolative dendritic probe for the direct detection of triacetone triperoxide. Chem. Commun. 2008, 5701-5703; and Lo, L.-Cl; Chu, C.-Y. Development of highly selective and sensitive probes for hydrogen peroxide. Chem. Commun. 2003, 2728-2729 both of which are incorporated by reference. Other such groups (aryl borate esters and arylboronic acids) are also described in Sella and Lo. In addition, ferrocenylamines are known to exhibit redox behavior at lower potentials (~150 mV) as compared to their corresponding carbamate derviatives (see Sagi et al., Amperometric Assay for Aldolase Activity; Antibody-Catalyzed Ferrocenylamine Formation. Anal. Chem. 2006, 78, 1459-1461, incorporated by reference herein).

Capture and Soluble Binding Ligands

In addition to SAMs and EAMs, in some embodiments, the electrodes comprise capture binding ligands. By "binding ligand" or "binding species" herein is meant a compound that is used to probe for the presence of the target analyte and that will bind to the target analyte. In general, for most of the embodiments described herein, there are at least two binding ligands used per target analyte molecule; a "capture" or "anchor" binding ligand that is attached to the detection surface, and a soluble binding ligand, that binds independently to the target analyte, and either directly or indirectly comprises at least one label such as a SOX. By "capture binding ligand" herein is meant a binding ligand that binds the target analyte that is attached to the electrode surface that binds the target analyte. By "soluble binding ligand" herein is meant a binding ligand that is in solution that binds the target analyte at a different site than the capture binding ligand.

As will be appreciated by those in the art, the composition of the binding ligand will depend on the composition of the target analyte. Binding ligands for a wide variety of analytes are known or can be readily found using known techniques. For example, when the analyte is a protein, the binding ligands include proteins (particularly including antibodies or fragments thereof (FAbs, etc.)) or small molecules.

In general, antibodies are useful as both capture and soluble binding ligands.

The soluble binding ligand also comprises a peroxide generating moiety such as an enzyme that generates peroxide. A wide variety of such enzymes are known, including glucose oxidase, acyl CoA oxidases, alcohol oxidases, aldehyde oxidases, etc. A wide variety of suitable oxidase enzymes are known in the art (see any glucose oxidase enzyme classified as EC 1.1.3.4, including, but not limited to, glucose oxidase, D-amino acid oxidase (DAAO) and choline oxidase). Glucose oxidase enzymes from a wide variety of organisms are well known, including bacterial, fungal and animal (including mammalian), including, but not limited to, *Aspergillus* species (e.g. *A. niger*), *Penicillum* species, *Streptomyces* species, mouse, etc.). Also of use are acyl CoA oxidases, classified as EC 1.3.3.6.

Alternatively, the soluble binding ligand may contain an enzyme, such as alkaline phosphatase (AP), that catalyzes the generation of a necessary cofactor from a phosphorylated precursor for a soluble apo-oxidase enzyme (i.e. FADP converted to FAD which binds to apo-DAAO) which in turn generates peroxide by reaction with substrate. This strategy enables cascade amplification of target binding events if the concentrations of apo-enzyme, phosphorylated cofactor, and oxidase enzyme substrate are high with respect to the surface immobilized target.

Generally, the capture binding ligand allows the attachment of a target analyte to the detection surface, for the purposes of detection. In one embodiment, the binding is specific, and the binding ligand is part of a specific binding pair.

The term "specific binding pair" as used herein refers to two compounds that specifically bind to one another in a non-covalent manner, such as but not limited to a receptor (e.g., enzyme) and a ligand; an antibody and an antigen; complementary nucleic acids; or an aptamer and its target. A "first member of a specific binding pair" can be either element of the binding pair (e.g., biotin or avoiding) and the "second member of the specific binding pair" can be the remaining element of the binding pair (e.g., where the first member of a specific binding pair is biotin, the second member of the specific binding pair can be avidin).

For example, the specific binding pair can be biotin and avidin or biotin and streptavidin, or analogs thereof (i.e. biotin or avidin/streptavidin molecules that have been modified but yet a/low for reversible binding as described herein). In another example, the specific binding pair can be an antigen and an antibody. Suitable antigens include, but are not limited to, fluorescein, biotin, digoxigenin, or dinitrophenol. In a further example, the specific binding pair can also be an aptamer and its target molecule. Aptamers can be short nucleic acid or short peptides (e.g., 6-40 kDa) which strongly bind a target molecule, typically with binding constants ($K_D$) in the micromolar to nanomolar range (i.e., <1000 μM to <1000 nM). Aptamer targets can include, but are not limited to, an organic dye (e.g., fluorescein, Cy3, Cy5), a disaccharide (e.g., cellobiose, lactose, maltose, gentiobiose), an aminoglycoside (e.g., tobramycin, lividomycin, kanamycin A, kanamycin B, neomycin B), an antibiotic (e.g, viomycin and tetracyclin), dopamine, porphyrins (e.g., hematoporphyrin), and biotin.

"Nucleic acids" may be any natural or synthetic nucleic acids, including DNA and RNA, and can be from 10 to 1,000 nucleotides in length. In certain embodiments, the nucleic acids are 10 to 100 nucleotides in length. In certain embodiments, the nucleic acids are 10 to 75 nucleotides in length; or 10 to 50 nucleotides; or 10 to 40 nucleotides in length. Shorter oligomers can be less costly but may not be robust; longer oligomers can be used for higher operating temperatures, or in harsher (e.g., pH or high salt concentration) environments.

For example, the specific binding pair can be complementary nucleic acids, such as two complementary single-stranded DNA molecules capable of forming duplex DNA, two complementary single-stranded RNA molecules capable of forming double-stranded RNA, or a single-stranded DNA molecule and a single-stranded RNA molecule capable of forming a DNA-RNA hybrid. It will be understood by one of skill in the art that the two individual nucleic acid molecules can form a binding pair complex under the appropriate hybridization or annealing conditions, and that such conditions can be optimized for the particular nucleic acid molecules at issue. It will be further understood by one of skill in the art that once formed, the duplex DNA, double-stranded RNA, or DNA-RNA hybrid can be disassociated under appropriate denaturation conditions.

By "specifically bind" herein is meant that the ligand binds the analyte, with specificity sufficient to differentiate between the analyte and other components or contaminants of the test sample. The binding should be sufficient to allow the analyte to remain bound under the conditions of the assay, including wash steps to remove non-specific binding. In some embodiments, for example in the detection of certain biomolecules, the binding constants of the analyte to the binding ligand will be at least about $10^{-4}$ to $10^{-9}$ $M^{-1}$, with at least about $10^{-5}$ to $10^{-9}$ being preferred and at least about $10^{-7}$ to $10^{-9}$ $M^{-1}$ being particularly preferred.

Binding ligands to a wide variety of analytes are known or can be readily found using known techniques. For example, when the analyte is a single-stranded nucleic acid, the binding ligand is generally a substantially complementary nucleic acid. Alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptamers" can be developed for binding to virtually any target analyte. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins (particularly including antibodies or fragments thereof (FAbs, etc.)), small molecules, or aptamers, described above. Preferred binding ligand proteins include antibodies and peptides. As will be appreciated by those in the art, any two molecules that will associate, preferably specifically, may be used, either as the analyte or the binding ligand. Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. These may be wild-type or derivative sequences.

The capture binding ligands (e.g. a capture antibody) can be covalently coupled to the electrode (usually through an attachment linker) or bound tightly but not covalently; for example, using biotin/streptavidin reactions (e.g. biotin on the surface of the SAM, streptavin-conjugated capture ligand such as an antibody, or vice versa), bound via a nucleic acid reaction (for example, the capture ligand can have a nucleic acid ("Watson") and the surface can have a complementary nucleic acid ("Crick"), bound using protein G binding to the Fc fragment of the antibody, etc.

It should also be noted that the invention described herein can also be used as a sensor for the illicit explosive triacetone triperoxide (TATP).

Anchor Groups

The present invention provides compounds including the EAM (optionally attached to the electrode surface with a conductive oligomer), the SAM, and the capture binding ligands on the electrode surface. Generally, in some embodiments, these moieties are attached to the electrode using anchor group. By "anchor" or "anchor group" herein is meant a chemical group that attaches the compounds of the invention to an electrode.

As will be appreciated by those in the art, the composition of the anchor group will vary depending on the composition of the surface to which it is attached. In the case of gold electrodes, both pyridinyl anchor groups and thiol based anchor groups find particular use.

The covalent attachment of the conductive oligomer may be accomplished in a variety of ways, depending on the electrode and the conductive oligomer used. Generally, some type of linker is used, as depicted below as "A" in Structure 1, where X is the conductive oligomer, and the hatched surface is the electrode:

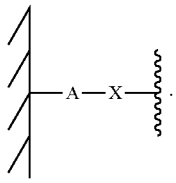

Structure 1

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977); both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties.

In some embodiments, the electrode is a carbon electrode, i.e. a glassy carbon electrode, and attachment is via a nitrogen of an amine group. A representative structure is depicted in Structure 15 of US Patent Application Publication No. 20080248592, hereby incorporated by reference in its entirety but particularly for Structures as described therein and the description of different anchor groups and the accompanying text. Again, additional atoms may be present, i.e. linkers and/or terminal groups.

In Structure 16 of US Patent Application Publication No. 20080248592, hereby incorporated by reference as above, the oxygen atom is from the oxide of the metal oxide electrode. The Si atom may also contain other atoms, i.e. be a silicon moiety containing substitution groups. Other attachments for SAMs to other electrodes are known in the art; see for example Napier et al., Langmuir, 1997, for attachment to indium tin oxide electrodes, and also the chemisorption of phosphates to an indium tin oxide electrode (talk by H. Holden Thorpe, CHI conference, May 4-5, 1998).

In one preferred embodiment, indium-tin-oxide (ITO) is used as the electrode, and the anchor groups are phosphonate-containing species.

1). Sulfur Anchor Groups

Although depicted in Structure 1 as a single moiety, the conductive oligomer may be attached to the electrode with more than one "A" moiety; the "A" moieties may be the same or different. Thus, for example, when the electrode is a gold electrode, and "A" is a sulfur atom or moiety, multiple sulfur atoms may be used to attach the conductive oligomer to the electrode, such as is generally depicted below in Structures 2, 3 and 4. As will be appreciated by those in the art, other such structures can be made. In Structures 2, 3 and 4 the A moiety is just a sulfur atom, but substituted sulfur moieties may also be used.

Thus, for example, when the electrode is a gold electrode, and "A" is a sulfur atom or moiety, such as generally depicted below in Structure 6, multiple sulfur atoms may be used to attach the conductive oligomer to the electrode, such as is generally depicted below in Structures 2, 3 and 4. As will be appreciated by those in the art, other such structures can be made. In Structures 2, 3 and 4, the A moiety is just a sulfur atom, but substituted sulfur moieties may also be used.

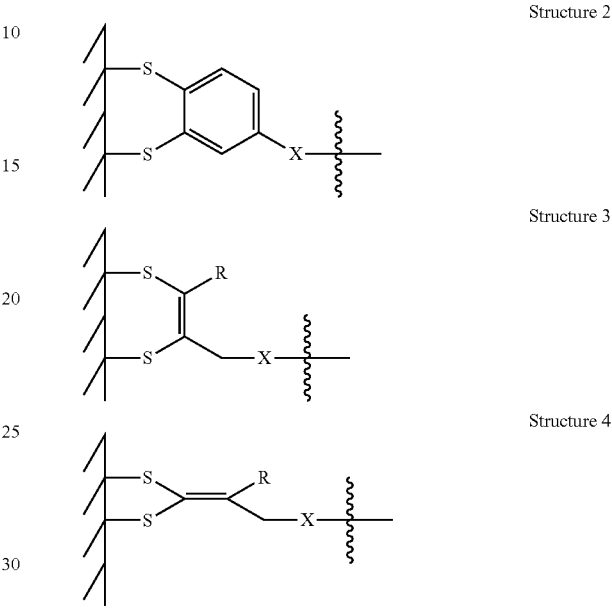

Structure 2

Structure 3

Structure 4

It should also be noted that similar to Structure 4, it may be possible to have a conductive oligomer terminating in a single carbon atom with three sulfur moieties attached to the electrode.

Figure 4:
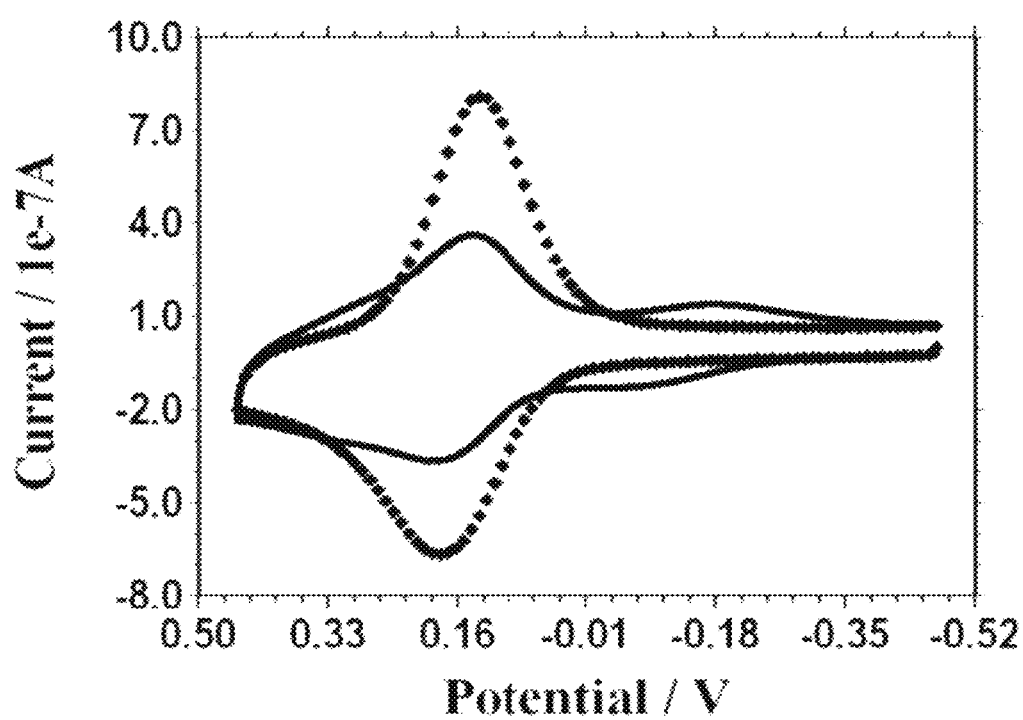
FIG. 4. Overlaid cyclic voltammograms from a SAM of EAM 1 before (dotted) and after solid incubation with 1 mM hydrogen peroxide in NaHCO$_3$ buffer (pH 8.5) for 10 min, followed by a 5-min wash in Na$_2$CO$_3$ buffer (pH 10.1; lower peaks). Supporting electrolyte was 1M LiClO$_4$, silver quasi reference electrode, platinum wire counter electrode. Scan rate was 10000 mV/s.
Figure 5:
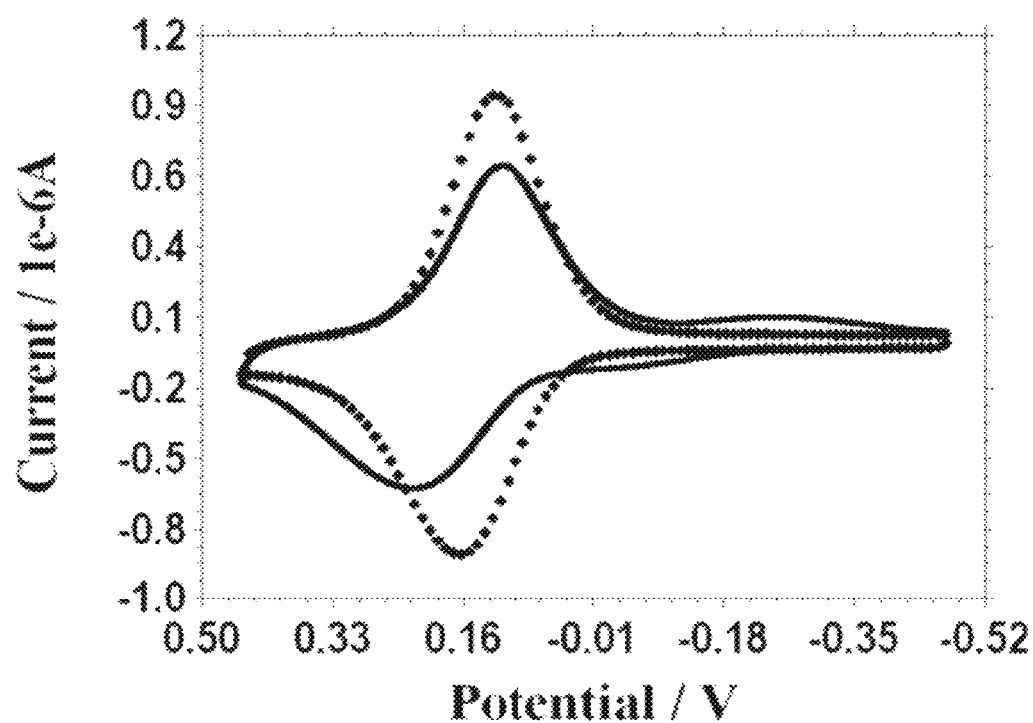
FIG. 5. Overlaid cyclic voltammograms from a SAM of EAM 1 before (dotted) and after (solid) incubation with 1 mM glucose and 100 uM glucose oxidase in NaHCO$_3$ buffer (pH 8.5) for 10 min, followed by a 5 min wash in Na$_2$CO$_3$ buffer (pH 10.1). Supporting electrolyte was 1M LiClO$_4$, silver quasi reference electrode, platinum wire counter electrode. Scan rate was 10000 mV/s.
Figure 10:
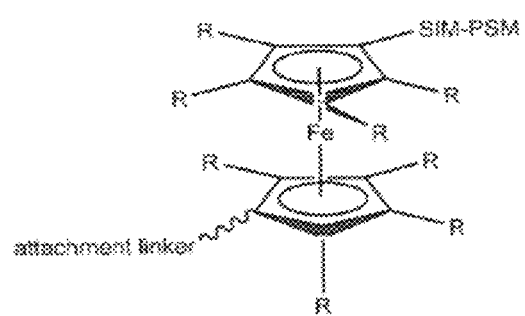
FIG. 10. Depicts a ferrocene that has R groups. The moiety shown has the attachment linker and the self-immolative moiety and the peroxide sensitive moiety on different rings, although as described herein, they can be on the same ring. In addition, any or all of the R groups can be an additional -SIM-PSM substituent, as well as traditional substituents (alkyl (including substituted alkyl, heteroalkyl, cyclic alkyl, etc.), aryl (including substituted aryl and heteroaryl), etc.).

In another aspect, the present invention provide anchor comprise conjugated thiols. Some exemplary complexes with conjugated thiol anchors are shown in FIG. 10. In some embodiments, the anchor comprises an alkylthiol group. Some of the examples are shown in FIGS. 10A and 4B. The two compounds depicts in FIG. 10B are based on carbene and 4-pyridylalanine, respectively.

In another aspect, the present invention provides conjugated multipodal thio-containing compounds that serve as anchoring groups in the construction of electroactive moieties for analyte detection on electrodes, such as gold electrodes. That is, spacer groups (which can be attached to EAMs, ReAMCs, or an "empty" monolayer forming species) are attached using two or more sulfur atoms. These mulitpodal anchor groups can be linear or cyclic, as described herein.

In some embodiments, the anchor groups are "bipodal", containing two sulfur atoms that will attach to the gold surface, and linear, although in some cases it can be possible to include systems with other multipodalities (e.g. "tripodal"). Such a multipodal anchoring group display increased stability and/or allow a greater footprint for preparing SAMs from thiol-containing anchors with sterically demanding headgroups.

In some embodiments, the anchor comprises cyclic disulfides ("bipod"). Although in some cases it can be possible to include ring system anchor groups with other multipodalities (e.g. "tripodal"). The number of the atoms of the ring can vary, for example from 5 to 10, and also includes multicyclic anchor groups, as discussed below In some embodiments, the anchor groups comprise a [1,2,5]-dithiazepane unit which is seven-membered ring with an apex nitrogen atom and a intramolecular disulfide bond as shown below:

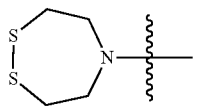
(IIIa)

In Structure (IIIa), it should also be noted that the carbon atoms of the ring can additionally be substituted. As will be appreciated by those in the art, other membered rings are also included. In addition, multicyclic ring structures can be used, which can include cyclic heteroalkanes such as the [1,2,5]-dithiazepane shown above substituted with other cyclic alkanes (including cyclic heteroalkanes) or aromatic ring structures.

In some embodiments, the anchor group and part of the spacer has the structure shown below

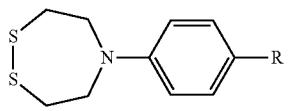
(IIIb)

The "R" group herein can be any substitution group, including a conjugated oligophenylethynylene unit with terminal coordinating ligand for the transition metal component of the EAM.

The anchors are synthesized from a bipodal intermediate (I) (the compound as formula III where R=I), which is described in Li et al., Org. Lett. 4:3631-3634 (2002), herein incorporated by reference. See also Wei et al, J. Org, Chem. 69:1461-1469 (2004), herein incorporated by reference.

The number of sulfur atoms can vary as outlined herein, with particular embodiments utilizing one, two, and three per spacer.

As will be appreciated by those in the art, the compositions of the invention can be made in a variety of ways, including those outlined below and in U.S. patent application Ser. No. 12/253,828, filed Oct. 17, 2008; U.S. patent application Ser. No. 12/253,875, filed Oct. 17, 2008; U.S. Provisional Patent Application No. 61/332,565, filed May 7, 2010; U.S. Provisional Patent Application No. 61/347,121, filed May 21, 2010; U.S. Provisional Patent Application No. 61/366,013, filed Jul. 20, 2010. In some embodiments, the composition are made according to methods disclosed in of U.S. Pat. Nos. 6,013,459, 6,248,229, 7,018,523, 7,267,939, U.S. patent application Ser. Nos. 09/096,593 and 60/980,733, and U.S. Provisional Application No. 61/087,102, filed on Aug. 7, 2008, all are herein incorporated in their entireties for all purposes.

Applications

Figure 11:
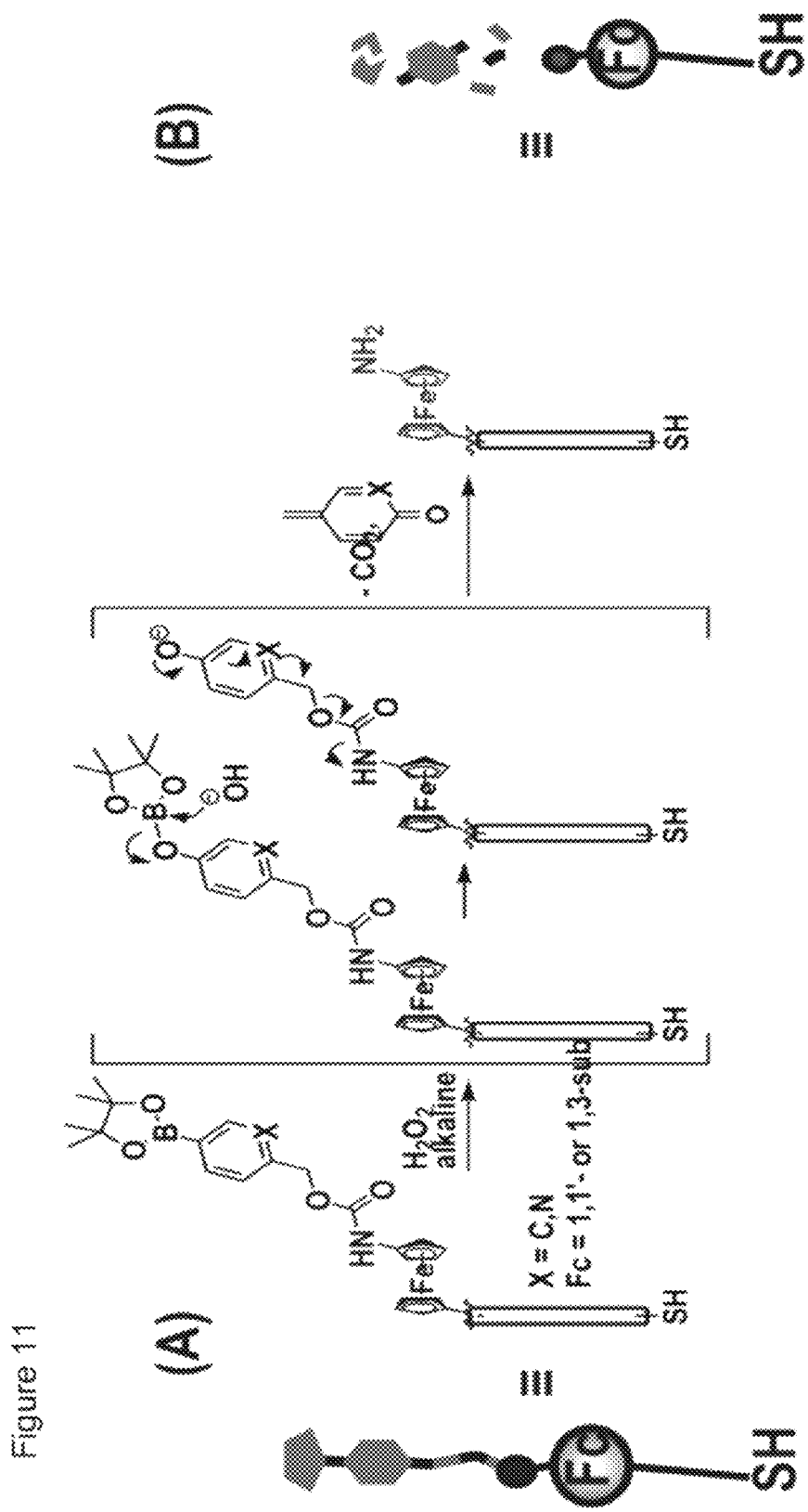
FIG. 11 is similar to FIG. 1 in showing the reaction mechanism for a representative ferrocene based EAM that undergoes a peroxide-triggered change in the apparent formal potential. (A) is the starting ferrocenyl EAM that contains an electron-withdrawing carbamate-linked boronate ester-substituted ligand. (B) Shows that the reaction with peroxide leads to an electron-donating amino ligand on the ferrocene which changes the redox potential ($E^0$).
Figure 12:
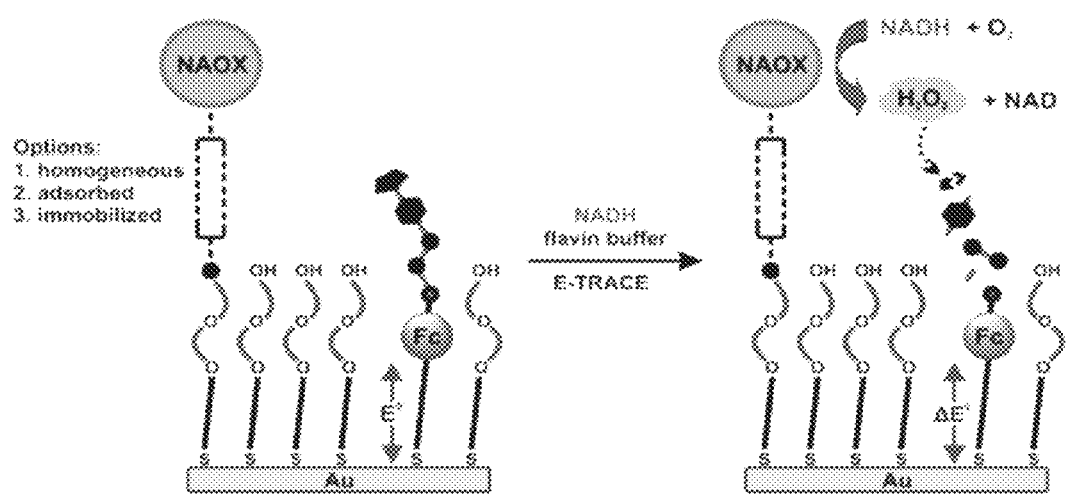
FIG. 12 depicts a representative metabolite assay for the detection of NADH in a sample. In this particular embodiment, the NADH oxidase (nicotinamide adenine dinucleotide phosphate-oxidase) is attached to the electrode using a biotin-streptavidin system, although as will be appreciated by those in the art, any number of additional methods can be used, including the use of the NHS or maleimide system outlined in PCT/US2008/080379, hereby incorporated by reference in its entirety. In this embodiment, the NADH oxidase is attached via an amine or other functional group, such as the N-terminus, using activation chemistry.
Figure 13:
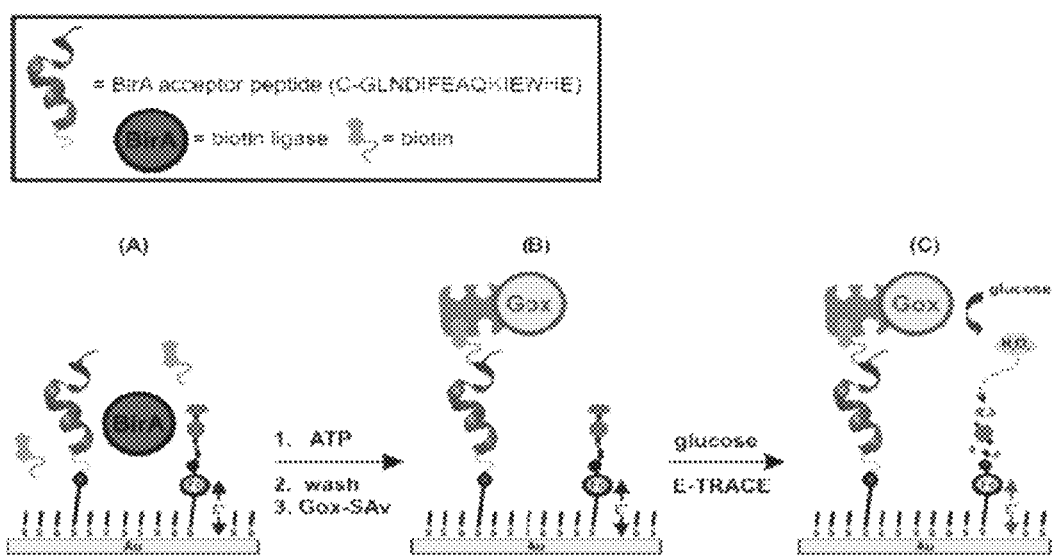
FIG. 13 depicts one embodiment of the electrochemical detection of ATP as a metabolite in a sample. In this embodiment, the sensor is based on a SAM-modified gold electrode that contains peroxide-triggered electroactive molecules (EAMs, sometimes alternatively referred to herein as "redox active moieties" (RAMs)) and acceptor peptide (AP) substrates for BirA (biotin ligase, in this case from *E. coli*) with physisorbed biotin and BirA (FIG. 13A).

The systems of the invention find use in the detection of a variety of target analytes, as outlined herein. In some embodiments, "sandwich" type assays are used, as are generally depicted in FIGS. 11-13. In other embodiments, for example for the detection of particular metabolites such as ATP and NADH, other formats are used.

In some embodiments, for example in "sandwich" type formats, the target analyte, contained within a test sample, is added to the electrode with the PSM-SIM-EAM mixture, a capture binding ligand, and optionally a SAM. This addition is followed by an optional washing step and the addition of the soluble binding ligand, although as will be appreciated by those in the art, these additions can be done simultaneously or the solution binding ligand can be added to the sample containing the target analyte prior to addition to the chip. The surface is again optionally washed, and the substrate for the peroxide sensitive moiety, e.g. glucose, is added under conditions that if present, peroxide is generated and the SIM is cleaved.

In some embodiments, for example when there is a specific peroxidase-generating enzyme that uses a metabolite of interest (e.g. a target analyte or target metabolite), as depicted in FIGS. 12 and 13, the system takes on different configurations. For example, in FIG. 12, the electrode, generally with a SAM, contains at least two species: (1) an EAM with a self-immolative moiety, depicted in FIG. 12 as a ferrocene-based derivative (although as described herein and as will be appreciated by those in the art, other EAMs can be used); and (2) an attached peroxidase-generating enzyme, in this case, as depicted, NADH oxidase. As outlined herein, the peroxidase-generating enzyme can be attached to the electrode surface in a number of different ways. The attachment can be "direct" when the enzyme is attached to the terminus of a monolayer forming species, as is generally outlined in PCT/US2008/080379, using a coupling chemistry. Alternatively, and as depicted in FIG. 12, the enzyme can be attached using a number of "sandwich" type attachments, for example using a monolayer species with a biotin attached, a streptavidin and a biotin-labeled enzyme.

In some embodiments, these two species can be attached as a single moiety to the electrode surface, for example as generally depicted in Structure 7 of U.S. Pat. No. 7,595,153, hereby incorporated by reference in its entirety and specifically for the schematics of attachment configurations.

The ATP sensor can be based on a SAM-modified gold electrode that contains peroxide-reactive electroactive molecules (EAMs). The initial apparent formal potential of EAMs in the monolayer characterizes the sensor "off" state. Upon exposure to an ATP-containing sample matrix, hydrogen peroxide production triggers an irreversible elimination reaction in the immobilized EAMs resulting in a signal "on" change in apparent formal potential of ferrocene groups that is detected electrochemically. This enzyme-triggered redox altering chemical elimination (E-TRACE) reaction for a representative class of ferrocene EAMs is shown in FIG. 11. (see e.g. U.S. patent application Ser. No. 12/853,204). In some embodiments, metabolites or other target analytes of interest can be detected on the basis of an event, such as an enzymatic event, occurring as the result of the presence of the metabolite or target analyte. For example, ATP can be detected in several ways. In one embodiment, an enzymatic event that relies on the presence of ATP results in some sort of "switch" that then allows detection.

ATP is a multifunctional nucleotide that serves as the energy source for many biological processes in living organisms. Thus, strategies for the detection of ATP have been a central focus for researchers in the fields of clinical diagnostics, microbiology, environmental analyses, and food quality control. To date, numerous ATP sensors have emerged based on colorometric, fluorometric, or electrochemical detection methods. In particular, sensors that employ ATP-dependent enzymatic reactions (i.e those catalyzed by firefly luciferase, (Kadidate et al., Anal. Chem. 2006 78:337-342 and DNA ligase, Wang et al., Biosens. Bioelectron. 2010 25:2101-2106, both of which are expressly incorporated by reference in their entirety) to generate an output signal are attractive due to their inherent sensitivity and specificity. In one embodiment, ATP electrochemically is detected by exploiting the ATP-dependent biotinylation reaction catalyzed by *E. Coli* biotin ligase (BirA) at a SAM-modified gold electrode. In another embodiment, ATP is electrochemically detected by exploiting ATP-dependent enzymatic reactions with a SAM-modified gold electrode.

Among the class of enzymes that catalyze the post-translational modification of proteins with biotin, BirA has been shown to site-specifically biotinylate lysine in the 15-amino acid acceptor peptide (AP) sequence (GLNDIFEAQKIE-WHE) with kinetics similar to those of the natural protein substrate (see Beckett et al, Protein Sci. 1999 8:921-929, expressly incorporated herein in its entirety). This enzymatic biotinylation reaction proceeds via two steps:

1.) biotin+ATP→biotinyl-5'-AMP+PPi
2.) biotinyl-5'-AMP+AP→biotin-AP+AMP

First, BirA catalyzes the formation of biotinyl-5'-AMP from biotin and ATP. Subsequently, the target lysine residue on the docked peptide/protein substrate is biotinylated through nucleophilic attack on this activated biotin intermediate (Cronan Cell 1989 58:427-429, expressly incorporated herein by reference in its entirety). For example, as depicted in FIG. 12, the electrode is formed with an attached acceptor peptide (AP) that serves as the substrate for the biotin ligase enzyme, as well as an EAM with a self-immolative moiety. A sample containing ATP is added to the electrode in the presence of the biotinylating enzyme and biotin, such that in the presence of ATP, biotin is added to the surface. A streptavidin-oxidase enzyme conjugate is then added, after optionally washing away the non-bound substrates, and then glucose is added, such that the peroxide generating enzyme results in the destruction of the self-immolative linker and a change in the redox potential ($E^0$) of the ferrocene moiety.

Figure 14:
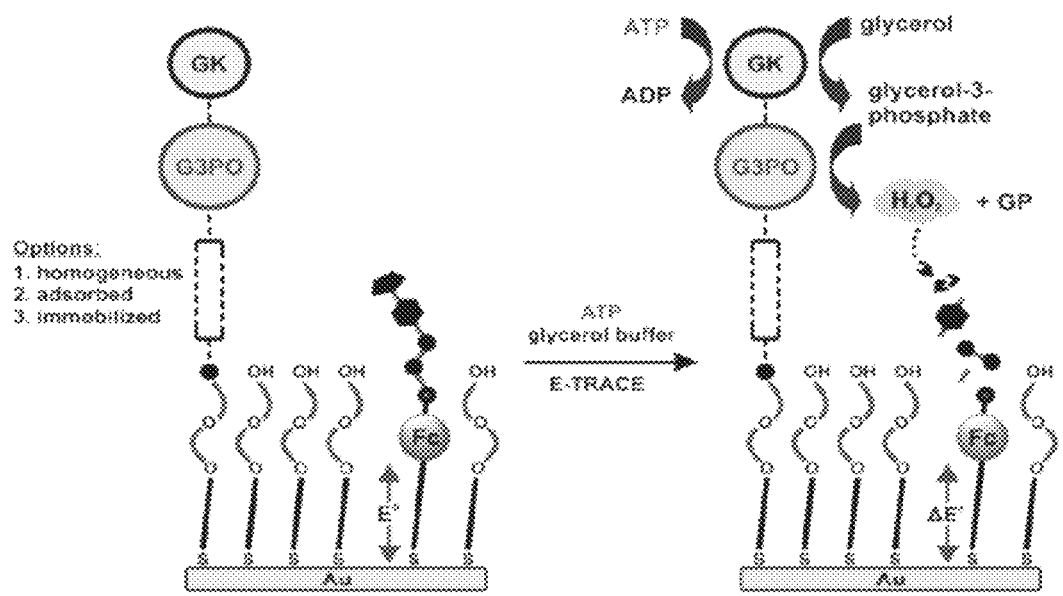
FIG. 14. Schematic representation of an electrochemical ATP assay. G3PO may be in solution or immobilized at the SAM interface via biotin-streptavidin binding or by adsorption to the SAM interface.
Figure 15:
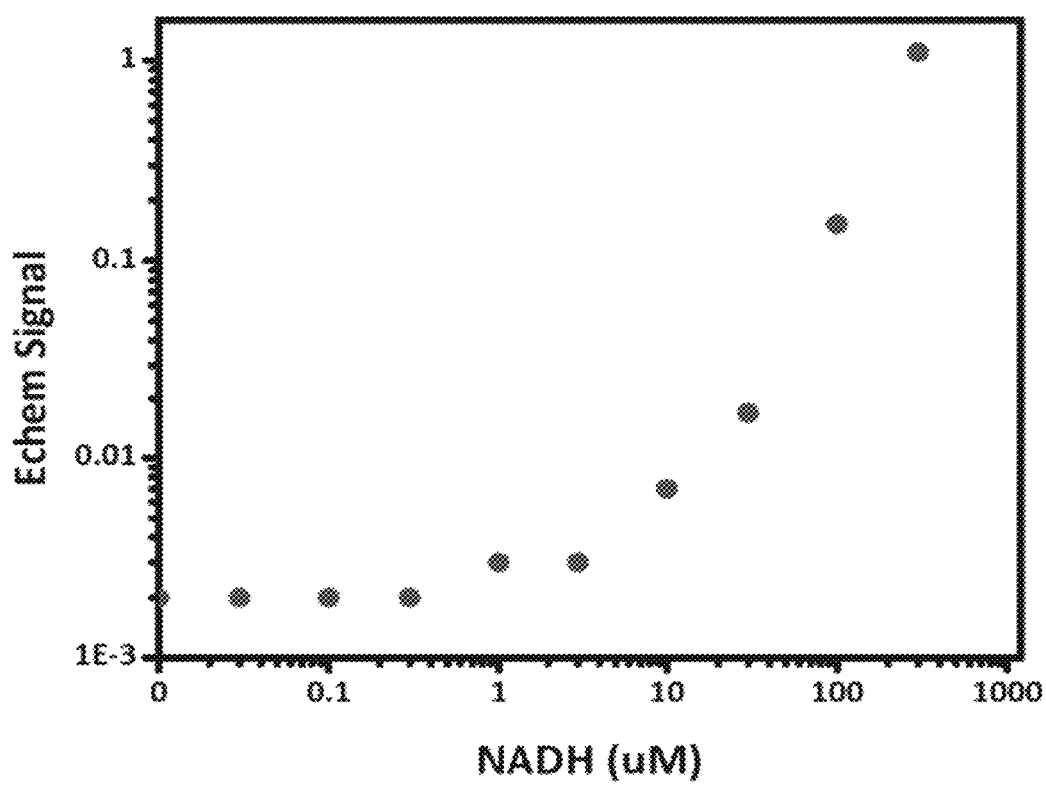
FIG. 15. Electrochemical data for NADH detection as described in Example 4.

In another embodiment, ATP is electrochemically exploited. In some embodiments, ATP can be electrochemically detected by exploiting the ATP-dependent enzymatic reactions with a SAM-modified gold electrode by using the activities of glycerol kinase (GK) and glycerol-3-phosphate oxidase (G3PO) if the co-substrate glycerol is present in the reaction mixture (see Murphy, L. J. et al. *Anal. Chem.* 1994, 66, 4345-4353; and Llaudet, E. et al., *Anal. Chem.* 2005, 77, 3267-3273). The enzymatic steps proceed as follows:

1.) glycerol+ATP+GK→glycerol-3-phosphate+ADP
2.) glycerol-3-phosphate+G3PO+$O_2$→glycerone phosphate+$H_2O_2$ GK can catalyze the formation of glycerol-3-phosphate from glycerol and ATP. Subsequently, G3PO oxidizes glycerol-3-phosphate to yield glycerone phosphate and hydrogen peroxide. Thus, the amount of peroxide produced is directly linked to the amount of ATP in the sample if glycerol is in excess. An approach toward the electrochemical detection of peroxide produced from this enzymatic reaction sequence is shown in FIG. 14.

Therein, each of the enzymes, such as G3PO and GK may be immobilized to a surface by chemical bonding (optionally via a linking group described herein), may be physiochemically adsorbed with to a surface (e.g., via hydrophoblic interactions), or may be a homogeneous part of the solution in contact with the electrode. The surface to which the enzymes are immobilized or adsorbed may be a surface of the electrode, or a surface of any enclosing body (e.g., a reaction cell) which contains the electrode and is in fluidly connected to the electrode via the solution that in contact with the electrode.

In certain embodiments, each of the enzymes are immobilized to the electrode surface. In certain other embodiments, an oxidase is immobilized to the substrate surface and any other enzyme may be immobilized or adsorbed to the surface of the electrode, or a homogeneous part of the solution in contact with the electrode.

These conditions are generally physiological conditions. Generally a plurality of assay mixtures is run in parallel with different concentrations to obtain a differential response to the various concentrations. Typically, one of these concentrations serves as a negative control, i.e., at zero concentration or below the level of detection. In addition, any variety of other reagents may be included in the screening assay. These include reagents like salts, neutral proteins, e.g. albumin, detergents, etc which may be used to facilitate optimal binding and/or reduce non-specific or background interactions. Also reagents that otherwise improve the efficiency of the assay, such as protease inhibitors, nuclease inhibitors, antimicrobial agents, etc., may be used. The mixture of components may be added in any order that provides for the requisite binding.

The generation of peroxidase results in the loss of the PGM-SIM component of the complex, resulting in a change in the $E^0$ of the EAM. In some embodiments, the $E^0$ of the EAM changes by at about 20 mV, 30 mV, 40 mV, 50 mV, 75 mV, 80 mV, 90 mV to 100 mV, some embodiments resulting in changes of 200, 300 or 500 mV being achieved. In some embodiments, the change in the $E^0$ of the EAM is a decrease. In some embodiments, the change in the $E^0$ of the EAM is an increase.

The determination of solvent reorganization energy will be done as is appreciated by those in the art. Briefly, as outlined in Marcus theory, the electron transfer rates (kET) are determined at a number of different driving forces (or free energy, $\Delta G^\circ$); the point at which the rate equals the free energy is the $\lambda$. This may be treated in most cases as the equivalent of the solvent reorganization energy; see Gray et al. Ann. Rev. Biochem. 65:537 (1996), hereby incorporated by reference.

The solvent inhibited redox active molecule, indicating the presence of a target analyte, is detected by initiating electron transfer and detecting a signal characteristic of electron transfer between the solvent inhibited redox active molecule and the electrode.

Electron transfer is generally initiated electronically, with voltage being preferred. A potential is applied to a sample containing modified nucleic acid probes. Precise control and variations in the applied potential can be via a potentiostat and either a three electrode system (one reference, one sample and one counter electrode) or a two electrode system (one sample and one counter electrode). This allows matching of applied potential to peak electron transfer potential of the system which depends in part on the choice of redox active molecules and in part on the conductive oligomer used.

Preferably, initiation and detection is chosen to maximize the relative difference between the solvent reorganization energies of the solvent accessible and solvent inhibited redox active molecules.

Detection

Electron transfer between the redox active molecule and the electrode can be detected in a variety of ways, with electronic detection, including, but not limited to, amperommetry, voltammetry, capacitance and impedance being preferred. These methods include time or frequency dependent methods based on AC or DC currents, pulsed methods, lock in techniques, and filtering (high pass, low pass, band pass). In some embodiments, all that is required is electron transfer detection; in others, the rate of electron transfer may be determined.

In some embodiments, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry, and photoelectrochemistry.

In certain embodiments, amperommetry is used for electronic detection. The electrical current at the electrode can be determined in the presence of and the absence of a target analyte, intermediary enzyme, co-factor, oxidase (e.g., peroxide generating enzyme), or other enzyme substrate, to determine the presence and/or concentration of a target analyte. In each measurement, the current can be measured at the same or different electrical potentials. For example, the electrical current can be measured at a first $E^0$ and at a second $E^0$ after addition of a target analyte, intermediary enzyme, co-factor, oxidase (e.g., peroxide generating enzyme), or other enzyme substrate.

In some embodiments, monitoring electron transfer is via amperometric detection. This method of detection involves applying a potential (as compared to a separate reference electrode) between the electrode containing the compositions of the invention and an auxiliary (counter) electrode in the test sample. Electron transfer of differing efficiencies is induced in samples in the presence or absence of target analyte.

The device for measuring electron transfer amperometrically involves sensitive current detection and includes a means of controlling the voltage potential, usually a potentiostat. This voltage is optimized with reference to the potential of the redox active molecule.

In some embodiments, alternative electron detection modes are utilized. For example, potentiometric (or voltammetric) measurements involve non faradaic (no net current flow) processes and are utilized traditionally in pH and other ion detectors. Similar sensors are used to monitor electron transfer between the redox active molecules and the electrode. In addition, other properties of insulators (such as resistance) and of conductors (such as conductivity, impedance and capicitance) could be used to monitor electron transfer between the redox active molecules and the electrode. Finally, any system that generates a current (such as electron transfer) also generates a small magnetic field, which may be monitored in some embodiments.

In some embodiments, the system may be calibrated to determine the amount of solvent accessible redox active molecules on an electrode by running the system in organic solvent prior to the addition of target. This is quite significant to serve as an internal control of the sensor or system. This allows a preliminary measurement, prior to the addition of target, on the same molecules that will be used for detection, rather than rely on a similar but different control system. Thus, the actual molecules that will be used for the detection can be quantified prior to any experiment. Running the system in the absence of water, i.e. in organic solvent such as acetonitrile, will exclude the water and substantially negate any solvent reorganization effects. This will allow a quantification of the actual number of molecules that are on the surface of the electrode. The sample can then be added, an output signal determined, and the ratio of bound/unbound molecules determined. This is a significant advantage over prior methods.

It should be understood that one benefit of the fast rates of electron transfer observed in the compositions of the invention is that time resolution can greatly enhance the signal to noise results of monitors based on electronic current. The fast rates of electron transfer of the present invention result both in high signals and stereotyped delays between electron transfer initiation and completion. By amplifying signals of particular delays, such as through the use of pulsed initiation of electron transfer and "lock in" amplifiers of detection, orders of magnitude improvements in signal to noise may be achieved.

In some embodiments, electron transfer is initiated and detected using direct current (DC) techniques. As noted above, the $E^0$ of the redox active molecule can shift as a result of the change in the solvent reorganization energy upon target analyte binding. Thus, measurements taken at the $E^0$ of the solvent accessible redox active molecule and at the $E^0$ of the solvent inhibited molecule will allow the detection of the analyte. As will be appreciated by those in the art, a number of suitable methods may be used to detect the electron transfer.

In some embodiments, electron transfer is initiated using alternating current (AC) methods. A first input electrical signal is applied to the system, preferably via at least the sample electrode (containing the complexes of the invention) and the counter electrode, to initiate electron transfer between the electrode and the second electron transfer moiety. Three electrode systems may also be used, with the voltage applied to the reference and working electrodes. In this embodiment, the first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 500 mV being especially preferred. The AC frequency ranges from about 0.01 Hz to about 10 MHz, with from about 1 Hz to about 1 MHz being preferred, and from about 1 Hz to about 100 kHz being especially preferred In some embodiments, the first input signal comprises a DC component and an AC component. That is, a DC offset voltage between the sample and counter electrodes is swept through the electrochemical potential of the second electron transfer moiety. The sweep is used to identify the DC voltage at which the maximum response of the system is seen. This is generally at or about the electrochemical potential of the redox active molecule. Once this voltage is determined, either a sweep or one or more uniform DC offset voltages may be used. DC offset voltages of from about 1 V to about +1.1 V are preferred, with from about 500 mV to about +800 mV being especially preferred, and from about 300 mV to about 500 mV being particularly preferred. On top of the DC offset voltage, an AC signal component of variable amplitude and frequency is applied. If the redox active molecule has a low enough solvent reorganization energy to respond to the AC perturbation, an AC current will be produced due to electron transfer between the electrode and the redox active molecule.

In some embodiments, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, as noted above, it may be possible to distinguish between solvent accessible and solvent inhibited redox active molecules on the basis of the rate of electron transfer, which in turn can be used either to distinguish the two on the basis of frequency or overpotential.

In some embodiments, measurements of the system are taken at least two separate amplitudes or overpotentials, with measurements at a plurality of amplitudes being preferred. As noted above, changes in response as a result of changes in amplitude may form the basis of identification, calibration and quantification of the system.

In some embodiments, the AC frequency is varied. At different frequencies, different molecules respond in different ways. As will be appreciated by those in the art, increasing the frequency generally increases the output current. However, when the frequency is greater than the rate at which electrons may travel between the electrode and the redox active molecules, higher frequencies result in a loss or decrease of output signal. At some point, the frequency will be greater than the rate of electron transfer through even solvent inhibited redox active molecules, and then the output signal will also drop.

In addition, the use of AC techniques allows the significant reduction of background signals at any single frequency due to entities other than the covalently attached nucleic acids, i.e. "locking out" or "filtering" unwanted signals. That is, the frequency response of a charge carrier or redox active molecule in solution will be limited by its diffusion coefficient. Accordingly, at high frequencies, a charge carrier may not diffuse rapidly enough to transfer its charge to the electrode, and/or the charge transfer kinetics may not be fast enough. This is particularly significant in embodiments that do not utilize a passivation layer monolayer or have partial or insufficient monolayers, i.e. where the solvent is accessible to the electrode. As outlined above, in DC techniques, the presence of "holes" where the electrode is accessible to the solvent can result in solvent charge carriers "short circuiting" the system. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In some embodiments, measurements of the system are taken at least two separate frequencies, with measurements at a plurality of frequencies being preferred. A plurality of frequencies includes a scan. In a preferred embodiment, the frequency response is determined at least two, preferably at least about five, and more preferably at least about ten frequencies.

Signal Processing

After transmitting the input signal to initiate electron transfer, an output signal is received or detected. The presence and magnitude of the output signal will depend on the overpotential/amplitude of the input signal; the frequency of the input AC signal; the composition of the intervening medium, i.e. the impedance, between the electron transfer moieties; the DC offset; the environment of the system; and the solvent. At a given input signal, the presence and magnitude of the output signal will depend in general on the solvent reorganization energy required to bring about a change in the oxidation state of the metal ion. Thus, upon transmitting the input signal, comprising an AC component and a DC offset, electrons are transferred between the electrode and the redox active molecule, when the solvent reorganization energy is low enough, the frequency is in range, and the amplitude is sufficient, resulting in an output signal.

In some embodiments, the output signal comprises an AC current. As outlined above, the magnitude of the output current will depend on a number of parameters. By varying these parameters, the system may be optimized in a number of ways.

In general, AC currents generated in the present invention range from about 1 femtoamp (fA) to about 1 milliamp (mA), with currents from about 50 fA to about 100 $\mu$A being preferred, and from about 1 pA to about 1 $\mu$A being especially preferred.

Apparatus

The present invention further provides apparatus for the detection of analytes using AC detection methods. The apparatus includes a test chamber which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In yet another embodiment, the first measuring electrode comprises a redox active complex, covalently attached via a spacer, and preferably via a conductive oligomer, such as are described herein. Alternatively, the first measuring electrode comprises covalently attached redox active molecules and binding ligands.

The apparatus further comprises a voltage source electrically connected to the test chamber; that is, to the measuring electrodes. Preferably, the voltage source is capable of delivering AC and DC voltages, if needed.

In an embodiment, the apparatus further comprises a processor capable of comparing the input signal and the output signal. The processor is coupled to the electrodes and configured to receive an output signal, and thus detect the presence of the target analyte.

EXAMPLES

Example 1

Preparation of Compounds 1-5 and Electrochemical Evaluation

General Methods and Materials. Unless otherwise noted, all synthetic manipulations were performed under a dry argon atmosphere using standard Schlenk techniques. For reaction media, solvents were dried over neutral alumina via the Dow-Grubbs solvent system acquired from Glass Contours (Laguna Beach, Calif.). These solvents were deoxygenated with argon prior to use. Reactions were monitored by TLC using EMD pre-coated aluminum plates (silica gel 60, $F_{254}$, EMD Chemicals, Inc., Gibbstown, N.J.). Spots were visualized by one of the following methods: iodine vapor, exposure to UV light, or staining with phosphomolybdic acid followed by heating. Flash chromatography was carried out on silica (silica gel 60 particle size: 40-63 $\mu$m; Sorbent Technologies, Atlanta, Ga.) under a positive pressure of laboratory air. $^1$H NMR and proton-decoupled $^{13}$C NMR spectra were recorded on a Bruker Avance III spectrometer (499.37 MHz for $^1$H, 125.58 MHz for $^{13}$C) and were processed with Bruker TOP-SPIN 2.1 software. High-resolution mass spectrometry (HRMS) was obtained using an Agilent 6210 time-of-flight (TOF) LC/MS instrument using electrospray ionization (ESI) or atmospheric pressure photoionization (APPI) methods.

Chloroform-d$_1$ was purchased from Cambridge Isotope Laboratories. Compound 2 and p-pinacolborate benzyl alcohol were synthesized as described previously (Bertin, P. A.; Meade, T. J. *Tetrahedron Lett.* 2009, 50, 5409-5412; Sella, E.; Shabat, D. *Chem. Commun.* 2008, 5701-5703, both of which are expressly incorporated by reference). All other reagents were purchased from commercial sources and used without further purification unless otherwise noted.

Compound 3. To a solution of compound 2 (0.500 g, 1.2 mmol) and triethylamine (0.25 mL, 1.8 mmol) in tetrahydrofuran (15 mL) was added diphenylphosphoryl azide (DPPA) (0.285 mL, 1.32 mmol). The reaction was stirred at room temperature for 1.5 hours and concentrated under reduced pressure. The crude residue was purified by column chromatography (methanol:ethyl acetate:dichloromethane 0.5:1.5:8) to yield the title compound as a red/orange solid (0.460 g, 1.04 mmol, 87%). $^1$H NMR, $^{13}$C{$^1$H} NMR, and HRMS were consistent with the title compound.

Compound 4. A solution of compound 3 (0.460 g, 1.04 mmol) in toluene (20 mL) was vigorously degassed with Ar and heated to 100° C. for 1.5 hours, p-pinacolborate benzyl alcohol (0.268 g, 1.14 mmol) and dibutyltin-dilaurate (DBTL) (0.018 mL, 0.03 mmol) were added and the reaction maintained at 100° C. for an additional 2 hours. The reaction was concentrated under reduced pressure and the crude residue purified by column chromatography (diethyl ether:ethyl acetate:dichloromethane, 1:2:2) to yield the title compound as a pale orange solid (0.480 g, 0.741 mmol, 71%). $^1$H NMR, $^{13}$C{$^1$H} NMR, and HRMS were consistent with the title compound.

Compound 5. A solution of compound 4 (0.135 g, 0.209 mmol) in dichloromethane (5 mL) was cooled in an ice bath. Trifluoroacetic acid:dichloromethane (1:1 v/v, 5 mL) was added dropwise over 5 min. After 15 min, the ice bath was removed and the reaction warmed to room temperature. After 45 min, the volatiles were removed in vacuo to yield the trifluoroacetate salt of the title compound as a brown/orange solid (quantitative). $^1$H NMR, $^{13}$C{$^1$H} NMR, and HRMS were consistent with the title compound.

Compound 1. To a solution of 11-mercaptoundecanoic acid (0.045 g, 0.206 mmol) and HATU (0.078 g, 0.206 mmol) in dichloromethane:N,N-dimethylformamide (1:1 v/v, 5 mL) was added compound 5 (0.105 g, 0.159 mmol) and diisopropylethylamine (0.083 mL, 0.477 mmol). The reaction was stirred at room temperature for 2 hours. The reaction mixture was diluted into ethyl acetate (150 mL) and washed with brine (3×50 mL). The organic phase was dried over Na$_2$SO$_4$, filtered, and concentrated to crude residue that was purified by column chromatography (methanol:ethyl acetate:dichloromethane, 0.5:1.5:8) to yield the title compound as a yellow solid (0.035 g, 0.047 mmol, 30%). $^1$H NMR, $^{13}$C{$^1$H} NMR, and HRMS were consistent with the title compound.

Electrochemistry. Cyclic voltammetry was carried out with a CHI model 660A electrochemical analyzer (CHI Instruments Inc.) in THF with 0.15 M n-Bu$_4$NClO$_4$ supporting electrolyte (0.5 mL) using a three electrode system of SAM-modified gold as the working electrode, a Ag/AgCl wire reference electrode, and a platinum wire counter electrode (Bioanalytical Systems). Model compound (green) was prepared by treating compound 4 with hydrogen peroxide. The results are shown in FIG. 3.

Example 2

Change in E° as a Result of the Presence of H$_2$O$_2$: H$_2$O$_2$Study on PB25$_{13}$ 49 Diluted with C6 Diluent; 5-Minute and 10-Minute Incubations in Na$_2$CO$_3$ buffer (pH 10.1)

A. Purpose

The goal of this study was to test the effect of 5-minute and 10-minute H$_2$O$_2$ incubation times on a diluted SAM of EAM 1 (PB25_49) washed at pH 10.1 and incubated at pH 8.5. H$_2$O$_2$ would decompose the ferrocene on the EAM into a new derivative which would show up at a new potential.

B. Materials

| MATERIALS | BATCH #/ Name | MW | Final C | Stock/ Solvent | NOTES |
|---|---|---|---|---|---|
| 1. EAM for SAM: | PB25_49 | MW = 747.57 | 0.1 mM | 0.5 mg/0.5 mL ethanol | Stock: 0.5 mg |
| 2. Diluent solutions for SAM | (C$_6$S)$_2$ | MW = 234.47 | 0.5 mM | — | Stock C = 9.13× (4.56 mM stock) |
| | (HO—C$_6$S)$_2$ | MW = 266.47 | 0.5 mM | — | Stock C = 7.51× (3.75 mM stock) |
| 3. Electrode testing solution: | 1M LiClO$_4$ | MW = 106.39 | 1M | 10.6 g/1 L H$_2$O | Aqueous solution 1× |
| 4. Hydrogen peroxide | Hydrogen peroxide (50.4%) | MW = 34.01 | 1M | 57 µL/ 943 µL H$_2$O | Made fresh |
| 5. Buffer | Na$_2$CO$_3$ | MW = 105.99 | 100 mM | 0.53 g/50 mL H$_2$O | pH 10.1 |
| 6. Washing buffers | ethanol, nanopure water, Na$_2$CO$_3$, 1M LiClO$_4$ | — | — | — | — |
| 7. Electrodes: | Reference electrode | Counter electrode | Working Electrode | Wash and store | — |
| | Quasi 1 reference (1M LiClO$_4$) | Pt Wire | Au Chip d = 0.25 um | Rinse before and after each use | 13 green chips |

(C$_6$S)$_2$: dihexyl disulfide;
(HO—C$_6$S)$_2$: bis(6-hydroxyhexyl) disulfide;
Note:
Green chips were printed circuit board gold electrode arrays obtained from Osmetech; Nanopure water, as used herein means 18 megaohm water from a Millipore (Billerica, MA, USA) purification system.

EAM 1 Structure:

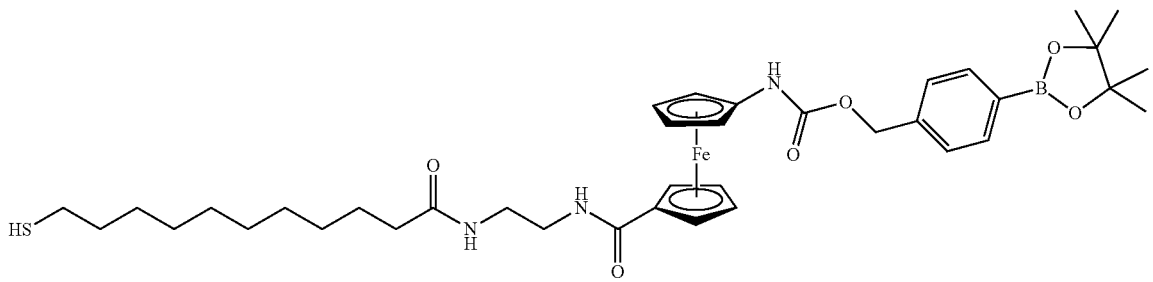

(PB25_49)

C. Procedure

Day 1:

Wash and Assemble Chips 13 (12 for assay+1 for internal reference testing) green chips were washed as follows:
Placed chips in a glass jar with inserts
Sonicated in 0.2% TWEEN™ 20 solution for 5 minutes
Rinsed with nanopure water and ethanol, then dried with Argon
Cleaned in a Plasma Cleaner for 10 minutes
Rinsed with ethanol and dried with Argon
Metal bases, gaskets, and PDMS stamps were washed as follows:
Hand washed with hand soap
Rinsed with ethanol and air dried
Chips were assembled by placing the chip on the double sided tape on center of the metal base, PDMS stamp on the chip, gasket on the PDMS stamp, all clamped together with binder clips.

Prepare Experimental Stocks

EAM stock was prepared by combining the following into the EAM aliquot:

| Stocks | EAM | # Aliquots | Amount | MW | Ethanol | THF | Final Conc. |
|---|---|---|---|---|---|---|---|
| A | PB25_49 | 1 | 0.5 mg ea | 747.57 | 500 µL | none | 1.34 mM |

Prepare SAM Solutions

SAM Solution was prepared by combining the following into separate glass vials:

| [EAM] | AMT µL | D1 | [D1] | AMT µL | D2 | [D2] | AMT µL | Ethanol µL | Tot Vol. µL |
|---|---|---|---|---|---|---|---|---|---|
| 1.34 mM | 493 | (C6S)2 | 4.56 mM | 723 | (HOC6S)2 | 3.75 mM | 879 | 4505 | 6600 |

SAM Incubation

To chips 1-12, 500 µL of above prepared SAM solution was added, followed by overnight incubation.

All chips were placed in plastic containers containing ethanol, sealed with parafilm (to avoid ethanol evaporation and drying of chips). The setup was covered with Aluminum foil.

Day 2:

Internal Reference Measurements:

A 1 mM solution of 1 1'-ferrocene dimethanol was prepared in 1M LiClO$_4$ solution. 1.3 mg of 1 1'-ferrocene dimethanol were combined with 5 mL 1M LiClO$_4$. MW 1 1'-ferrocene dimethanol=246.09

500 µL of 1 mM 1 1'-ferrocene dimethanol solution was added to a clean chip. Quasi 1 reference and platinum counter electrodes were added to the system and CVs were recorded.

Initial Testing to Check for Proper SAM Formation on Chips:

After overnight incubation, the chips were removed from the incubation container. The SAM deposition solution was collected in a vial and dried to obtain recycled EAM for future use.

After overnight incubation, chips 1 through 12 were washed by following the steps shown below:

| Ethanol | 8 times |
|---|---|
| Nanopure water | 4 times |
| Testing buffer, 1M LiClO$_4$ | 2 times |

500 µL of 1M LiClO$_4$ was added to chips 1, 3, 5, 6, 7, 9, 11, and 12, and then chip was plugged in the switchbox.

Reference and counter electrodes were added to the EC system. The white alligator clip from the CHI 650C was connected to the reference electrode (Quasi 1), green clip to the working electrode and the red clip to the counter electrode (Platinum wire, flamed in advance, rinsed with ethanol and water).

The CHI 650C system was used to test all chips. For each test, six files were used: 10000 mV/s, 100 mV/s, 10000 mV/s long, multi CV (20 cycles) and ACV (forward and backward).

The multiplexer was used for testing all chips in this experiment.

After initial testing, chips 1 through 5 and 7 through 11 were washed as follows:

| Nanopure water | 8 times |
|---|---|
| 100 mM Na$_2$CO$_3$ (pH 10.1) | 2 times |

Chips 6 and 12 were washed as follows:

| Nanopure water | 8 times |
|---|---|
| 100 mM NaHCO$_3$ (pH 8.5) | 2 times |

Preparation of Different Concentrations of Hydrogen Peroxide:

Different concentrations of $H_2O_2$ solution were made in 100 mM $Na_2CO_3$ buffer (pH 10.1) immediately before use. Original stock of $H_2O_2$ was at 1M which was made by combining 57 μL of 50% $H_2O_2$ with 943 μL of nanopure water. This stock was left in the 4° C. fridge overnight to allow for muta-rotation. From there on the dilutions were made as shown below:

| Final concentration of $H_2O_2$ (mM) | Ratio (previous to final concentration) | Amount of previous concentration of $H_2O_2$ (μL) | Amount of buffer (μL) | Total volume (μL) |
|---|---|---|---|---|
| 1 | 1:1000 | 2 | 1998 | 2000 |
| 0.1 | 1:10 | 200 | 1800 | 2000 |
| 0.01 | 1:10 | 200 | 1800 | 2000 |
| 0.001 | 1:10 | 200 | 1800 | 2000 |
| 0 | — | 0 | 2000 | 2000 |

Addition of Different Concentrations of $H_2O_2$ to the Chips and Testing:

The hydrogen peroxide solutions made were vortexed well.

500 μL of the respective hydrogen peroxide solutions was added to each chip (1-12) and the solution was mixed thoroughly. The incubation was carried out at room temperature for 5 minutes, while mixing the solution in between with pipette tips at 4:30, 2:30, and 0:30 times, and for 10 minutes, while mixing the solution in between with pipette tips at 7:30, 5:00, and 2:30 times.

After the respective $H_2O_2$ incubations, the chips were washed as follows:

| | |
|---|---|
| Nanopure water | 8 times |
| 100 mM $Na_2CO_3$ (pH 10.1) or 100 mM $NaHCO_3$ (pH 8.5) | 2 times |

Each well was incubated with 500 μL of their respective buffers for 5 minutes. After the chips were incubated with buffer, the chips were washed as follows:

| | |
|---|---|
| Nanopure water | 8 times |
| 1M $LiClO_4$ | 2 times |

The switchbox was used for testing all chips as shown in steps VI d, e and f.

After testing, the chips were washed, cleaned with ethanol and water and then disassembled.

Experiment Outline

| Chip | Chip Name |
|---|---|
| 1 | #1_2_H2O2_0uM_5min_pH10pt1 |
| 2 | #2_2_H2O2_1uM_5min_pH10pt1 |
| 3 | #3_2_H2O2_10uM_5min_pH10pt1 |
| 4 | #4_2_H2O2_100uM_5min_pH10pt1 |
| 5 | #5_2_H2O2_1mM_5min_pH10pt1 |
| 6 | #6_2_H2O2_0uM_5min_pH8pt5 |
| 7 | #7_2_H2O2_0uM_10min_pH10pt1 |
| 8 | #8_2_H2O2_1uM_10min_pH10pt1 |
| 9 | #9_2_H2O2_10uM_10min_pH10pt1 |
| 10 | #10_2_H2O2_100uM_10min_pH10pt1 |
| 11 | #11_2_H2O2_1mM_10min_pH10pt1 |
| 12 | #11_2_H2O2_0uM_10min_pH8pt5 |
| 13 | #11_3_post-H2O2_FcMe2 |

Example 3

$H_2O_2$ Study on PB25_49 Diluted with $C_6$ Diluents; 5-Minute and 10-Minute Incubations in $NaHCO_3$ buffer (pH 8.5) with 100 uM Glucose oxidase ($GO_x$)

Purpose

The goal of this study was to test the effect of 5-minute and 10-minute glucose incubation times on a diluted SAM of PB25_49 washed at pH 10.1 and incubated at pH 8.5. Glucose oxidase was added at 100 μM to these chips to produce $H_2O_2$ that would decompose the ferrocene on the EAM into a new derivative which would show up at a new potential.

B. Materials

| MATERIALS | BATCH #/Name | MW | Final C | Stock/Solvent | NOTES |
|---|---|---|---|---|---|
| 1. EAM for SAM: | PB25_49 | MW = 747.57 | 0.1 mM | 0.5 mg/0.5 mL ethanol | Stock: 0.5 mg |
| 2. Diluent solutions for SAM | $(C_6S)_2$ | MW = 234.47 | 0.5 mM | - | Stock C = 9.13× (4.56 mM stock) |
| | $(HO-C_6S)_2$ | MW = 266.47 | 0.5 mM | - | Stock C = 7.51× (3.75 mM stock) |
| 3. Electrode testing solution | 1M $LiClO_4$ | MW = 106.39 | 1M | 10.6 g/1 L $H_2O$ | Aqueous solution 1× |
| 4. Glucose monohydrate | Glucose | MW = 180.1 | 1M | 0.99 g/5 mL water | Muta-rotated overnight, 4° C. |
| 5. Glucose oxidase | $GO_x$ | MW = 160000 | 100 μM | 12.8 mg/800 μL $NaHCO_3$ buffer | Made fresh on day of use |
| 6. Buffer | $NaHCO_3$ | MW = 105.99 | 100 mM | 4.2 g/500 mL | pH 8.5 |
| 7. Washing buffers | ethanol, nanopure water, $NaHCO_3$, $Na_2CO_3$, buffer, 1M $LiClO_4$ | — | — | — | — |
| 8. Electrodes: | Reference electrode | Counter electrode | Working Electrode | Wash and store | — |
| | Quasi 1 reference (1M $LiClO_4$) | Pt Wire | Au Chip d = 0.25 um | Rinse before and after each use | 11 green chips |

EAM structure is as shown:

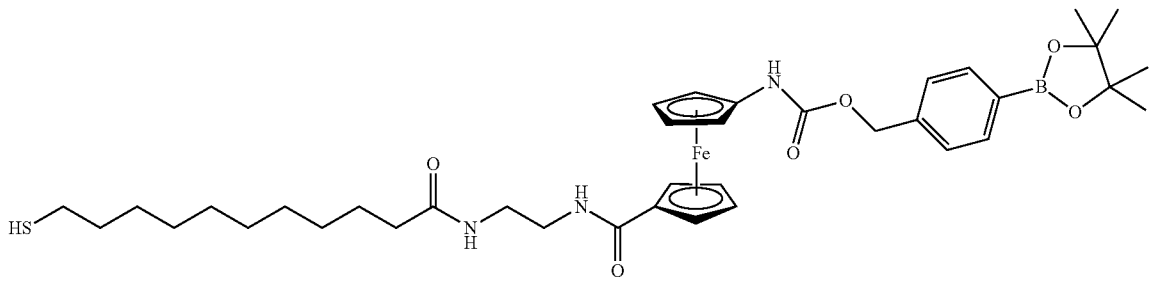

C. Procedure
Day 1:
Wash and Assemble Chips
11 (10 for assay+1 for internal reference testing) green chips were washed as follows:
Placed chips in a glass jar with inserts
Sonicated in 0.2% TWEEN™ 20 solution for 5 minutes
Rinsed with nanopure water and ethanol, then dried with Argon
Cleaned in a Plasma Cleaner for 10 minutes
Rinsed with ethanol and dried with Argon
Metal bases, gaskets, and PDMS stamps were washed as follows:
Hand washed with hand soap
Rinsed with ethanol and air dried
Chips were assembled by placing the chip on the double sided tape on center of the metal base, PDMS stamp on the chip, gasket on the PDMS stamp, all clamped together with binder clips.
Prepare Experimental Stocks
EAM stock was prepared by combining the following into the EAM aliquot:

| Stocks | EAM | # Aliquots | Amount | MW | Ethanol | THF | Final Conc. |
|---|---|---|---|---|---|---|---|
| A | PB25_49 | 1 | 0.5 mg ea | 747.57 | 500 µL | none | 1.34 mM |

Prepare SAM Solutions
SAM Solution was prepared by combining the following into separate glass vials:

| [EAM] | AMT µL | D1 | [D1] | AMT µL | D2 | [D2] | AMT uL | Ethanol µL | Tot Vol. µL |
|---|---|---|---|---|---|---|---|---|---|
| 1.34 mM | 411 | $(C_{11}S)_2$ | 2.67 mM | 1030 | $(HOC_{11}S)_2$ | 2.46 mM | 1119 | 2940 | 5500 |

SAM Incubation
To chips 1-10, 500 µL of above prepared SAM solution was added, followed by overnight incubation.
All chips were placed in plastic containers containing ethanol, sealed with parafilm (to avoid ethanol evaporation and drying of chips). The setup was covered with aluminum foil.
Day 2:
Internal Reference Measurements:
A 1 mM solution of 1 1'-ferrocene dimethanol was prepared in 1M $LiClO_4$ solution. 1.3 mg of 1 1'-ferrocene dimethanol were combined with 5 mL 1M $LiClO_4$. MW 1 1'-ferrocene dimethanol=246.09

500 µL of 1 mM 1 1'-ferrocene dimethanol solution was added to a clean chip. Quasi 1 reference and platinum counter electrodes were added to the system and CVs were recorded.
Initial Testing to Check for Proper SAM Formation on Chips:
After overnight incubation, the chips were removed from the incubation container. The SAM deposition solution was collected in a vial and dried to obtain recycled EAM for future use.
After overnight incubation, chips 1 through 10 were washed by following the steps shown below:

| Ethanol | 8 times |
|---|---|
| Nanopure water | 4 times |
| Testing buffer, 1M $LiClO_4$ | 2 times |

500 µL of 1M $LiClO_4$ was added to chips 1, 3, 5, 6, 8, and 10, and then chip was plugged in the switchbox.
Reference and counter electrodes were added to the EC system. The white alligator clip from the CHI 650C was connected to the reference electrode (Quasi 1), green clip to the working electrode and the red clip to the counter electrode (Platinum wire, flamed in advance, rinsed with ethanol and water).
The CHI 650C system was used to test all chips. For each test, six files were used: 10000 mV/s, 100 mV/s, 10000 mV/s long, multi CV (20 cycles) and ACV (forward and backward).
The multiplexer was used for testing all chips in this experiment.
After initial testing, chips 1 through 10 were washed as follows:

| Nanopure water | 8 times |
|---|---|
| 100 mM $NaHCO_3$ | 2 times |

Preparation of Different Concentrations of Glucose:
A 100 µM Stock of $GO_x$ was made by combining 12.8 mg of $GO_x$ with 800 µL of $NaHCO_3$ buffer, immediately before use.
Different concentrations of glucose solution were made in 100 mM $NaHCO_3$ buffer (pH 8.5) immediately before use. Original stock of glucose was at 1M which was made by combining 0.99 g of Glucose with 5 mL nanopure water. This stock was left in the 4° C. fridge overnight to allow for muta-rotation. From there on the dilutions were made as shown below:

| Final concentration of Glucose (mM) | Ratio (previous to final concentration) | Amount of previous concentration of Glucose (μL) | Amount of buffer (μL) | Total volume (μL) |
|---|---|---|---|---|
| 1 | 1:1000 | 2 | 1998 | 2000 |
| 0.1 | 1:10 | 200 | 1800 | 2000 |
| 0.01 | 1:10 | 200 | 1800 | 2000 |
| 0.001 | 1:10 | 200 | 1800 | 2000 |
| 0 | — | 0 | 2000 | 2000 |

Addition of Different Concentrations of Glucose to the Chips and Testing:

The glucose solutions made were vortexed well and 450 μL were added to the respective chips.

50 μL of 100 uM Glucose oxidase was added to each chip (1-10) and the solution was mixed thoroughly. The incubation was carried out at room temperature for 5 minutes, while mixing the solution in between with pipette tips at 4:30, 2:30, and 0:30 times, and for 10 minutes, while mixing the solution in between with pipette tips at 7:30, 5:00, and 2:30 times.

After the respective glucose incubations, the chips were washed as follows:

| Nanopure water | 8 times |
|---|---|
| $Na_2CO_3$, pH 10.1 | 2 times |

Each well was incubated with 500 μL of $Na_2CO_3$, (pH 10.1) buffer for 5 minutes.

After the chips were incubated with buffer, the chips were washed as follows:

| Nanopure water | 8 times |
|---|---|
| 1M $LiClO_4$ | 2 times |

The switchbox was used for testing all chips as shown in steps VI d, e and f. After testing, the chips were washed, cleaned with ethanol and water and then disassembled.

Experiment Outline

| Chip | Chip Name |
|---|---|
| 1 | #1_2_glucose_0 mM_5 min |
| 2 | #2_2_glucose_1 uM_5 min |
| 3 | #3_2_glucose_10 uM_5 min |
| 4 | #4_2_glucose_100 uM_5 min |
| 5 | #5_2_glucose_1 mM_5 min |
| 6 | #6_2_glucose_0 mM_10 min |
| 7 | #7_2_glucose_1 uM_10 min |
| 8 | #8_2_glucose_10 uM_10 min |
| 9 | #9_2_glucose_100 uM_10 min |
| 10 | #10_2_glucose_1 mM_10 min |
| 11 | #11_3_post-glucose_FcMe2 |

Study: Testing PB25_49 on Green Chips with Troponin

A. Purpose

The goal of this study was to determine the electrochemistry of the EAM PB25_49 on green chips after creating a troponin antibody sandwich and glucose addition resulting in $H_2O_2$ generation due to secondary antibody $GO_x$ labeling.

B. Materials

| MATERIALS | BATCH #/Name | MW | ES Conc | Stock/Solvent | NOTES |
|---|---|---|---|---|---|
| 1. SAM EAM: | PB25_49 | 747.57 | 0.1 mM | 0.5 mg/ 0.5 mL ethanol | Prepared Previously |
| 2. SAM Diluent | $(OH-C_{11}-S)_2$ | 406.72 | 0.5 mM | 1 mg/mL | Prepared Previously |
| II | $(C_{11}S)_2$ | 374.72 | 0.5 mM | 5 mM | Prepared Previously |
|  | $HS-C_{16}-COOH$ | 288.49 | 0.001 mM | 0.5 mg |  |
| 3. Incubation Buffer | PBS | — | — | — | — |
| 4. Testing solution: | 1M $LiClO_4$ | 106.39 | 1M | 10.6 g/L $H_2O$ | Prepared Previously |
| 5. Washing buffers | ethanol, nanopure water, 1M $LiClO_4$, PBS | — | — | — | — |
| 6. Electrodes: | Reference Quasi 4 (1M $LiClO_4$) | Counter Pt Wire | Working Au Chip d = 0.25 μm | Wash and store Rinse before and after each use | 10 Green |

C. Procedure

Day 1:

Prepare SAM Solution

The following Experimental Stocks were prepared by combining the stock material to the corresponding solvents and additives.

EAM: One 0.5 mg PB25_49 aliquots

Add 500 μL ethanol

Bis(11-hydroxyundecyl) disulfide $(HO-C_{11}-S)_2$: Pre-made 1 mg/mL stock

Diundecyl disulfide, $(C_{11}-S)_2$: Pre-made 1 mg/mL stock $HS-C_{16}-COOH$ (16-mercaptohexadecanoic acid) Added 500 μL to 0.5 mg aliquot The SAM solution was prepared by combining the following in a 20 mL glass vial:

PB25_49: 411 μL of 1.34 mM ES (estimated stock concentration) for final concentration of 0.1 mM $(OH-C_{11}-S)_2$: 1.118 mL of 2.46 mM ES for final concentration of 0.5 mM $(C_{11}-S)_2$: 1.030 mL of 2.67 mM for final concentration of 0.5 mM $HS-C_{16}-COOH$: 0.002 mL of 3.47 mM ES for a final concentration of 0.001 mM Ethanol (EtOH): 2.940 mL for a total volume of 5.5 mL SAM Deposition For all chips, the following procedure was performed to deposit the SAM:

Chips were placed in slotted microscope-slide jar with exposed gold surfaces facing inwards Pre-made 0.2% TWEEN™ 20 was added to the jar until the chips were completely submerged After sonicating, the chips were thoroughly rinsed with nanopure water Each chip rinsed with ethanol and dried with argon gas The chips were plasma cleaned for 10 minutes at the "low" plasma setting After plasma cleaning, the chips were again rinsed with ethanol and dried with argon Accessory parts (base, gasket, tub) cleaned by scrubbing with hand soap, rinsing with deionized water and nanopure water, rinsing with ethanol, and air-drying Chips were assembled, then leak tested with ethanol to ensure the gasket was producing a good seal 500 µL of the deposition solution prepared above was added to the tub in each chip Chips were incubated overnight at in a sealed and covered glass container Day 2:

Initial Testing to Verify Proper SAM Formation

Following overnight incubation, chips removed from containers. The chips were washed as follows:

2× Ethanol

6× Nanopure water

2×LiClO$_4$

500 µL testing solution (see table above) was added in each tub

The electrodes (see table above) were connected to the CHI system (the Pt counter was cleaned with a propane torch and ethanol rinse prior to use)

For all chips:

Cyclic voltammetry was performed between ranges determined during testing with 10000 mV/s CV, 100 mV/s CV, EDC, NHS Activation The Chips were washed 4× with nanopure water before addition of any further solutions.

Added 1000 µL of EDC to 1000 µL of NHS.

Added 200 µL of this mixed solution to 4 chips

Incubate for 30 minutes. NOTE: All incubations were done in empty pipette tip containers and covered with foil to minimize light exposure.

Wash 4× with nanopure water after incubation

Streptavidin

Add 200 µL streptavidin solution

Incubated for 1 hour

Wash 4×PBS. 1×LiClO$_4$.

Chips 3-6 were tested as in 3.5.1

NOTE: only the chips that were tested were washed with LiClO$_4$. All chips that were tested were washed again 4×PBS. This applies to all steps below.

| Chip | Material |
|---|---|
| 1 | Gox- Biotin |
| 2 | Gox- Biotin |
| 3 | Tested after each step |
| 4 | Tested after each step |
| 5 | Tested after each step |
| 6 | Tested after each step |
| 7 | Tested only immediately before glucose |
| 8 | Tested only immediately before glucose |
| 9 | Only tested after addition of glucose |
| 10 | Only tested after addition of glucose |

Ethanolamine Capping

200 µL ethanolamine was added to each chip

Incubate for 15 minutes

Wash 4×PBS

BSA Blocking

Add 0.1% BSA (bovine serum albumin)

Incubate 10 minutes

Wash 4×PBS (phosphate buffered saline), 1×LiClO$_4$

Chips 3-6 were tested as in 3.5.1

GO$_x$ and Primary Antibody Addition

Concentration of GO$_x$-biotin stock is 1 mg/mL so 4 µL of GO$_x$-biotin stock was added to 396 µL PBS.

Added 200 µL of 10 µg/mL GO$_x$-biotin to Chip #1&2.

Incubated for 1 hour

Stock of mAb 19C7-biotin is at 1.7 mg/mL so 8 µL was added to 792 µL of PBS for a concentration of 17 µg/mL Added 100 µL antibody-biotin to #3-10

Both solutions were left to incubate for 45 minutes.

Chips 3-6 were washed 4×PBS, 1×LiClO$_4$ and tested.

Troponin and Secondary Antibody Incubation

The troponin aliquot (1 mg/mL) was taken from the −20° C. freezer and let thaw. 1 µL was added to 9 µL of PBS, yielding 100 µg/mL. NOTE: this dilution was not done in the Urea/tris buffer.

1 µL of the 100 µg/mL was added to 48 µL of PBS mAb16A11-Gox was removed from the fridge (1.7 mg/mL)

1 µL of mAb16A11-Gox was also added to the PBS/troponin solution and vortex.

This solution was incubated for 30 mins.

Gox-biotin Testing

Chips #1, #2 were washed 4×PBS, 1×LiClO$_4$ and tested.

After testing they were washed 4×PBS.

A 2 mM Glucose solution was prepared by taking 20 µL of 1M to 9980 µL of NaHCO$_3$ pH 8.5.

500 µL of 2 mM glucose was added to both chips and incubated for 10 minutes.

1,2 were then washed 4×PBS, 1×LiClO$_4$ and tested.

Chips were washed 4×PBS

Chips were incubated with 100 mM H$_2$O$_2$ for 2 minutes, then washed and tested Troponin and Secondary Antibody Addition Chips 3-10 were washed 4×PBS.

The 50 µL incubation of troponin and mAb16A11-Gox was diluted up to 1.2 mL in PBS. Solution was vortexed 150 µL of this solution was added to chips 3-10 and incubated for 30 mins.

Troponin and Secondard Antibody Testing.

Chips 3-10 were washed 4×PBS.

Chips 5-8 were washed 1× LiClO$_4$ and tested.

Chips 5-8 were washed with 4×PBS

500 µL of 100 mM H$_2$O$_2$ was added to #6-7 for 2 minutes. After incubation they were washed 4×PBS, 1×LiClO$_4$ and tested.

2 mM glucose was added to Chips 9, 10 and incubated for 20 minutes. After incubation they were washed 4×PBS, 1×LiClO$_4$ and tested.

Monolayer Preparation. Gold-evaporated electrodes were cleaned with a 5 minute sonication in 0.2% Tween 20 solution, washed with ethanol before undergoing 10 minutes of plasma ionization. The electrodes were then washed with ethanol before being exposed to the deposition solution. The deposition solution was composed of Compound 1 (0.1 mM), dihexyl disulfide (0.5 mM ($C_6$—S)$_2$) and bis(6-hydroxyhexyl) disulfide (0.5 mM (HO—$C_6$—S)$_2$) and 16-mercaptohexadecanoic acid (0.01 mM, MHA, HS—$C_{16}$—COOH). The deposition solution was incubated on the gold electrodes overnight for ~18 hours. The deposition solution was then removed and the electrodes were washed with ethanol followed by water. The MHA was activated for 30 minutes using a 1/1 volume/volume of N-hydroxysuccinimide (NHS) (0.1 M) and 1-Ethyl-3-(3-dimethylaminopropyl)carbodiimide (EDC) (0.4 M). Following this activation the electrodes were washed with water and incubated 1 hour with streptavidin (0.05 mg/mL) in 10 mM sodium acetate pH 5.7. The electrodes were washed with PBS between each step for the remaining steps of the assay. Ethanolamine (0.1 mM NaHCO$_3$) was added to cap the unreacted MHA sites for 15 minutes. BSA (0.1 weight %) in PBS buffer was added for 10 minutes to reduce nonspecific binding. The primary antibody (mAb-19c7-biotin, HyTest) was added at a concentration of 17 μg/mL and incubated for 45 minutes. During this time, the secondary antibody (34 μg/mL, mAb-16A11-GOx, Hytest) was incubated with Human cardiac troponin I (2 μg/mL). The secondary antibody-troponin complex was then added to the electrodes at concentration of interest and incubated for 30 minutes. At this point the full "sandwich" is built up on the MHA in the monolayer. Glucose (2 mM) was then incubated for 10 minutes, solution was removed, electrodes were washed with PBS and the cyclic voltammograms were recorded in LiClO$_4$ (1 M).

Example 4

NADH Dose Response for Complete Lysis Buffer with Zinc Acetate

Purpose: The purpose of this experiment is to get dose response for NADH without amplification system for complete lysis buffer with zinc acetate
Materials and Methods
Protease Inhibitor Calbiochem 539134 and VWR 80053-85
Benzonase Novagen #70664
NADH oxidase (GTP, Aliquot: 0.4 U/50 μL, tube; =17.2 μg/tube; =0.344 μg/μL)
Buffer Used:
0.5×HEPES, pH 7.4 (29 mM Maltoside)
1:200 Benzonase
1:2000 Protease inhibitor
Phosphatase Inhibitor Cocktail (0.5×)
2.5 mM NaF
3 μM Sodium Orthovanadate (instead of 500 μM)
500 μM Sodium Pyrophosphate decahydrate
500 μM beta-Glycerolphosphate
2.5 mM Sodium Azide
100 μM zinc acetate
Desired Concentrations in Well/Tube

| Solution | Concentration |
| --- | --- |
| NADH oxidase | 5 ng/μL |
| FAD | 10 μM |
| NADH | 3 μM |
|  | 1 μM |
|  | 300 nM |
|  | 100 nM |
|  | 30 nM |
|  | 10 nM |
|  | 3 nM |
|  | 1 nM |
|  | 0.3 nM |

Working Solutions
Working NADH oxidase: Take NADH oxidase aliquot 50 μL. Add 1.45 μL of stock per 100 μL of total NADH reaction solution.
FAD: Make a 7.5 mM stock solution by dissolving 5.8 mg in 1000 μL nanopure water. Use 7.5 mM stock and make 1 mM stock by taking 13.3 μL of 7.5 mM stock and diluting upto 100 μL. Add 1 μL per 100 μL reaction.
ADHP: Add 220 μL to 100 μL stock of 16 mM ADHP stock to give 5 mM stock. Add 2.3 μL/70 μL in each well to get 160 μM conc.
HRP: Add 0.6 μL of 1 u/μL HRP to 999.4 μL water. Add 2.3 μL HRP/70 μL reaction to each well
NADH:

| NADH Conc | Stock (mM) | Water μL | Final conc (10 μL in 100 μL sample) |
| --- | --- | --- | --- |
| 10 mM | 10 | — | 1 mM |
| 3 mM | 30 | 70 | 300 μM |
| 1 mM | 30 | 60 | 100 μM |
| 300 μM | 30 | 70 | 30 μM |
| 100 μM | 30 | 60 | 10 μM |
| 30 pM | 30 | 70 | 3 μM |
| 10 μM | 30 | 60 | 1 μM |
| 3 μM | 30 | 70 | 300 nM |
| 1 μM | 30 | 60 | 100 nM |
| 300 nM | 30 | 70 | 30 nM |
| 0 mM | — | 60 | 0 |
| Unknown | — | — | — |

Reaction: Composition Per Well

| sample | Complete lysis buffer with inhibitor cocktail and benzonase | Buffer | Take NADH sample (1 mM-30 nM) μL | FAD 1 mM | NADH oxidase 0.344 ug/μL |
| --- | --- | --- | --- | --- | --- |
| 1 | HEPES buffer | 90 μL | 10 μL | 1 μL | 1.45 μL |
| 2 | HEPES buffer | 90 μL | 10 μL | 1 μL | 1.45 μL |
| 3 | HEPES buffer | 90 μL | 10 μL | 1 μL | 1.45 μL |
| 4 | HEPES buffer | 90 μL | 10 μL | 1 μL | 1.45 μL |
| 5 | HEPES buffer | 90 μL | 10 μL | 1 μL | 1.45 μL |
| 6 | HEPES buffer | 90 μL | 10 μL | 1 μL | 1.45 μL |
| 7 | HEPES buffer | 90 μL | 10 μL | 1 μL | 1.45 μL |
| 8 | HEPES buffer | 90 μL | 10 μL | 1 μL | 1.45 μL |
| 9 | HEPES buffer | 90 μL | 10 μL | 1 μL | 1.45 μL |
| 10 | HEPES buffer | 90 μL | 10 μL | 1 μL | 1.45 μL |
| 11 | HEPES buffer | 90 μL | 10 μL | 1 μL | 1.45 μL |
| 12 | HEPES buffer | — | 100 μL (cell lysate) | 1 μL | 1.45 μL |

100 μL sample each.

1. Each component was added to a 96 well plate and incubated for 2 hours.
2. After 2 hrs 30 μL from each reaction sample was taken and pH adjusted to pH 10 by adding 10 μL of 400 mM carbonate. 30 μL was then incubated on e-chips.
3. 70 μL was taken and added to ADHP and HRP for optical readout
4. A Corning Polystyrene 96-well plate was used for this experiment. The appropriate filters were inserted into the Plate Reader for the ADHP and measurements were taken.
ADHP—Excitation=550 nm; Emission=590 nm
Echip:
Chips used were 16-microelectrode array composed of evaporated gold, ablated into the desired circuit. The structure of PB65-33 is:

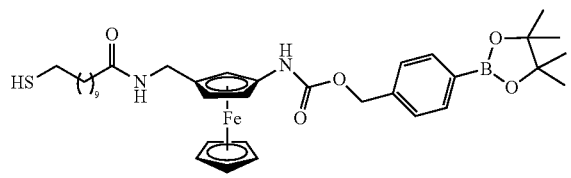

Materials/SAM Solution Preparation

| Ratio (EAM:D1) | EAM: (1 mg/1 mL EtOH) PB65-33 | PEG3-C11-SH MW: 336.53 | Ethanol |
|---|---|---|---|
| 0.1:0.25 PB65_33: MW 690.5 | 994 μL of 1.45 mM stock (EAM PB65-33): 0.5 mg aliquot | 1212 μL of 2.97 mM stock (11-mercaptoundecyl) triethyleneglycol (SENSOPATH) (1 mg/0.3 mg) | 12.194 mL |
| Target Incubation Buffer: | 1x PBS, 100 mM NaHCO₃ pH 10 | High pH Washing Buffer: | |
| Testing Buffer: Washing Buffer | 1M LiClO₄ • 3H₂O Nanopure water | MW: 160.44 | |
| Electrodes: | External Quasi and platinum wire | | 10 chips |

PEG3-C11-SH: (11-mercaptoundecyl)triethylenedlycol (SENSOPATH)
Day 1: SAM Deposition
1.1 For all chips, the following procedure was performed to deposit the SAM
1.2. Chips were rinsed again with ethanol and dried with argon
1.3. Accessory parts (gasket, tubs) cleaned by washing machine, rinsed with ethanol and air-dried. Bases were cleaned by hand.
1.4. 200 μL of the deposition solution prepared above was added to each chip.
1.5. Chips were incubated overnight in ethanol incubation chamber
Day 2: Initial washing of chips
2.1 Following overnight incubation, chips removed from containers
2.2 The chips were washed as follows:
2.2.1. 8× ethanol
2.2.2. 4× nanopure water
Target Incubation
4.1. Each chip was incubated as designated in table below. Buffer used for the samples was complete lysis buffer with modified Phosphatase inhibitor with zinc acetate and sodium azide. The samples were pH adjusted to pH 10 with 400 mM carbonate in (1:4 ratio)
4.2. After target incubation of 10 min., the chips were washed 4× water, 2×LiClO₄ and tested

| Macro Chips - NADH (3 chips per conc) | Solution |
|---|---|
| Chip 1 | 1 mM |
| Chip 2 | 300 μM |
| Chip 3 | 100 μM |
| Chip 4 | 30 μM |
| Chip 5 | 10 μM |
| Chip 6 | 3 μM |
| Chip 7 | 1 μM |
| Chip 8 | 300 nM |
| Chip 9 | 100 nM |
| Chip 10 | 30 nM |
| Chip 11 | 0 |
| Chip 12 | Unknown Cell lysate |

Example 5

ATP Detection via Glycerol Kinase/Glycerol-3-Phosphate Oxide System

ATP can be electrochemically detected by exploiting the ATP-dependent enzymatic reactions with a SAM-modified gold electrode by using the activities of glycerol kinase (GK) and glycerol-3-phosphate oxidase (G3PO) if the co-substrate glycerol is present in the reaction mixture (see Murphy, L. J. et al. *Anal. Chem.* 1994, 66, 4345-4353; and Llaudet, E. et al., *Anal. Chem.* 2005, 77, 3267-3273).

First, GK catalyzes the formation of glycerol-3-phosphate from glycerol and ATP. Subsequently, G3PO oxidizes glycerol-3-phosphate to yield glycerone phosphate and hydrogen peroxide. Thus, the amount of peroxide produced is directly linked to the amount of ATP in the sample if glycerol is in excess. An approach toward the electrochemical detection of peroxide produced from this enzymatic reaction sequence is shown in FIG. 14.

The ATP sensor is based on a SAM-modified gold electrode that contains peroxide-reactive electroactive molecules (EAMs). The initial apparent formal potential of EAMs in the monolayer characterizes the sensor "off" state. Upon exposure to an ATP-containing sample matrix, hydrogen peroxide production triggers an irreversible elimination reaction in the immobilized EAMs resulting in a signal "on" change in apparent formal potential of ferrocene groups that is detected electrochemically. This enzyme-triggered redox altering chemical elimination (E-TRACE) reaction for a representative class of ferrocene EAMs is shown in FIG. 11. (see e.g. U.S. patent application Ser. No. 12/853,204).

Purpose:
The purpose of this experiment was to demonstrate that ATP levels detected in cell lysates matched the same value on the standard curve in the amplified and unamplified detection assays.

Materials and Methods:
Glycerol (2 mM), Glycerol kinase (GK, 1.33 U/mL), Glycerol 3-phosphate oxidase (G3PO, 1.33 U/mL), ATP (0 nM-1 mM)
Buffers Used:
0.5×HEPES, pH 7.4 (29 mM Maltoside)
1:200 Benzonase
1:2000 Protease inhibitor 1:100 Phosphatase Inhibitor cocktail (0.5×)
2.5 mM NaF
3 μM Sodium Orthovanadate
500 μM Sodium Pyrophosphate decahydrate
500 μM beta-Glycero-phosphate
100 μM Zn acetate
2.5 mM $NaN_3$ added to the phosphatase inhibitor cocktail as a catalase inhibitor for $H_2O_2$
ATP: 0 nM-1 mM→E-tRACE Assay Only (in Triplicate)
ATP dilutions were made in nanopure water. This was used to make the ATP serial dilutions, and reconstitute GK and G3PO enzymes.
Desired Concentrations in Well/Tube

| Solution | Concentration |
| --- | --- |
| ATP | 0 nM-1 mM |
| Glycerol | 2 mM |
| Glycerol kinase (1×) | 1.33 U/mL |
| Glycerol 3-phosphate oxidase (1×) | 1.33 U/mL |
| ADHP | 160 μM |
| HRP - 8× | 0.16 U/mL |

| Buffer Types | Concentration of components |
| --- | --- |
| Buffer A - HEPES, pH 7.4 (Maltoside 29 mM) | 0.5× HEPES 25 mM, NaCl - 100 mM |
| Inhibitors | 1:200 Benzonase added |
| Phosphatase inhibitor cocktail (modified) | 0.5× (3 μM orthovanadate) - in solution (different prep) |
| $NaN_3$ | 2.5 mM |
| Zn acetate | 100 μM |
| Protease inhibitor cocktail | 1:2000 (Calbiochem 539134 VWR 80053-85 |

Assay volume will be 100 μL.
GK: 10 U/Aliquot
Reconstitute in 250 μL buffer-0.04 U/μL. Take 5 μL of 0.04 U/μL stock and add to each well—final assay concentration—1×. (For 100 μL assay volume, add 3.57 μL of GK for each data point)
G3PO: 5 U/Aliquot
Reconstitute in 125 μL buffer=0.04 U/μL. Take 5 μL of 0.04 U/μL stock and add to each well—final assay concentration—1.33 U/mL (1×). (For 100 μL assay volume, add 3.57 μL of G3PO for each data point)
Glycerol: 2 mM (MW—92.09 g/mol, density—1.261 g/cm$^3$)
(2 mM)(150 μL)=(5 μL) (x)→x=60 mM needed
Take 22 μL of Glycerol stock and add to 4978 μL buffer to make a 5 mL total stock (60 mM Glycerol stock)
Take 3.57 μL and add to each well to make 100 μL total volume
Benzonase: 1:200 in 0.5×HEPES Buffer, pH 7.4
Take 5 μL of Benzonase stock and add to 1 mL of 0.5× HEPES, pH 7.4 buffer
Phosphatase Inhibitor Cocktail (Modified) 1:100—Weighed out each of the components and added
1) 250 mM $NaN_3$ to 5 mL (50×) phosphatase inhibitor cocktail solution—such that final concentration in 0.5× buffer will have 2.5 mM $NaN_3$.
2) Also made a 1M stock of Zn acetate and added 1 μL of 1M stock to 100 μL of 50× Phosphatase inhibitor cocktail aliquot—such that final concentration of Zn acetate in 0.5× lysis buffer=100 μM.

Add (1/100)*1 mL=10 μL of phosphatase inhibitor cocktail added to 0.5×HEPES, lysis buffer
Protease Inhibitor (1:2000 Dilution)—in 0.5×HEPES, pH 7.4
(1/2000)*1 mL=0.5 μL Protease inhibitor added to 1 mL 0.5×HEPES, lysis buffer
Assay Conditions: (GK—1×, G3PO—1×)—HEPES 0.5× (0.5×Phosphatase Inhibitor)
100 μL of each sample was incubated for 2.5 hrs. The following components were added to the tube for 2.5 hrs incubation before putting them on chips for target testing.
Upon incubation in 0.5×HEPES, pH 7.4 for 2.5 hrs, adjust pH to 10 by adding 33.3 μL 400 mM $Na_2CO_3$ (100 mM in assay)
Total 133.3 μL sample (per data point)—25% sample dilution occurs in the process of adjusting to pH 10
Add 30 μL sample to each chip all at once and incubate (for 10 min.) and wash them before reading

| Components added | 0 nM-1 mM ATP |
| --- | --- |
| Buffer | 90 μL |
| GK | 3.57 μL |
| G3PO | 3.57 μL |
| Glycerol (2 mM) | 3.57 μL |
| ATP | 10 μL |

E-chip Experiment:
Chips used were 16-microelectode array composed of evaporated gold, ablated into the desired circuit. Structure of PB65-33:

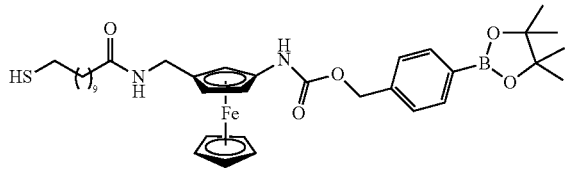

Figure 16:
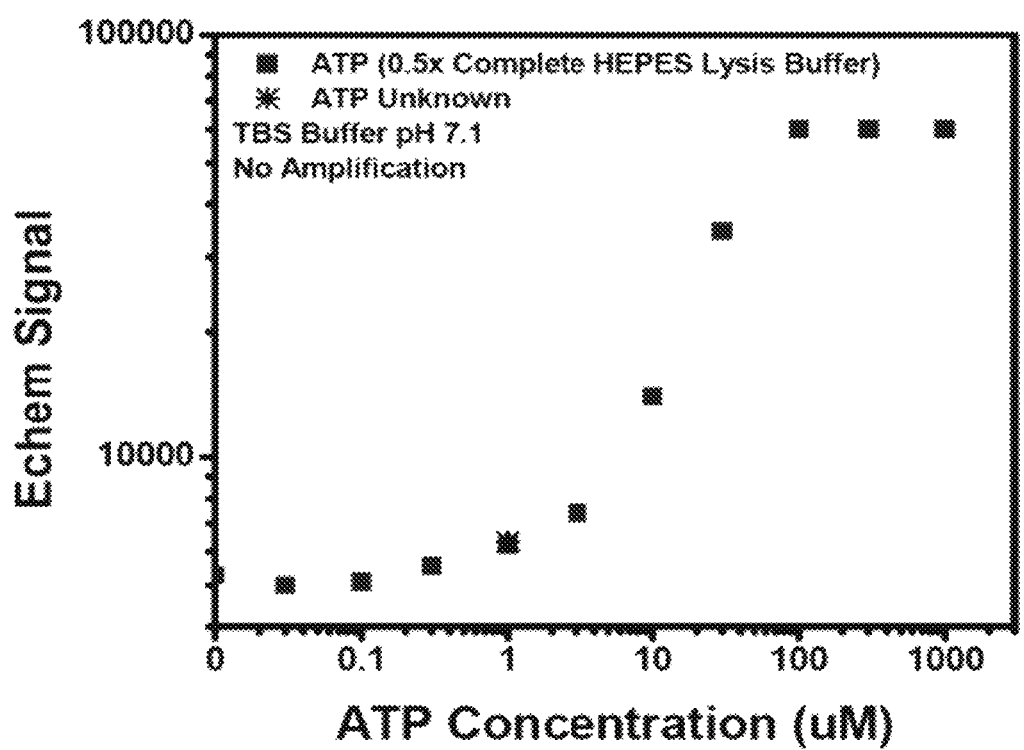
FIG. 16. Electrochemical data for ATP detection as described in Example 5.

Run e-chip on full ATP curve (0 nM-1 mM)
Average Peak current ratio and Area ratio were analyzed for all concentrations.
Chips were washed 8× ethanol, 4× with water and incubated with target solution of 10 min. right away
Upon 10 min. incubation, chips were washed 4× water and 2×$LiClO_4$ and tested with 1 M $LiClO_4$ testing solution.
Results are shown in FIG. 16. From this experiment it was demonstrated that the lysate concentration of ATP is roughly 1 μM

We claim:
1. A method for detecting a target analyte in a test sample, said method comprising:
(a) providing a solid support comprising an electrode comprising:
(i) a self-assembled monolayer (SAM),
(ii) a covalently attached electroactive active moiety (EAM) comprising a transition metal complex comprising a self-immolative moiety and a peroxide sensitive moiety (PSM), wherein said EAM has a first $E^o$, and
(b) contacting said target analyte and said solid support under conditions wherein said target analyte reacts with a peroxide generating enzyme to generate peroxide and said self-immolative moiety is removed such that said EAM has a second $E^o$, wherein said peroxide generating enzyme is immobilized or physisorbed onto the solid support, the electrode, or SAM, or wherein said peroxide generating enzyme is in a solution in contact with the electrode; and (c) detecting said second $E^o$ as an indication of the presence of said target analyte.

2. The method according to claim 1, wherein said target analyte is NADH and said peroxide generating moiety is NADH oxidase (NAOX).

3. The method according to claim 1, wherein said solid support comprises an array of electrodes.

4. The method according to claim 1, wherein said transition metal is selected from the group consisting of iron, ruthenium and osmium.

5. The method according to claim 1, wherein said EAM is a ferrocene.

6. The method according to claim 1, wherein said detecting is done amperommetrically at each first and second $E^o$.

7. A method for detecting a target analyte in a test sample, said method comprising:
(a) providing a solid support comprising an electrode comprising:
 (i) a self-assembled monolayer (SAM),
 (ii) a covalently attached electroactive active moiety (EAM) comprising a transition metal complex comprising a self-immolative moiety and a peroxide sensitive moiety (PSM), wherein said EAM has a first $E^o$, and
(b) contacting said target analyte and said solid support in the presence of an intermediary enzyme and an additional substrate for said enzyme, under conditions wherein if said analyte is present, the target analyte and said additional substrate reacts with the intermediary enzyme to form a first complex;
(c) contacting said target analyte and said solid support in the presence of the intermediary enzyme and the additional substrate for said enzyme with a peroxide generating enzyme under conditions wherein if a first complex is formed, said first complex reacts with said peroxide generating enzyme to generate peroxide and said self-immolative moiety is removed such that said EAM has a second $E^o$, wherein said intermediary enzyme is immobilized or physisorbed onto the solid support, the electrode, or SAM, or wherein said intermediary enzyme is in a solution in contact with the electrode; and
(d) detecting said second $E^o$ as an indication of the presence of said target analyte.

8. The method according to claim 7, wherein steps (b) and (c) are carried out separately.

9. The method according to claim 7, wherein steps (b) and (c) are carried out simultaneously.

10. The method according to claim 7, wherein said target analyte is ATP, said intermediary enzyme is glycerol kinase and said substrate of said intermediary enzyme is glycerol, and said peroxide generating moiety is glycerol-3-oxidase.

11. A composition comprising a solid support comprising:
(a) an electrode comprising:
 (i) a self-assembled monolayer (SAM);
 (ii) a covalently attached electroactive active moiety (EAM) comprising a transition metal complex comprising a self-immolative moiety and a peroxide sensitive moiety (PSM), wherein said EAM has a first $E^o$ when said self-immolative moiety is covalently attached to said EAM and a second $E^o$ when said self-immolative moiety is absent; and
 (iii) a capture binding ligand comprising a substrate of an ATP-dependent intermediary enzyme; and
(b) a soluble capture ligand comprising a peroxide generating moiety,
wherein an intermediary enzyme is immobilized or physisorbed onto the solid support, the electrode, or SAM.

12. A composition comprising a solid support comprising:
an electrode comprising:
 (i) a self-assembled monolayer (SAM);
 (ii) a covalently attached electroactive active moiety (EAM) comprising a transition metal complex comprising a self-immolative moiety and a peroxide sensitive moiety (PSM), wherein said EAM has a first $E^o$ when said self-immolative moiety is covalently attached to said EAM and a second $E^o$ when said self-immolative moiety is absent; and
 (iii) a peroxide generating enzyme,
wherein said peroxide generating enzyme is immobilized or physisorbed onto the solid support, the electrode, or SAM.

13. A composition comprising:
(I) a solid support comprising:
 (a) an electrode comprising:
  (i) a self-assembled monolayer (SAM);
  (ii) a covalently attached electroactive active moiety (EAM) comprising a transition metal complex comprising a self-immolative moiety and a peroxide sensitive moiety (PSM), wherein said EAM has a first $E^o$ when said self-immolative moiety is covalently attached to said EAM and a second $E^o$ when said self-immolative moiety is absent; and
  (iii) a capture binding ligand comprising a substrate of an ATP-dependent intermediary enzyme; and
 (b) a soluble capture ligand comprising a peroxide generating moiety; and
(II) an intermediary enzyme in a solution in contact with the electrode.

14. A composition comprising:
(a) a solid support comprising:
 an electrode comprising:
  (i) a self-assembled monolayer (SAM); and
  (ii) a covalently attached electroactive active moiety (EAM) comprising a transition metal complex comprising a self-immolative moiety and a peroxide sensitive moiety (PSM), wherein said EAM has a first $E^o$ when said self-immolative moiety is covalently attached to said EAM and a second $E^o$ when said self-immolative moiety is absent; and
(b) a peroxide generating enzyme, wherein said peroxide generating enzyme is in a solution in contact with the electrode.

* * * * *